(12) United States Patent
Glaser et al.

(10) Patent No.: US 8,084,026 B2
(45) Date of Patent: *Dec. 27, 2011

(54) MULTISPECIFIC BINDING MOLECULES COMPRISING CONNECTING PEPTIDES

(75) Inventors: Scott Glaser, San Diego, CA (US); Xiufeng Wu, San Diego, CA (US)

(73) Assignee: Biogen Idec MA Inc., Cambridge, MA (US)

( * ) Notice: Subject to any disclaimer, the term of this patent is extended or adjusted under 35 U.S.C. 154(b) by 621 days.

This patent is subject to a terminal disclaimer.

(21) Appl. No.: 11/825,666

(22) Filed: Jul. 5, 2007

(65) Prior Publication Data
US 2009/0162380 A1 Jun. 25, 2009

Related U.S. Application Data

(63) Continuation of application No. PCT/US2006/000505, filed on Jan. 5, 2006.

(60) Provisional application No. 60/641,761, filed on Jan. 5, 2005.

(51) Int. Cl.
*A61K 39/00* (2006.01)
*A61K 39/395* (2006.01)
*C12P 21/08* (2006.01)
*C07K 16/46* (2006.01)
*C07K 16/28* (2006.01)

(52) U.S. Cl. ............... 424/133.1; 424/136.1; 424/143.1; 424/192.1; 530/387.3; 530/388.22

(58) Field of Classification Search .................. None
See application file for complete search history.

(56) References Cited

U.S. PATENT DOCUMENTS

| | | |
|---|---|---|
| 4,485,045 A | 11/1984 | Regen |
| 4,544,545 A | 10/1985 | Ryan et al. |
| 4,816,567 A | 3/1989 | Cabilly et al. |
| 5,082,783 A | 1/1992 | Ernst et al. |
| 5,166,322 A | 11/1992 | Shaw et al. |
| 5,206,344 A | 4/1993 | Katre et al. |
| 5,208,020 A | 5/1993 | Chari et al. |
| 5,219,996 A | 6/1993 | Bodmer et al. |
| 5,225,538 A | 7/1993 | Capon et al. |
| 5,348,876 A | 9/1994 | Michaelsen et al. |
| 5,530,101 A | 6/1996 | Queen et al. |
| 5,618,920 A | 4/1997 | Robinson et al. |
| 5,624,821 A | 4/1997 | Winter et al. |
| 5,641,870 A | 6/1997 | Rinderknecht et al. |
| 5,661,004 A | 8/1997 | Browning et al. |
| 5,670,149 A | 9/1997 | Browning et al. |
| 5,677,425 A | 10/1997 | Bodmer et al. |
| 5,766,897 A | 6/1998 | Braxton |
| 5,795,964 A | 8/1998 | Browning et al. |
| 5,821,333 A | 10/1998 | Carter et al. |
| 5,837,821 A | 11/1998 | Wu |
| 5,859,205 A | 1/1999 | Adair et al. |
| 5,877,291 A | 3/1999 | Mezes et al. |
| 5,925,351 A | 7/1999 | Browning et al. |
| 5,959,083 A | 9/1999 | Bosslet et al. |
| 5,976,845 A | 11/1999 | Mezes et al. |
| 6,011,138 A | 1/2000 | Reff et al. |
| 6,063,905 A | 5/2000 | Capra et al. |
| 6,066,719 A | 5/2000 | Zapata |
| 6,071,515 A | 6/2000 | Mezes et al. |
| 6,207,815 B1 | 3/2001 | Mezes et al. |
| 6,214,984 B1 | 4/2001 | Zapata |
| 6,218,149 B1 | 4/2001 | Morrison et al. |
| 6,284,536 B1 | 9/2001 | Morrison et al. |
| 6,312,691 B1 | 11/2001 | Browning et al. |
| 6,329,507 B1 | 12/2001 | Mezes et al. |
| 6,348,581 B1 | 2/2002 | Anderson et al. |
| 6,403,087 B1 | 6/2002 | Browning et al. |
| 6,495,137 B1 | 12/2002 | Mezes et al. |
| 6,552,170 B1 | 4/2003 | Thompson et al. |
| 6,576,746 B2 | 6/2003 | McBride et al. |
| 6,669,941 B1 | 12/2003 | Browning et al. |

(Continued)

FOREIGN PATENT DOCUMENTS
EP 0327378 A1 8/1989
(Continued)

OTHER PUBLICATIONS

Hudson et al, J. Immunological Method 231: 177-189, 1999.*
Aalberse, R.C., et al. "IgG4 breaking the rules." *Immunology*. 2002; 105:9-19.
Adams, Gregory P., et al., "Highly Specific in Vivo Tumor Targeting by Monovalent and Divalent Forms of 741F8 Anti-c-*erb*B-2 Single-Chain Fv[1]," *Cancer Research*, vol. 53:4026-4034 (1993).
Adkins, Heather B. et al, "Antibody blockade of the Cripto CFC domain suppresses tumor cell growth in vivo," *The Journal of Clinical Investigation*, vol. 112(4):575-587 (2003).

(Continued)

*Primary Examiner* — Phuong Huynh
(74) *Attorney, Agent, or Firm* — Nelson Mullins Riley & Scarborough LLP; Megan E. Williams

(57) ABSTRACT

The instant invention describes novel multispecific binding molecules comprising synthetic connecting peptides. The synthetic connecting peptides result in the preferential synthesis of multispecific binding molecules comprising polypeptide chains that are linked via at least one interchain disulfide linkage. In addition, the invention pertains to compositions in which a majority of the multispecific binding molecules comprising polypeptide chain that are linked via at least one interchain disulfide linkage or are not linked via at least one intrachain disulfide linkage. In a specific embodiment, the invention pertains to compositions comprising multispecific dimeric binding molecules said molecules comprising at least a first binding site specific for a tumor necrosis factor (TNF) receptor or a ligand of a TNF receptor family member and at least a second binding site; and at least two polypeptide chains comprising at least one heavy chain portion and a synthetic connecting peptide; wherein greater than about 50% of the dimers comprise polypeptide chains that are linked via at least one interchain disulfide linkage.

46 Claims, 15 Drawing Sheets

U.S. PATENT DOCUMENTS

| | | | |
|---|---|---|---|
| 6,737,056 B1 | 5/2004 | Presta | |
| 6,759,518 B1 | 7/2004 | Kontermann et al. | |
| 7,001,598 B2 | 2/2006 | Browning et al. | |
| 7,030,080 B2 | 4/2006 | Browning et al. | |
| 7,060,667 B1 | 6/2006 | Browning et al. | |
| 2002/0002271 A1 | 1/2002 | Rinderknecht et al. | |
| 2002/0009446 A1 | 1/2002 | Magilavy | |
| 2002/0028486 A1 | 3/2002 | Morrison et al. | |
| 2002/0062010 A1 | 5/2002 | Arathoon et al. | |
| 2002/0155109 A1 | 10/2002 | Lynch | |
| 2002/0197254 A1 | 12/2002 | Browning et al. | |
| 2003/0060444 A1 | 3/2003 | Finney et al. | |
| 2003/0078385 A1 | 4/2003 | Arathoon et al. | |
| 2003/0207346 A1 | 11/2003 | Arathoon et al. | |
| 2004/0033511 A1 | 2/2004 | Pfizenmaier et al. | |
| 2004/0058394 A1 | 3/2004 | Garber et al. | |
| 2004/0101905 A1 | 5/2004 | Brekke et al. | |
| 2004/0198635 A1 | 10/2004 | Browning et al. | |
| 2005/0037003 A1 | 2/2005 | Browning et al. | |
| 2005/0097625 A1 | 5/2005 | Meade et al. | |
| 2005/0281811 A1 | 12/2005 | Browning et al. | |
| 2006/0104971 A1 | 5/2006 | Garber et al. | |
| 2006/0134102 A1 | 6/2006 | LePage et al. | |
| 2006/0222644 A1 | 10/2006 | Garber et al. | |
| 2006/0280722 A1 | 12/2006 | Browning et al. | |
| 2007/0154476 A1 | 7/2007 | Browning et al. | |

FOREIGN PATENT DOCUMENTS

| | | |
|---|---|---|
| EP | 0509553 B1 | 10/1992 |
| EP | 0519596 B1 | 12/1992 |
| WO | WO-89/07142 A1 | 8/1989 |
| WO | WO-91/09967 A1 | 7/1991 |
| WO | WO-92/00329 A1 | 1/1992 |
| WO | WO-94/04679 A1 | 3/1994 |
| WO | WO-94/09817 A1 | 5/1994 |
| WO | WO-94/13808 A2 | 6/1994 |
| WO | WO-94/13808 A3 | 6/1994 |
| WO | WO-94/20625 A1 | 9/1994 |
| WO | WO-95/09917 A1 | 4/1995 |
| WO | WO-95/22389 | 8/1995 |
| WO | WO-96/22788 A1 | 8/1996 |
| WO | WO-97/03687 A1 | 2/1997 |
| WO | WO-97/11370 | 3/1997 |
| WO | WO-99/15549 A2 | 4/1999 |
| WO | WO-99/38525 A1 | 8/1999 |
| WO | WO-99/58679 A1 | 11/1999 |
| WO | WO-02/30986 A2 | 4/2002 |
| WO | WO-02/060955 A2 | 8/2002 |
| WO | WO-02/066516 A2 | 8/2002 |
| WO | WO-02/085946 A1 | 10/2002 |
| WO | WO-02/088170 A2 | 11/2002 |
| WO | WO-02/096948 A2 | 12/2002 |
| WO | WO-2004/026427 A2 | 4/2004 |
| WO | WO-2004/029207 A2 | 4/2004 |
| WO | WO-2004/042017 A2 | 5/2004 |
| WO | WO-2004/074434 A2 | 9/2004 |
| WO | WO-2005/000899 A2 | 1/2005 |
| WO | WO-2005/092927 A1 | 10/2005 |

OTHER PUBLICATIONS

Alderson, Mark R. et al., "Regulation of apoptosis and T cell activation by Fas-specific mAb," *International Immunology*, vol. 6(11):1799-1806 (1994).

Alimzhanov, Marat B. et al., "Abnormal development of secondary lymphoid tissues in lymphotoxin β-deficient mice," *Proc. Natl. Acad. Sci. USA*, vol. 94:9302-9307 (1997).

Alt, Margitta, et al., "Novel tetravalent and bispecific IgG-like antibody molecules combining single-chain diabodies with the immunoglobulin γl Fc or CH3 region," *FEBS Letters*, vol. 454:90-94 (1999).

Androlewicz, Matthew J. et al., "Lymphotoxin Is Expressed as a Heteromeric Complex with a Distinct 33-kDa Glycoprotein on the surface of an Activated Human T Cell Hybridoma," *The Journal of Biological Chemistry*, vol. 267(4):2542-2547 (1992).

Angal, S., et al. "A Single Amino Acid Substitution Abolishes the Heterogeneity of Chimeric Mouse/Human (IgG4) Antibody." *Molecular Immunology*. 1993; 30(1):105-8.

Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," *J. Exp. Med.*, vol. 177:1439-1450 (1993).

Baens, Mathus et al., "Construction and Evaluation of a hncDNA Library of Human 12p Transcribed Sequences Derived from a Somatic Cell Hybrid," *Genomics*, vol. 16:214-218 (1993).

Banks, Theresa A. et al., "Lymphotoxin-α-Deficient Mice," *The Journal of Immunology*, vol. 155:1685-1693 (1995).

Benhar, Itai, et al., "*Pseudomonas* Exotoxin A Mutants," *The Journal of Biological Chemistry*, vol. 269(18):13398-13404 (1994).

Bera, Tapan K., et al., "A Bivalent Disulfide-stabilized Fv with Improved Antigen Binding to erbB2," *J. Mol. Biol.*, vol. 281:475-483 (1998).

Bernstein, David I. et al., "Effects of therapy with an immunomodulator (imiquimod, R-837) alone and with acyclovir on genital HSV-2 infection in guinea-pigs when begun after lesion development," *Antiviral Research*, vol. 20:45-55 (1993).

Bloom, James W., et al., "Interchain disulfide bond in the core hinge region of human IgG4," *Protein Science*, vol. 6:407-415 (1997).

Bowie, James U. et al., "Deciphering the Message in Protein Sequences: Tolerance to Amino Acid Substitutions," *Science*, vol. 247:1306-1310 (1990).

Brekke, Ole Henrik et al, "The structural requirements for complement activation by IgG: does it hinge on the hinge?" *Immunology Today*, vol. 16(2):85-90 (1995).

Briskin, Michael J. et al., "MAdCAM-1 has homology to immunogobulin and mucin-like adhesion receptors and to IgA1," *Nature*, vol. 363:461-464 (1993).

Browning, Jeffrey L. et al., "Characterization of Surface Lymphotoxin Forms, Use of Specific Monoclonal Antibodies and Soluble Receptors," *The Journal of Immunology*, vol. 154:33-46 (1995).

Browning, Jeffrey L. et al., "Lymphotoxin and an Associated 33-kDa Glycoprotein are Expressed on the Surface of an Activated Human T Cell Hybridoma," *The Journal of Immunology*, vol. 147(4):1230-1237 (1991).

Browning, Jeffrey L. et al., "Lymphotoxin β, a Novel Member of the TNF Family That Forms a Heteromeric Complex with Lymphotoxin on the Cell Surface," *Cell*, vol. 72:847-856 (1993).

Browning, Jeffrey L. et al., "Signaling through the Lymphotoxin β Receptor Induces the Death of Some Adenocarcinoma Tumor Lines," *J. Exp. Med.*, vol. 183:867-878 (1996).

Browning, Jeffrey L. et al., "Signaling through the lymphotoxin-β receptor in conjunction with interferon-γ induces the death of A human tumor line," *The 9th International Congress of Immunology*, No. 4582 (1995).

Browning, Jeffrey L. et al., "Studies on the Differing Effects of Tumor Necrosis Factor and Lymphotoxin on the Growth of Several Human Tumor Lines," *The Journal of Immunology*, vol. 143(6):1859-1867 (1989).

Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, vol. 111:2129-2138 (1990).

Campbell, Neil A. et al., "Methods: Monoclonal Antibody Technology," Biology, 5th Edition, Unit Seven, Animal Form and Function, Benjamin/Cummings, Laura Kennedy Ed., p. 856 (1999).

Caron, P.C., et al. "Engineered Humanized Dimeric Forms of IgG Are More Effective Antibodies." *J. Exp. Med.* Oct. 1992; 176:1191-95.

Carter, Paul, et al., "Engineering antibodies for imaging and therapy," *Current Opinion in Biotechnology*, vol. 8:449-454 (1997).

Cavert, Winston et al., "Kinetics of Response in Lymphoid Tissues to Antiretroviral Therapy of HIV-1 Infection," *Science*, vol. 276:960-964 (1997).

Chen, Chyi-Ying A. et al., "AU-rich elements: characterization and importance in mRNA degradation," *TIBS*, vol. 20:465-470 (1995).

Cher, Daniel J. et al., "Two Types of Murine Helper T Cell Clone. II. Delayed-Type Hypersensitivity is Mediated by $T_H1$ Clones," *The Journal of Immunology*, vol. 138(11):3688-3694 (1987).

Chintalacharuvu, Koteswara R., et al., "Cysteine Residues Required for the Attachment of the Light Chain in Human IgA2[1]," *The Journal of Immunology*, vol. 169:5072-5077 (2002).

Chintalacharuvu, Koteswara R., et al., "Hybrid IgA2/IgG1 Antibodies with Tailor-Made Effector Functions," *Clinical Immunology*, vol. 101(1):21-31 (2001).

Chintalacharuvu, Koteswara R., et al., "Production and characterization of recombinant IgA," *Immunotechnology*, vol. 4:165-174 (1999).

Chintalacharuvu, Koteswara R., et al., "Residues Critical for H-L Disulfide Bond Formation in Human IgA1 and IgA2[1]," *The Journal of Immunology*, vol. 157:3443-3449 (1996).

Chisholm, Patricia L. et al., "Monoclonal antibodies to the integrin α-4 subunit inhibit the murine contact hypersensitivity response," *Eur. J. Immunol.*, vol. 23:682-688 (1993).

Co, Man Sung et al., "Humanized antibodies for therapy," *Nature*, vol. 351:501-502 (1991).

Colman, P.M., "Effects of amino acid sequence changes on antibody-antigen interactions," *Research in Immunology*, vol. 145:33-36 (1994).

Coloma, M. Josefina et al, "Design and production of novel tetravalent bispecific antibodies," *Nature Biotechnology*, vol. 15:159-163 (1997).

Coloma, M.J., et al. "The Hinge as a Spacer Contributes to Covalent Assembly and is Required for Function of IgG[1]." *The Journal of Immunology*. 1997; 158:733-40.

Couto, Joseph R. et al., "Humanization of KC4G3, an Anti-Human Carcinoma Antibody," *Hybridoma*, vol. 13(3):215-219 (1994).

Crowe, Paul D. et al., "A Lymphotoxin-β-Specific Receptor," *Science*, vol. 264:707-710 (1994).

Crowe, Paul D. et al., "Production of lymphotoxin (LTα) and a soluble dimeric form of its receptor using the baculovirus expression system," *Journal of Immunological Methods*, vol. 168:79-89 (1994).

de Kruif, J., et al. "Leucine Zipper Dimerized Bivalent and Bispecific scFv Antibodies from a Semi-synthetic Antigody Phage Display Library." *The Journal of Biological Chemistry*. Mar. 29, 1996; 271(13):7630-34.

De Togni, Pietroet al., "Abnormal Development of Peripheral Lymphoid Organs in Mice Deficient in Lymphotoxin," *Science*, vol. 264:703-707 (1994).

Dhein, Jens et al., "Induction of Apoptosis by Monoclonal Antibody Anti-Apo-1 Class Switch Variants is Dependent on Cross-Linking of APO-1 Cell Surface Antigens," *The Journal of Immunology*, vol. 149(10):3166-3173 (1992).

Dighe, Anand S. et al., "Enhanced In Vivo Growth and Resistance to Rejection of Tumor Cells Expressing Dominant Negative IFNγ Receptors," *Immunity*, vol. 1:447-456 (1994).

Dijkstra, Christine D. et al., "Marginal zone macrophage identified by a monoclonal antibody: characterization of immuno- and enzyme-histochemical properties and functional capacities," *Immunology*, vol. 55:23-30 (1985).

Dorai, Haimanti, et al., "Role of Inter-heavy and Light Chain Disulfide Bonds in the Effector Functions of Human Immunoglobulin IgG1," *Molecular Immunology*, vol. 29(12):1487-1491 (1992).

Düzgünes, Nejat et al., "Liposome Targeting to HIV-Infected Cells via Recombinant Soluble CD4 and CD4-IgG (Immunoadhesin)," *Journal of Cellular Biochemistry*, p. 77, No. Q514 (1992).

Endres, Robert et al., "Mature Follicular Dendritic Cell Networks Depend on Expression of Lymphotoxin β Receptor by Radioresistant Stromal Cells and of Lymphotoxin β and Tumor Necrosis Factor by B Cells," *J. Exp. Med.*, vol. 189(1):159-167 (1999).

Eppstein, Deborah A. et al., "Biological activity of liposome-encapsulated murine interferon γ is mediated by a cell membrane receptor," *Proc. Natl. Acad. Sci. USA*, vol. 82:3688-3692 (1985).

Erickson, Sharon L. et al., "Decreased sensitivity to tumour-necrosis factor but normal T-cell development in TNF receptor-2-deficient mice," *Nature*, vol. 372:560-563 (1994).

Ettinger, Rachel et al., "Disrupted splenic architecture, but normal lymph node development in mice expressing a soluble lymphotoxin-β receptor-IgG1 fusion protein," *Proc. Natl. Acad. Sci. USA*, vol. 93:13102-13107 (1996).

Fägerstam, Lars G. et al., "Surface Plasmon Resonance Detection in Affinity Technologies," *Handbook of Affinity Chromatography*, Toni Kline, Ed., Marcel Dekker, Inc., Chpt. 9, pp. 229-252 (1993).

Fitch, F.W. et al., "Differential Regulation of Murine Lymphocyte Subsets," *Annu. Rev. Immunol.*, vol. 11:29-48 (1993).

FitzGerald, Kevin, et al., "Improved tumour targeting by disulphide stabilized diabodies expressed in *Pichia pastoris*," *Protein Engineering*, vol. 10(10):1221-1225 (1997).

Foote, Jefferson et al., "Antibody Framework Residues Affecting the Conformation of the Hypervariable Loops," *J. Mol. Biol.*, vol. 224:487-499 (1992).

Force, Walker R. et al., "Mouse Lymphotoxin-β Receptor," *The Journal of Immunology*, vol. 155:5280-5288 (1995).

Foy, Teresa M. et al., "gp39-CD40 Interactions Are Essential for Germinal Center Formation and the Development of B Cell Memory," *J. Exp. Med.*, vol. 180:157-163 (1994).

Fu, Yang-Xin et al., "B Lymphocytes Induce the Formation of Follicular Dendritic Cell Clusters in a Lymphotoxin α-dependent Fashion," *J. Exp. Med.*, vol. 187(7):1009-1018 (1998).

Fu, Yang-Xin et al., "Development and Maturation of Secondary Lymphoid Tissues," *Annu. Rev. Immunol.*, vol. 17:399-433 (1999).

Fu, Yang-Xin et al., "Lymphotoxin-α (LTα) Supports Development of Splenic Follicular Structure That Is Required for IgG Responses," *J. Exp. Med.*, vol. 185(12):2111-2120 (1997).

Fukushima, Keiko et al., "N-Linked Sugar Chain Structure of Recombinant Human Lymphotoxin Produced by CHO Cells: The Functional Role of Carbohydrate as to Its Lectin-like Character and Clearance Velocity," *Archives of Biochemistry and Biophysics*, vol. 304(1):144-153 (1993).

Fütterer, Agnes et al., "The Lymphotoxin β Receptor Controls Organogenesis and Affinity Maturation in Peripheral Lymphoid Tissues," *Immunity*, vol. 9:59-70 (1998).

Gillies, Stephen D., et al., "Antigen binding and biological activities of engineered mutant chimeric antibodies with human tumor specificities," *Hum. Antibod. Hybridomas*, vol. 1(1):47-54 (1990).

Glockshuber, Rudi, et al., "A Comparison of Strategies To Stabilize Immunoglobulin $F_v$-Fragments," *Biochemistry*, vol. 29:1362-1367 (1990).

Gommerman, Jennifer L. et al., "Lymphotoxin/Light, Lymphoid Microenvironments and Autoimmune Disease," *Nature Reviews Immunology*, vol. 3:642-655 (2003).

Gonzalez, Mercedes et al., "The Sequential Role of Lymphotoxin and B Cells in the Development of Splenic Follicles," *J. Exp. Med.*, 187:997-1007 (1998).

Goodwin, Raymond G. et al., "Molecular and Biological Characterization of a Ligand for CD27 Defines a New Family of Cytokines with Homology to Tumor Necrosis Factor," *Cell*, vol. 73:447-456 (1993).

Guan, Lufeng, et al., "Homogeneous immunoconjugates for boron neutron-capture therapy: Design, synthesis, and preliminary characterization," *Proc. Natl. Acad. Sci. USA*, vol. 95:13206-13210 (1998).

Györfy, Zs. et al., "Alteration of the TNF Sensitivity and Membrane Viscosity of Target Cells," *Eur. Cytokine Netw.*, vol. 7(2):167 (1996).

Han, Shuhua et al., "Cellular Interaction in Germinal Centers, Roles of CD40 Ligand and B7-2 in Established Germinal Centers," *The Journal of Immunology*, vol. 155:556-567 (1995).

Haran, G., et al., "Doman motions in phosphoglycerate kinase: Determination of interdomain distance distributions by site-specific labeling and time-resolved fluorescence energy transfer," *Proc. Natl. Acad. Sci. USA*, vol. 89:11764-11768 (1992).

Havell, Edward A. et al., "The Antitumor Function of Tumor Necrosis Factor (TNF), I. Therapeutic Action of TNF against an Established Murine Sarcoma Is Indirect, Immunologically Dependent, and Limited by Severe Toxicity," *J. Exp. Med.*, vol. 167:1067-1085 (1988).

Heath, Sonya L. et al., "Follicular dendritic cells and human immunodeficiency virus infectivity," *Nature*, vol. 377:740-744 (1995).

Hipp, Jason D. et al., "Cancer Vaccines: An Update," *In Vivo*, vol. 14:571-585 (2000).

Hu, S., et al. "Minibody: A Novel Engineered Anti-Carcinoembryonic Antigen Antibody Fragment (Single-Chain Fv- $C_H3$) Which Exhibits Rapid, High-Level Targeting of Xenografts." *Cancer Research.* Jul. 1, 1996; 56:3055-61.

Huang, Sui et al., "Immune Response in Mice That Lack the Interferon-γ Receptor," *Science*, vol. 259:1742-1745 (1993).

Hudson, Peter J., "Recombinant antibody constructs in cancer therapy," *Current Opinion in Immunology*, vol. 11:548-557 (1999).

Humphreys, David P., et al., "F(ab')2 molecules made from *Escherichia coli* produced Fab' with hinge sequences conferring increased serum survival in an animal model," *Journal of immunological Methods*, vol. 217:1-10 (1998).

Hwang, Karl J. et al., "Hepatic uptake and degradation of unilamellar sphingomyelin/cholesterol liposomes: A kinetic study," *Proc. Natl. Acad. Sci. USA*, vol. 77(7):4030-4034 (1980).

Inouye, K., et al. "Single-step purification of F(ab')$_{2u}$fragments of mouse monoclonal antibodies (immunoglobulins M) by hydrophobic ingteraction high-performance liquid chromatography using TSKgel Ether-5PW." *Journal of Biochemical and Biophysical Methods.* 1993; 26:27-39.

Jain, Rakesh K., "Vascular and interstitial barriers to delivery of therapeutic agents in tumors," *Cancer and Metastasis Reviews*, vol. 9:253-266 (1990).

Jendreyko, Nina et al, "Intradiabodies, Bispecific, Tetravalent Antibodies for the Simultaneous Functional Knockout of Two Cell Surface Receptors," *The Journal of Biological Chemistry*, vol. 278(48):47812-47819 (2003).

Johne, Berit et al., "Epitope mapping and binding kinetics of monoclonal antibodies studied by real time biospecific interaction analysis using surface plasmon resonance," *Journal of Immunological Methods*, vol. 160:191-198 (1993).

Jue, Rodney, et al., "Addition of Sulfhydryl Groups to *Escherichia coli* Ribosomes by Protein Modification with 2-Iminothiolane (Methyl 4-Mercaptobutyrimidate)," *Biochemistry*, vol. 17(25):5399-5406 (1978).

Jurásková, Vera et al., "Interferon inducer, polyriboguanylic—polyribocytidylic acid, inhibits experimental hepatic metastases in mice," *European Journal of Pharmacology*, vol. 221:107-111 (1992).

Katz, Jonathan D. et al., "T Helper Cell Subsets in Insulin-Dependent Diabetes," *Science*, vol. 268:1185-1188 (1995).

Kawabe, Tsutomu et al., "The Immune Responses in CD40-Deficient Mice: Impaired Immunoglobulin Class Switching and Germinal Center Formation," *Immunity*, vol. 1:167-178 (1994).

Kipriyanov, Sergey M., et al., "Bacterial Expression and Refolding of Single-Chain Fv Fragments with C-Terminal Cysteines," *Cell Biophysics*, vol. 26:187-204 (1995).

Kohno, Tadahiko et al., "A second tumor necrosis factor receptor gene product can shed a naturally occurring tumor necrosis factor inhibitor," *Proc. Natl. Acad. Sci. USA*, vol. 87:8331-8335 (1990).

Kolanus, Waldemar et al., "T Cell Activation by Clustered Tyrosine Kinases," *Cell*, vol. 74:171-183 (1993).

Kolbinger, Frank et al., "Humanization of a mouse anti-human IgE antibody: a potential therapeutic for IgE-mediated allergies," *Protein Engineering*, vol. 6(8):971-980 (1993).

Kopp, William C. et al., "Immunomodulatory Effects of Interferon-γ in Patients with Metastatic Malignant Melanoma," *Journal of Immunotherapy*, vol. 13(3):181-190 (1993).

Kraal, Georg, "Cells in the Marginal Zone of the Spleen," *International Review of Cytology*, vol. 132:31-74 (1992).

Kraal, Georg et al., "Expression of the Mucosal Vascular Addressin, MAdCAM-1, on Sinus-Lining Cells in the Spleen," *American Journal of Pathology*, vol. 147(3):763-771 (1995).

Kraal, G. et al., "Lymphocyte migration in the spleen: the effect of macrophage elimination," *Immunology*, vol. 68:227-232 (1989).

Kraal, G. et al., "Marginal metallophilic cells of the mouse spleen identified by a monoclonal antibody," *Immunology*, vol. 58:665-669 (1986).

Kratz, Alexander et al., "Chronic Inflammation Caused by Lymphotoxin Is Lymphoid Neogenesis," *J. Exp. Med.*, vol. 183:1461-1472 (1996).

Kreitman, Robert J. et al., "Immunotoxins for targeted cancer therapy," *Advanced Drug Delivery Reviews*, vol. 31:53-88 (1998).

Kreitman, Robert J., et al., "Site-Specific Conjugation to Interleukin 4 Containing Mutated Cysteine Residues Produces Interleukin 4-Toxin Conjugates with Improved Binding and Activity," *Biochemistry*, vol. 33:11637-11644 (1994).

Laman, Jon D. et al., "Functions of CD40 and Its Ligand, gp39 (CD40L)," *Critical Reviews in Immunology*, vol. 16:59-108 (1996).

Lane, Peter et al., "Activated human T cells express a ligand for the human B cell-associated antigen CD40 which participates in T cell-dependent activation of B lymphocytes," *Eur. J. Immunol.*, vol. 22:2573-2578 (1992).

Langer, Robert et al., "Biocompatibility of polymeric delivery systems for macromolecules," *Journal of Biomedical Materials Research*, vol. 15:267-277 (1981).

Langer, Robert, "Controlled release of macromolecules," *Chemtech*, pp. 98-105 (1982).

Lawton, Pornsri et al., "Characterization of the Mouse Lymphotoxin-β Gene," *The Journal of Immunology*, vol. 154:239-246 (1995).

Lazar, Eliane et al., "Transforming Growth Factor α: Mutation of Aspartic Acid 47 and Leucine 48 Results in Different Biological Activities," *Molecular and Cellular Biology*, vol. 8(3):1247-1252 (1988).

Le Hir, Michel et al., "Differentiation of Follicular Dendritic Cells and Full Antibody Responses Require Tumor Necrosis Factor Receptor-1 Signaling," *J. Exp. Med.*, vol. 183:2367-2372 (1996).

Lee, C.V., et al. "Bivalent antibody phage display mimics natural immunoglobulin." *Journal of Immunological Methods.* 2004; 284:119-32.

Lee, Hyun-Sil, et al., "Generation and characterization of a novel single-gene-encoded single-chain immunoglobulin molecule with antigen binding activity and effector functions," *Molecular Immunology*, vol. 36:61-71 (1999).

Leung, Shui-on et al, "The Effects of Domain Deletion, Glycosylation, and Long IgG, Hinge on the Biodistribution and Serum Stability Properties of a Humanized IgG, Immunoglobulin, hLL2, and Its Fragments," *Clinical Cancer Research*, vol. S:3106s-3116s (1999).

Ling, Leona E. et al., "Human Type I Interferon Receptor, IFNAR, Is a Heavily Glycosylated 120-130 kD Membrane Protein," *Journal of Interferon and Cytokine Research*, vol. 15:55-61 (1995).

Loetscher, Hansruedi et al., "Recombinant 55-kDa Tumor Necrosis Factor (TNF) Receptor," *The Journal of Biological Chemistry*, vol. 266(27:18324-18329 (1991).

Lu, Dan et al, "Di-diabody: a novel tetravalent bispecific antibody molecule by design," *Journal of Immunological Methods*, vol. 279:219-232 (2003).

Lund, J., et al. "Multiple Interactions of IgG with Its Core Oligosaccharide Can Modulate Recognition by Complement and Human Fcγ Receptor I and Influence the Synthesis of Its Oligosacharide Chains." *The Journal of Immunology.* 1996; 157:4963-69.

Lyons, Alan, et al., "Site-specific attachment to recombinant antibodies via introduced surface cysteine residues," *Protein Engineering*, vol. 3(8):703-708 (1990).

Mackay, Fabienne et al., "Lymphotoxin but not tumor necrosis factor functions to maintain splenic architecture and humoral responsiveness in adult mice," *Eur. J. Immunol.*, vol. 27:2033-2042 (1997).

Mackay, Fabienne et al., "Turning off follicular dendritic cells," *Nature*, vol. 395:26-27 (1998).

MacLennan, I.C.M., "2:The Structure and Function of Secondary Lymphoid Tissues," *Clinical Aspects of Immunology, Fifth Edition*, vol. 1, Blackwell Scientific Publications, P.J. Lachmann, Ed., Chpt. 2, pp. 13-30 (1993).

Maeda, Kunihiko et al., "Murine Follicular Dendritic Cells and Low Affinity Fc Receptors for IgE (FcεRII)," *The Journal of Immunology*, vol. 148(8):2340-2347 (1992).

Matsumoto, Mitsuru et al., "Affinity maturation without germinal centres in lymphotoxin-α-deficient mice," *Nature*, vol. 382:462-466 (1996).

Matsumoto, Mitsuru et al., "Distinct Roles of Lymphotoxin α and the Type I Tumor Necrosis Factor (TNF) Receptor in the Establishment of Follicular Dendritic Cells from Non-Bone Marrow-derived Cells," *J. Exp. Med.*, vol. 186(12):1997-2004 (1997).

Matsumoto, Mitsuru et al., "Lymphotoxin-α-deficient and TNF receptor-I-deficient mice define development and functional characteristics of germinal centers," *Immunological Reviews*, vol. 156:137-144 (1997).

Matsumoto, Mitsuru et al., "Role of Lymphotoxin and the Type I TNF Receptor in the Formation of Germinal Centers," *Science*, vol. 271:1289-1291 (1996).

Mendlovic, Shlomo et al., "Induction of a systemic lupus erythematosus-like disease in mice by a common human anti-DNA idiotype," *Proc. Natl. Acad. Sci. USA*, vol. 85:2260-2264 (1988).

Michaelsen, T.E., et al. "Antibody Dependent Cell-Mediated Cytotoxicity Induced by Chimeric Mouse-Human IgG Subclasses and IgG3 Antibodies with Altered Hinge Region." *Molecular Immunology*. 1992; 29(3):319-26.

Miller, Glenn T. et al., "Specific Interaction of Lymphocyte Function-associated Antigen 3 with CD2 Can Inhibit T Cell Responses," *J. Exp. Med.*, vol. 178:211-222 (1993).

Modlin, Robert L. et al., "Type 2 cytokines and negative immune regulation in human infections," *Current Opinion in Immunology*, vol. 5:511-517 (1993).

Mohan, Chandra et al., "Interaction Between CD40 and Its Ligand p. 39 in the Development of Murine Lupus Nephritis," *The Journal of Immunology*, vol. 154:1470-1480 (1995).

Mohler, Kendall M. et al., "Soluble Tumor Necrosis Factor (TNF) Receptors Are Effective Therapeutic Agents in Lethal Endotoxemia and Function Simultaneously as Both TNF Carriers and TNF Antagonists," *The Journal of Immunology*, vol. 151(3):1548-1561 (1993).

Morimoto, K., et al. "Method for the preparation of bispecific F(ab')2μ fragments from mouse monoclonal antibodies of the immunoglobulin M class and characterization of the fragments." *Journal of Immunological Methods*. 1999; 224:43-50.

Morimoto, K., et al. "Single-step purification of F(ab')$_2$ fragments of mouse monoclonal antibodies (immunoglobulins G1) by hydrophobic interaction high performance liquid chromatography using TSKgel Phenyl-5PW." *Journal of Biochemical and Biophysical Methods*. 1992; 24:107-17.

Morrison, Sherie L. et al., "Chimeric human antibody molecules: Mouse antigen-binding domains with human constant region domains," *Proc. Natl. Acad. Sci. USA*, vol. 81:6851-6855 (1984).

Morrison, Sherie L., "In Vitro Antibodies, Strategies for Production and Application," *Ann. Rev. Immunol.*, vol. 10:239-265 (1992).

Morrissey, Philip J. et al., "CD4$^+$ T Cells That Express High Levels of CD45RB Induce Wasting Disease When Transferred into Congenic Severe Combined Immunodeficient Mice. Disease Development Is Prevented by Cotransfer of Purified CD4$^+$ T Cells," *J. Exp. Med.*, vol. 178:237-244 (1993).

Muppidi, J.R. et al., "Ligand-independent redistribution of Fas (CD95) into lipid rafts mediates clonotypic T cell death," *Nature Immunology*, vol. 5(2):182-189 (2004).

Nakache, Maurice et al., "The mucosal vascular addressin is a tissue-specific endothelial cell adhesion molecule for circulating lymphocytes," *Nature*, vol. 337:179-181 (1989).

Neumann, Brigitte et al., "Defective Peyer's Patch Organogenesis in Mice Lacking the 55-kD Receptor for Tumor Necrosis Factor," *J. Exp. Med.*, vol. 184:259-264 (1996).

Niederle, Norbert et al., "Long-Term Treatment of Chronic Myelogenous Leukemia with Different Interferons: Results from Three Studies," *Leukemia and Lymphoma*, vol. 9:111-119 (1993).

Norderhaug, L., et al. "Chimeric mouse human IgG3 antibodies with an IgG4-like hinge region induce complement-mediated lysis more efficiently than IgG3 with normal hinge." *Eur. J. Immunol.* 1991; 21:2379-84.

Olafsen, Tove, et al., "Covalent disulfide-linked anti-CEA diabody allows site-specific conjugation and radiolabeling for tumor targeting applications," *Protein Engineering, Design & Selection*, vol. 17(1):21-27 (2004).

Onishi, Tetsuro et al., "A Study on Direct Antitumor Activity of Bropirimine (Oral Interferon Inducer) for Renal Cell Carcinoma," *Acta Urol. Jpn.*, vol. 40:195-200 (1994).

Palmer, Michael, et al., "*Staphylococcus aureus* α-Toxin," *The Journal of Biological Chemistry*, vol. 268(16):11959-11962 (1993).

Paul, William E., "Immunogenicity and Antigen Structure," Fundamental Immunology, Third Edition, Raven Press, Chpt. 8, p. 242, Chpt. 9, pp. 292-295 (1993).

Pfeffer, Klaus et al., "Mice Deficient for the 55 kd Tumor Necrosis Factor Receptor Are Resistant to Endotoxic Shock, yet Succumb to L. monocytogenes Infection," *Cell*, vol. 73:457-467 (1993).

Picarella, Dominic E. et al., "Insulitis in transgenic mice expressing tumor necrosis factor β (lymphotoxin) in the pancreas," *Proc. Natl. Acad. Sci. USA*, vol. 89:10036-10040 (1992).

Picker, Louis J. et al., "Physiological and Molecular Mechanisms of Lymphocyte Homing," *Annu. Rev. Immunol.*, vol. 10:561-591 (1992).

Pleskov, V.M. et al., "The receptor-mediated endocytosis of influenza viruses and low-density lipoproteins by tissue cells," *Vopr. Virusol.*, vol. 39(3):121-125 (1994).

Plückthun, Andreas et al, "New protein engineering approaches to multivalent and bispecific antibody fragments," *Immunotechnology*, vol. 3:83-105 (1997).

Powell, Kenneth L. et al., "The antiviral effects of nitric oxide," *Trends in Microbiology*, vol. 3(3):81-88 (1995).

Powrie, Fiona et al., "Inhibition of Th1 Responses Prevents Inflammatory Bowel Disease in *scid* Mice Reconstituted with CD45RB$^{hi}$ CD4$^+$ T Cells," *Immunity*, vol. 1:553-562 (1994).

Powrie, Fiona et al., "Phenotypically distinct subsets of CD4$^+$ T cells induce or protect from chronic intestinal inflammation in C. B-17 *scid* mice," *International Immunity*, vol. 5(11):1461-1471 (1993).

Queen, Cary et al., "A humanized antibody that binds to the interleukin 2 receptor," *Proc. Natl. Acad. Sci. USA*, vol. 86:10029-10033 (1989).

Queiroz, J.A., et al., "Hydrophobic interaction chromatography of proteins," *Journal of Biotechnology*, vol. 87:143-159 (2001).

Raitano, Arthur B. et al., "Tumor Necrosis Factor Up-regulates γ-Interferon Binding in a Human Carcinoma Cell Line," *The Journal of Biological Chemistry*, vol. 265(18):10466-10472 (1990).

Reed, Steven G. et al., "T-cell and cytokine responses in leishmaniasis," *Current Opinion in Immunobiology*, vol. 5:524-531 (1993).

Reff, Mitchell E., et al., "A review of modifications to recombinant antibodies: attempt to increase efficacy in oncology applications," *Critical Reviews in Oncology/Hematology*, vol. 40:25-35 (2001).

Reiter, Yoram, et al., "Engineering interchain disulfide bonds into conserved framework regions of Fv Fragments: improved biochemical characteristics of recombinant immunotoxins containing disulfide-stabilized Fv," *Protein Engineering*, vol. 7(5):697-704 (1994).

Rennert, P.D. et al., "Normal Development of Lymph Nodes is Disrupted by Soluble LT beta Receptor—Ig Fusion Protein," *Eur. Cytokine Netw.*, vol. 7(2):167 (1996).

Rennert, Paul D. et al., "Surface Lymphotoxin α/β Complex Is Required for the Development of Peripheral Lymphoid Organs," *J. Exp. Med.*, vol. 184:1999-2006 (1996).

Renshaw, Blair R. et al., "Humoral Immune Responses in CD40 Ligand-deficient Mice," *J. Exp. Med.*, vol. 1994:1889-1900 (1994).

Reutershealth.com, "What is Systemic Erythematosus?" retrieved online at http://www.reutershealth.com/wellconnected/doc/63.html (2004).

Riechmann, Lutz et al., "Reshaping human antibodies for therapy," *Nature*, vol. 332:323-327 (1988).

Roitt, Ivan M. et al., Immunology, Third Edition, Mosby, Chpt. 1, pp. 1.1-1.12, Chpts. 19-22, pp. 19.1-22.12 (1993).

Romagnani, Sergio, "Lymphokine Production by Human T Cells in Disease States," *Annu. Rev. Immunol.*, vol. 12:227-257 (1994).

Rothe, Joachim et al., "Mice lacking the tumour necrosis factor receptor 1 are resistant to TNF-mediated toxicity but highly susceptible to infection by *Listeria monocytogenes*," *Nature*, vol. 364:798-802 (1993).

Roux, K.H., et al. "Comparisons of the Ability of Human IgG3 Hinge Mutants, IgM, IgE, and IgA2, to Form Small Immune Complexes: A Role for Flexibility and Geometry." *The Journal of Immunology.* 1998; 161:4083-90.

Ruddle, Nancy H. et al, "An Antibody to Lymphotoxin and Tumor Necrosis Factor Prevents Transfer of Experimental Allergic Encephalomyelitis," *J. Med. Med.*, vol. 172:1193-1200 (1990).

Rudikoff, Stuart et al., "Single amino acid substitution altering antigen-binding specificity," *Proc. Natl. Acad. Sci. USA*, vol. 79:1979-1983 (1982).

Sayegh, Mohamed H. et al., "CD28-B7 Blockade after Alloantigenic Challenge In Vivo Inhibits Th1 Cytokines but Spares Th2," *J. Exp. Med.*, vol. 181:1869-1874 (1995).

Schiller, Joan H. et al., "Biological and Clinical Effects of Intravenous Tumor Necrosis Factor-α Administered Three Times Weekly," *Cancer Research*, vol. 51:1651-1658 (1991).

Schoenfeld, Hans-Joachim et al., "Efficient Purification of Recombinant Human Tumor Necrosis Factor β from *Escherichia coli* Yields Biologically Active Protein with a Trimeric Structure That Binds to Both Tumor Necrosis Factor Receptors," *The Journal of Biological Chemistry*, vol. 266(6):3863-3869 (1991).

Schriever, Folke et al., "The Central Role of Follicular Dendritic Cells in Lymphoid Tissues," *Advances in Immunology*, vol. 51:243-284 (1992).

Schuurman, J., et al. "The inter-heavy chain disulfide bonds of IgG4 are in equilibrium with intra-chain disulfide bonds." *Molecular Immunology*. 2001; 38:1-8.

Selmaj, Krzysztof et al., "Identification of Lymphotoxin and Tumor Necrosis Factor in Multiple Sclerosis Lesions," *J. Clin. Invest.*, vol. 87:949-954 (1991).

Shopes, Bob, "A Genetically Engineered Human IgG Mutant with Enhanced Cytolytic Activity," *The Journal of Immunology*, vol. 148(9):2918-2922 (1992).

Shopes, Bob, "A Genetically Engineered Human IgG with Limited Flexibility Fully Initiates Cytolysis via Complement," *Molecular Immunology*, vol. 30(6):603-609 (1993).

Sidman, Kenneth R. et al., "Controlled Release of Macromolecules and Pharmaceuticals from Synthetic Polypeptides Based on Glutamic Acid," *Biopolymers*, vol. 22:547-556 (1983).

Slavin-Chiorini, Dale C., et al., "Biological Properties of Chimeric Domain-deleted Anticarcinoma Immunoglobulin," *Cancer Research*, (Suppl.) vol. 55:5957s-5967s (1995).

Slepushkin, A.N. et al., "A comparative study of live and inactivated influenza vaccines: the organization of the observation and the results of a study of their reactogenicity and immunogenicity," *Vopr. Virusol.*, vol. 39(3):129-131 (1994).

Smith, Craig A. et al., "A Receptor for Tumor Necrosis Factor Defines an Unusual Family of Cellular and Viral Proteins," *Science*, vol. 248:1019-1023 (1990).

Smith, Richard I.F., et al., "Recombinant Polymeric IgG: An Approach to Engineering More Potent Antibodies," *Bio/Technology*, vol. 12:683-688 (1994).

Smith, Craig A. et al., "The TNF Receptor Superfamily of Cellular and Viral Proteins: Activation, Costimulation, and Death," *Cell*, vol. 78:959-962 (1994).

Smolen, Josef S., "Therapy of systemic lupus erythematosus: a look into the future," *Arthritis Res.*, vol. 4(Suppl. 3):S25-S30 (2002).

Tartaglia, Louis A. et al., "Two TNF receptors," *Immunology Today*, vol. 13(5):151-153 (1992).

Tempest, Philip R. et al., "Reshaping a Human Monoclonal Antibody to Inhibit Human Respiratory Syncytial Virus Infection *In Vivo*," *Bio/Technology*, vol. 9:266-271 (1991).

Tew, John G. et al., "Follicular Dendritic Cells as Accessory Cells," *Immunological Reviews*, vol. 117:185-211 (1990).

Tibbetts, Randal S. et al., "Cardiac Antigen-Specific Autoantibody Production is Associated with Cardiomyopathy in *Trypanosoma cruzi*-Infected Mice," *Journal of Immunology*, vol. 152:1493-1499 (1994).

Toeliner, Kai-Michael et al., "Immunoglobulin Switch Transcript Production In Vivo Related to the Site and Time of Antigen-specific B Cell Activation," *J. Exp. Med.*, vol. 183:2303-2312 (1996).

Traunecker, André et al., "Highly efficient neutralization of HIV with recombinant CD4-immunoglobulin molecules," *Nature*, vol. 339:68-70 (1989).

Trethewey, Pat, "Systemic Lupus Erythematosus," *Dimens. Crit. Care Nurs.*, vol. 23(3):111-115 (2004).

Tsutsumi, Yasuo, et al., "Site-specific chemical modification with polyethylene glycol of recombinant immunotoxin anti-Tac(Fv)-PE38 (LMB-2) improves antitumor activity and reduces animal toxicity and immunogenicity," *PNAS*, vol. 97(15):8548-8553 (2000).

Ullrich, Axel et al., "Signal Transduction by Receptors with Tyrosine Kinase Activity," *Cell*, vol. 61:203-212 (1990).

Van Dullemen, Hendrik M. et al., "Treatment of Crohn's Disease With Anti-Tumor Necrosis Factor Chimeric Monoclonal Antibody (cA2)," *Gastroenterology*, vol. 109:129-135 (1995).

Van Kooten, Cees et al., "CD40-CD40 Ligand: A Multifunctional Receptor—Ligand Pair," *Advances in Immunology*, vol. 61:1-77 (1996).

Van Vliet, Els et al., "Reticular Fibroblasts in Peripheral Lymphoid Organs Identified by a Monoclonal Antibody," *The Journal of Histochemistry and Cytochemistry*, vol. 34(7):883-890 (1986).

Ware, C.F. et al., "The Ligands and Receptors of the Lymphotoxin System," *Pathways for Cytolysis, Current Topics Microbiol. Immunol.*, pp. 175-218 (1995).

Webber, Keith O., et al., "Preparation and Characterization of a Disulfide-Stabilized Fv Fragment of the Anti-Tac Antibody: Comparison with its Single-Chain Analog," *Molecular Immunology*, vol. 32(4):249-258 (1995).

Winter, Greg et al., "Man-made antibodies," *Nature*, vol. 349:293-299 (1991).

Wu, Qiang et al., "The Requirement of Membrane Lymphotoxin for the Presence of Dendritic Cells in Lymphoid Tissues," *J. Exp. Med.*, vol. 190(5):629-638 (1999).

Xu, Jianchao et al., "Mice Deficient for the CD40 Ligand," *Immunity*, vol. 1:423-431 (1994).

Yazaki, Paul J., et al., "Mammalian expression and hollow fiber bioreactor production of recombinant anti-CEA diabody and minibody for clinical applications," *Journal of Immunological Methods*, vol. 253:195-208 (2001).

Yonehara, Shin et al., "A Cell-killing Monoclonal Antibody (Anti-Fas) to a Cell Surface Antigen Co-downregulated with the Receptor of Tumor Necrosis Factor," *J. Exp. Med.*, vol. 169:1747-1756 (1989).

Zhao, Zhan G., et al., "Site-Specific Modification of a Single-Chain Antibody Using a Novel Glyoxylyl-Based Labeling Reagent," *Bioconjugate Chem.*, vol. 10:424-430 (1999).

Zhou, M. et al., "Real-Time Measurements of Kinetics Of EGF Binding to Soluble EGF Receptor Monomers and Dimers Support the Dimerization Model for Receptor Activation," *Biochemistry*, vol. 32:8193-8198 (1993).

Japanese Notice of Reasons for Rejection for Application No. 2006-517785, dated Mar. 26, 2010.

\* cited by examiner

Diagrammatic Representation of the
Two Secreted forms of the Domain Deleted Constructs Bispecific minibody V = Variable
C = Constant
L = Light
H = Heavy
HCP = Hinge Connecting Peptide ) = G₄S flexible linker \ = (G₄S)₄G₃AS flexible linker 2 Anti- LTβR scFvs 2 Anti-TRAIL R2 scFvs

HCP 2 scF v)2 Bispecific Tetravalent minibody
(Bispecific N-s cFv tetravalent minibody)

V = Variable
C = Con stant
L = Light
H = Heavy
HCP = Hing e Connecting Peptide

⟩ = G$_4$S flexible linker

⟩ = (G$_4$S)$_4$G$_3$AS flexible linker

Bispecific diabody

V = Variable
C = Constant
L = Light
H = Heavy
HCP = Hinge Connecting Peptide

= Short linker sc(Fv)2 Tetravalent CH2 Domain-Deleted Bispecific Antibody
(C-scFv Tetravalent CH2 Domain- Deleted Bispecific Antibody)

V = Variable
C = Constant
L = Light
H = Heavy
HCP = Hinge Connecting Peptide
), ↳ = G$_4$S flexible linkers N_H-scFv Tetravalent CH2 Domain-Deleted Bispecific Antibody V = Variable
C = Constant
L = Light
H = Heavy
HCP = Hinge Connecting Peptide ⟩ = $G_4S$ flexible linker ⟨ = $(G_4S)_4G_3AS$ flexible linker V = Variable
C = Constant
L = Light
H = Heavy
HCP = Hinge Connecting Peptide ) = G$_4$S flexible linker \ = (G$_4$S)$_4$G$_3$AS flexible linker

Figure 10A
Single-stranded DNA sequence of heavy chain C-scFv tetravalent CH2 domain-deleted anti-LTBR x anti-TRAIL R2 bispecific antibody gene (anti-LTBR VH – CH1 – G1/G3 hinge – CH3 – linker – anti-TRAIL R2 [VH – linker – VL]) [SEQ ID NO: 25].

```
CAGATCCAGTTGGTGCAGTCTGGACCTGAGCTGAAGAAGCCTGGAGAGACAGTCAAGATC
TCCTGCAAGGCTTCTGGTTTTACCTTCACAGACTATTCAATACACTGGGTGAAACAGGCTC
CAGGAAAGGGTTTAAAGTGGATGGGCTGGATAAACACTGAGACTGGTGAGCCAACATAT
ACAGATGACTTCAAGGGACGATTTGCCTTCTCTTTGGTGACCTCTGCCACCACTGCCTATT
TGCAGATCAACAACCTCAACAATGAGGACACGGCTACATTTTTCTGTGCTAGATTCATCTA
TGATCCTTATTGGGGGTTTGCTTACTGGGGCCAGGGGACTCTGGTCACTGTCTCCGCAGCT
AGCACCAAGGGCCCATCGGTCTTCCCCCTGGCACCCTCCTCCAAGAGCACCTCTGGGGGC
ACAGCGGCCCTGGGCTGCCTGGTCAAGGACTACTTCCCCGAACCGGTGACGGTGTCGTGG
AACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAAAGTTGAGCCCAAA
TCTTGTGACAAAACTCACACATGCCCACCGTGCCCAGAGCCCAAATCTTGTGACACACCTC
CCCCATGCCCACGGTGCCCAGCACCTGGAGGTGGCTCGAGTGGAGGCGGTTCCGGAGGGC
AGCCCCGAGAACCACAGGTGTACACCCTGCCCCCATCCCGGGATGAGCTGACCAAGAACC
AGGTCAGCCTGACCTGCCTGGTCAAAGGCTTCTATCCCAGCGACATCGCCGTGGAGTGGG
AGAGCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGCCTCT
CCCTGTCTCCGGGTTCCGGCGGGGTGGATCCGGTGGAGGGGGCTCCGGCGGTGGCGGGT
CCGAGGTACAACTGGTGGAGTCTGGGGGAGGCTTAGTGAAGCCTGGAGGGTCCCTGAGGC
TCTCCTGTGCAGCCTCTGGATTCACTTTCAGTGACTATTACATGTATTGGTTTCGCCAGGCC
CCGGGAAAGGGGCTGGAGTGGGTCGCAACCATTAGTGATGGTGGTAGTTACACCTACTAT
CCAGACAGTGTGAAGGGGCGATTCACCATCTCCAGAGACAATGCCAAGAACAGCCTCTAC
CTGCAGATGAGCAGCCTGAGGGCTGAGGACACAGCTGTGTATTACTGCGCAAGAGAGGA
GAATGGTAACTTTTACTACTTTGACTACTGGGGCCAAGGGACCACGGTCACCGTCTCCTCT
GGGGGCGGGGGGTCCGGGGGAGGCGGGTCGGGAGGTGGCGGAAGTGATATCCAGATGAC
CCAGTCTCCATCATCCTTGTCTGCATCGGTGGGAGACAGGGTCACTATCACTTGCAAGGCG
GGTCAGGACATTAAAAGCTATTTAAGCTGGTACCAGCAGAAACCAGGGAAAGCGCCTAA
GCTTCTGATCTATTATGCAACAAGGTTGGCAGATGGGGTCCCATCAAGATTCAGTGGCAGT
GGATCTGGTACAGATTATACTCTAACCATCAGCAGCCTGCAGCCTGAGGATTTCGCAACTT
ATTACTGTCTACAGCATGGTGAGAGCCCGTGGACGTTCGGTGGAGGCACCAAGCTGGAGA
TCAAATGA
```

Figure 10B
Amino acid sequence of heavy chain C-scFv tetravalent CH2 domain-deleted anti-LTBR x anti-TRAIL R2 bispecific antibody (anti-LTBR VH – CH1 – G1/G3 hinge – CH3 – linker – anti-TRAIL R2 [VH – linker – VL]) [SEQ ID NO: 26].

```
QIQLVQSGPELKKPGETVKISCKASGFTFTDYSIHWVKQAPGKGLKWMGWINTETGEPTYTDD
FKGRFAFSLVTSATTAYLQINNLNNEDTATFFCARFIYDPYWGFAYWGQGTLVTVSAASTKGP
SVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPEPKSCDTPPPCPRCPAPGGGS
SGGGSGGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGSGGGGSGGGGSGG
GGS
EVQLVESGGGLVKPGGSLRLSCAASGFTFSDYYMYWFRQAPGKGLEWVATISDGGSYTYYPD
SVKGRFTISRDNAKNSLYLQMSSLRAEDTAVYYCAREENGNFYYFDYWGQGTTVTVSSGGG
GSGGGGSGGGGSDIQMTQSPSSLSASVGDRVTITCKAGQDIKSYLSWYQQKPGKAPKLLIYYA
TRLADGVPSRFSGSGSGTDYTLTISSLQPEDFATYYCLQHGESPWTFGGGTKLEIK*
```

Figure 11A

Single-stranded DNA sequence of light chain C-scFv tetravalent CH2 domain-deleted anti-LTBR x anti-TRAIL R2 bispecific antibody (anti-TRAIL R2 VL – kappa constant) [SEQ ID NO: 27].

CAACTTGTGCTCACTCAGTCATCTTCAGTCTCTTTCTCCCTGGGAGCCTCAGCAAAACTCA
CGTGCACCTTGAGTAGTCAGCACAGTACGTACACCATTGAATGGTATCAGCAACAGCCCC
TCAAGCCTCCTAAGTATGTGATGGAGCTTAAGAAAGATGGAAGCCACAGCACAGGTGATG
GGATTCCTGATCGCTTCTCTGGATCCAGCTCTGGTGCTGATCGCTACCTTAGCATTTCCAAC
ATCCAGCCTGAAGATGAAGCAATATACATCTGTGGTGTGGGTGATACAATTAAGGAACAA
TTTGTGTATGTTTTCGGCGGTGGAACCAAGGTCGAAATCAAACGTACGGTGGCTGCACCAT
CTGTCTTCATCTTCCCGCCATCTGATGAGCAGTTGAAATCTGGAACTGCCTCTGTTGTGTGC
CTGCTGAATAACTTCTATCCCAGAGAGGCCAAAGTACAGTGGAAGGTGGATAACGCCCTC
CAATCGGGTAACTCCCAGGAGAGTGTCACAGAGCAGGACAGCAAGGACAGCACCTACAG
CCTCAGCAGCACCCTGACGCTGAGCAAAGCAGACTACGAGAAACACAAAGTCTACGCCTG
CGAAGTCACCCATCAGGGCCTGAGCTCGCCCGTCACAAAGAGCTTCAACAGGGGAGAGTG
TTGA

Figure 11B

Amino acid sequence of light chain C-scFv tetravalent CH2 domain-deleted anti-LTBR x anti-TRAIL R2 bispecific antibody (anti-TRAIL R2 VL – kappa constant) [SEQ ID NO:28].

QLVLTQSSSVSFSLGASAKLTCTLSSQHSTYTIEWYQQQPLKPPKYVMELKKDGSHSTGDGIPD
RFSGSSSGADRYLSISNIQPEDEAIYICGVGDTIKEQFVYVFGGGTKVEIKRTVAAPSVFIFPPSD
EQLKSGTASVVCLLNNFYPREAKVQWKVDNALQSGNSQESVTEQDSKDSTYSLSSTLTLSKA
DYEKHKVYACEVTHQGLSSPVTKSFNRGEC*

Figure 12A.
Single-stranded DNA sequence of heavy chain N$_H$-scFv anti-LTBR x anti-TRAILR2 CH2 domain-deleted tetravalent bispecific antibody gene containing the G1/G3/Pro243Ala244Pro245 + [Gly/Ser] hinge connecting peptide [SEQ ID NO: 29].

GAGGTACAACTGGTGGAGTCTGGGGGAGGCTTAGTGAAGCCTGGAGGGTCCCTGAGGCTC
TCCTGTGCAGCCTCTGGATTCACTTTCAGTGACTATTACATGTATTGGTTTCGCCAGGCCCC
GGGAAAGGGGCTGGAGTGGGTCGCAACCATTAGTGATGGTGGTAGTTACACCTACTATCC
AGACAGTGTGAAGGGGCGATTCACCATCTCCAGAGACAATGCCAAGAACAGCCTCTACCT
GCAGATGAGCAGCCTGAGGGCTGAGGACACAGCTGTGTATTACTGCGCAAGAGAGGAGA
ATGGTAACTTTTACTACTTTGACTACTGGGGCCAAGGGACCACGGTCACCGTCTCCTCTGG
GGGCGGGGGGTCCGGGGGAGGCGGGTCGGGAGGTGGCGGAAGTGATATCCAGATGACCC
AGTCTCCATCATCCTTGTCTGCATCGGTGGGAGACAGGGTCACTATCACTTGCAAGGCGGG
TCAGGACATTAAAAGCTATTTAAGCTGGTACCAGCAGAAACCAGGGAAAGCGCCTAAGCT
TCTGATCTATTATGCAACAAGGTTGGCAGATGGGGTCCCATCAAGATTCAGTGGCAGTGG
ATCTGGTACAGATTATACTCTAACCATCAGCAGCCTGCAGCCTGAGGATTTCGCAACTTAT
TACTGTCTACAGCATGGTGAGAGCCCGTGGACGTTCGGTGGAGGCACCAAGCTGGAGATC
AAAGGCGGTGGAGGGTCCGGTGGAGGGGGCTCTGGAGGGGCGGTTCAGGGGGCGGTGG
ATCGGGGGGAGGTGGCTCCCAGATCCAGTTGGTGCAGTCTGGACCTGAGCTGAAGAAGCC
TGGAGAGACAGTCAAGATCTCCTGCAAGGCTTCTGGTTTTACCTTCACAGACTATTCAATA
CACTGGGTGAAACAGGCTCCAGGAAAGGGTTTAAAGTGGATGGGCTGGATAAACACTGA
GACTGGTGAGCCAACATATACAGATGACTTCAAGGGACGATTTGCCTTCTCTTTGGTGACC
TCTGCCACCACTGCCTATTTGCAGATCAACAACCTCAACAATGAGGACACGGCTACATTTT
TCTGTGCTAGATTCATCTATGATCCTTATTGGGGGTTTGCTTACTGGGGCCAGGGGACTCT
GGTCACTGTCTCCGCAGCTAGCACCAAGGGCCCATCGGTCTTCCCCCTGGCACCCTCCTCC
AAGAGCACCTCTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCCCTCCAGCAGCT
TGGGCACCCAGACCTACATCTGCAACGTGAATCACAAGCCCAGCAACACCAAGGTGGACA
AGAAAGTTGAGCCCAAATCTTGTGACAAAACTCACACATGCCCACCGTGCCCAGAGCCCA
AATCTTGTGACACACCTCCCCCATGCCCACGGTGCCCAGCACCTGGAGGTGGCTCGAGTG
GAGGCGGTTCCGGAGGGCAGCCCCGAGAACCACAGGTGTACACCCTGCCCCCATCCCGGG
ATGAGCTGACCAAGAACCAGGTCAGCCTGACCTGCCTGGTCAAAGGCTTCTATCCCAGCG
ACATCGCCGTGGAGTGGGAGAGCAATGGGCAGCCGGAGAACAACTACAAGACCACGCCT
CCCGTGCTGGACTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTGCACAACCACT
ACACGCAGAAGAGCCTCTCCCTGTCTCCGGGTTGA

Figure 12B.
Amino acid sequence of heavy chain N$_H$-scFv anti-LTBR x anti-TRAILR2 CH2 domain-deleted tetravalent bispecific antibody gene containing the G1/G3/Pro243Ala244Pro245 + [Gly/Ser] hinge connecting peptide [SEQ ID NO:30].

EVQLVESGGGLVKPGGSLRLSCAASGFTFSDYYMYWFRQAPGKGLEWVATISDGGSYTYYPD
SVKGRFTISRDNAKNSLYLQMSSLRAEDTAVYYCAREENGNFYYFDYWGQGTTVTVSSGGG
GSGGGGSGGGGSDIQMTQSPSSLSASVGDRVTITCKAGQDIKSYLSWYQQKPGKAPKLLIYYA
TRLADGVPSRFSGSGSGTDYTLTISSLQPEDFATYYCLQHGESPWTFGGGTKLEIKGGGGSGGG
GSGGGGSGGGGSGGGGSQIQLVQSGPELKKPGETVKISCKASGFTFTDYSIHWVKQAPGKGLK
WMGWINTETGEPTYTDDFKGRFAFSLVTSATTAYLQINNLNNEDTATFFCARFIYDPYWGFAY
WGQGTLVTVSAASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCPEPK
SCDTPPPCPRCPAPGGGSSGGGSGGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSLS
LSPG*

Figure 13A.
Single-stranded DNA sequence of light chain N$_H$-scFv anti-LTBR x anti-TRAILR2 CH2 domain-deleted tetravalent bispecific antibody gene. [SEQ ID NO: 31]

CAACTTGTGCTCACTCAGTCATCTTCAGTCTCTTTCTCCCTGGGAGCCTCAGCAAAACTCA
CGTGCACCTTGAGTAGTCAGCACAGTACGTACACCATTGAATGGTATCAGCAACAGCCCC
TCAAGCCTCCTAAGTATGTGATGGAGCTTAAGAAAGATGGAAGCCACAGCACAGGTGATG
GGATTCCTGATCGCTTCTCTGGATCCAGCTCTGGTGCTGATCGCTACCTTAGCATTTCCAAC
ATCCAGCCTGAAGATGAAGCAATATACATCTGTGGTGTGGGTGATACAATTAAGGAACAA
TTTGTGTATGTTTTCGGCGGTGGAACCAAGGTCGAAATCAAACGTACGGTGGCTGCACCAT
CTGTCTTCATCTTCCCGCCATCTGATGAGCAGTTGAAATCTGGAACTGCCTCTGTTGTGTGC
CTGCTGAATAACTTCTATCCCAGAGAGGCCAAAGTACAGTGGAAGGTGGATAACGCCCTC
CAATCGGGTAACTCCCAGGAGAGTGTCACAGAGCAGGACAGCAAGGACAGCACCTACAG
CCTCAGCAGCACCCTGACGCTGAGCAAAGCAGACTACGAGAAACACAAAGTCTACGCCTG
CGAAGTCACCCATCAGGGCCTGAGCTCGCCCGTCACAAAGAGCTTCAACAGGGGAGAGTG
TTGA

Figure 13B.
Amino acid sequence of light chain N$_H$-scFv anti-LTBR x anti-TRAILR2 CH2 domain-deleted tetravalent bispecific antibody gene. [SEQ ID NO: 32]

QLVLTQSSSVSFSLGASAKLTCTLSSQHSTYTIEWYQQQPLKPPKYVMELKKDGSHSTGDGIPD
RFSGSSSGADRYLSISNIQPEDEAIYICGVGDTIKEQFVYVFGGGTKVEIKRTVAAPSVFIFPPSD
EQLKSGTASVVCLLNNFYPREAKVQWKVDNALQSGNSQESVTEQDSKDSTYSLSSTLTLSKA
DYEKHKVYACEVTHQGLSSPVTKSFNRGEC*

Figure 14A.
Single-stranded DNA sequence of heavy chain $N_L$-scFv anti-LTBR x anti-TRAILR2 CH2 domain-deleted tetravalent bispecific antibody gene containing the G1/G3/Pro243Ala244Pro245 + [Gly/Ser] hinge connecting peptide [SEQ ID NO: 33].

```
CAGATCCAGTTGGTGCAGTCTGGACCTGAGCTGAAGAAGCCTGGAGAGACAGTCAAGATC
TCCTGCAAGGCTTCTGGTTTTACCTTCACAGACTATTCAATACACTGGGTGAAACAGGCTC
CAGGAAAGGGTTTAAAGTGGATGGGCTGGATAAACACTGAGACTGGTGAGCCAACATAT
ACAGATGACTTCAAGGGACGATTTGCCTTCTCTTTGGTGACCTCTGCCACCACTGCCTATT
TGCAGATCAACAACCTCAACAATGAGGACACGGCTACATTTTTCTGTGCTAGATTCATCTA
TGATCCTTATTGGGGGTTTGCTTACTGGGGCCAGGGGACTCTGGTCACTGTCTCCGCAGCT
AGCACCAAGGGCCCATCGGTCTTCCCCCTGGCACCCTCCTCCAAGAGCACCTCTGGGGGC
ACAGCGGCCCTGGGCTGCCTGGTCAAGGACTACTTCCCCGAACCGGTGACGGTGTCGTGG
AACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTACA
TCTGCAACGTGAATCACAAGCCCAGCAACACCAAGGTGGACAAGAAAGTTGAGCCCAAA
TCTTGTGACAAAACTCACACATGCCCACCGTGCCCAGAGCCCAAATCTTGTGACACACCTC
CCCCATGCCCACGGTGCCCAGCACCTGGAGGTGGCTCGAGTGGAGGCGGTTCCGGAGGGC
AGCCCCGAGAACCACAGGTGTACACCCTGCCCCCATCCCGGGATGAGCTGACCAAGAACC
AGGTCAGCCTGACCTGCCTGGTCAAAGGCTTCTATCCCAGCGACATCGCCGTGGAGTGGG
AGAGCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGCCTCT
CCCTGTCTCCGGGTTGA
```

Figure 14B.
Amino acid sequence of heavy chain $N_L$-scFv anti-LTBR x anti-TRAILR2 CH2 domain-deleted tetravalent bispecific antibody gene containing the G1/G3/Pro243Ala244Pro245 + [Gly/Ser] hinge connecting peptide [SEQ ID NO: 34].

```
QIQLVQSGPELKKPGETVKISCKASGFTFTDYSIHWVKQAPGKGLKWMGWINTETGEPTYTDD
FKGRFAFSLVTSATTAYLQINNLNNEDTATFFCARFIYDPYWGFAYWGQGTLVTVSAASTKGP
SVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPEPKSCDTPPPCPRCPAPGGGS
SGGGSGGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG*
```

Figure 15A.
Single-stranded DNA sequence of light chain $N_L$-scFv anti-LTBR x anti-TRAILR2 CH2 domain-deleted tetravalent bispecific antibody gene [SEQ ID NO: 35].

GAGGTACAACTGGTGGAGTCTGGGGGAGGCTTAGTGAAGCCTGGAGGGTCCCTGAGGCTC
TCCTGTGCAGCCTCTGGATTCACTTTCAGTGACTATTACATGTATTGGTTTCGCCAGGCCCC
GGGAAAGGGGCTGGAGTGGGTCGCAACCATTAGTGATGGTGGTAGTTACACCTACTATCC
AGACAGTGTGAAGGGGCGATTCACCATCTCCAGAGACAATGCCAAGAACAGCCTCTACCT
GCAGATGAGCAGCCTGAGGGCTGAGGACACAGCTGTGTATTACTGCGCAAGAGAGGAGA
ATGGTAACTTTTACTACTTTGACTACTGGGGCCAAGGGACCACGGTCACCGTCTCCTCTGG
GGGCGGGGGGTCCGGGGGAGGCGGGTCGGGAGGTGGCGGAAGTGATATCCAGATGACCC
AGTCTCCATCATCCTTGTCTGCATCGGTGGGAGACAGGGTCACTATCACTTGCAAGGCGGG
TCAGGACATTAAAAGCTATTTAAGCTGGTACCAGCAGAAACCAGGGAAAGCGCCTAAGCT
TCTGATCTATTATGCAACAAGGTTGGCAGATGGGGTCCCATCAAGATTCAGTGGCAGTGG
ATCTGGTACAGATTATACTCTAACCATCAGCAGCCTGCAGCCTGAGGATTTCGCAACTTAT
TACTGTCTACAGCATGGTGAGAGCCCGTGGACGTTCGGTGGAGGCACCAAGCTGGAGATC
AAAGGCGGTGGAGGGTCCGGTGGAGGGGGCTCTGGAGGGGGCGGTTCAGGGGGCGGTGG
ATCGGGGGGAGGTGGCTCCCAACTTGTGCTCACTCAGTCATCTTCAGTCTCTTTCTCCCTG
GGAGCCTCAGCAAAACTCACGTGCACCTTGAGTAGTCAGCACAGTACGTACACCATTGAA
TGGTATCAGCAACAGCCCCTCAAGCCTCCTAAGTATGTGATGGAGCTTAAGAAAGATGGA
AGCCACAGCACAGGTGATGGGATTCCTGATCGCTTCTCTGGATCCAGCTCTGGTGCTGATC
GCTACCTTAGCATTTCCAACATCCAGCCTGAAGATGAAGCAATATACATCTGTGGTGTGGG
TGATACAATTAAGGAACAATTTGTGTATGTTTTCGGCGGTGGAACCAAGGTCGAAATCAA
ACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGT
GGAAGGTGGATAACGCCCTCCAATCGGGTAACTCCCAGGAGAGTGTCACAGAGCAGGAC
AGCAAGGACAGCACCTACAGCCTCAGCAGCACCCTGACGCTGAGCAAAGCAGACTACGA
GAAACACAAAGTCTACGCCTGCGAAGTCACCCATCAGGGCCTGAGCTCGCCCGTCACAAA
GAGCTTCAACAGGGGAGAGTGTTGA

Figure 15B.
Amino acid sequence of light chain $N_L$-scFv anti-LTBR x anti-TRAILR2 CH2 domain-deleted tetravalent bispecific antibody gene [SEQ ID NO: 36].

EVQLVESGGGLVKPGGSLRLSCAASGFTFSDYYMYWFRQAPGKGLEWVATISDGGSYTYYPD
SVKGRFTISRDNAKNSLYLQMSSLRAEDTAVYYCAREENGNFYYFDYWGQGTTVTVSSGGG
GSGGGGSGGGGSDIQMTQSPSSLSASVGDRVTITCKAGQDIKSYLSWYQQKPGKAPKLLIYYA
TRLADGVPSRFSGSGSGTDYTLTISSLQPEDFATYYCLQHGESPWTFGGGTKLEIKGGGGSGGG
GSGGGGSGGGGSGGGGSQLVLTQSSSVSFSLGASAKLTCTLSSQHSTYTIEWYQQQPLKPPKY
VMELKKDGSHSTGDGIPDRFSGSSSGADRYLSISNIQPEDEAIYICGVGDTIKEQFVYVFGGGTK
VEIKRTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC*

SEQUENCE LISTING

```
<160> NUMBER OF SEQ ID NOS: 46

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Ser Ser Gly Gly Gly Ser Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Pro Lys Ser Cys Asp Lys Thr His Thr
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Pro Pro Cys Pro
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Pro Glu Leu Leu Gly Gly Pro
1               5

<210> SEQ ID NO 5
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 5

Glu Leu Lys Thr Pro Leu Gly Asp Thr Thr His Thr
1               5                   10

<210> SEQ ID NO 6
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
            20                  25                  30

Arg Cys Pro Glu Pro Lys Ser Cys Asp Thr Pro Pro Pro Cys Pro Arg
        35                  40                  45

Cys Pro
    50

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Pro Lys Ser Cys Asp Lys Thr His Thr Cys Pro Pro Cys Gly Gly
1               5                   10                  15

Gly Ser Ser Gly Gly Gly Ser Gly
            20

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Pro Lys Ser Cys Asp Lys Thr His Thr Cys Pro Pro Cys Pro Glu
1               5                   10                  15

Pro Lys Ser Cys Asp Thr Pro Pro Pro Cys Pro Arg Cys Pro Gly Gly
            20                  25                  30

Gly Ser Ser Gly Gly Gly Ser Gly
        35                  40

<210> SEQ ID NO 9
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Glu Pro Lys Ser Cys Asp Lys Thr His Thr Cys Pro Cys Pro Glu
 1               5                  10                  15

Pro Lys Ser Cys Asp Thr Pro Pro Cys Pro Arg Cys Pro Ala Pro
                20                  25                  30

Gly Gly Gly Ser Ser Gly Gly Ser Gly
            35                  40
```

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Glu Pro Lys Ser Cys Asp Lys Thr His Thr Ser Pro Pro Cys Pro Gly
 1               5                  10                  15

Gly Gly Ser Ser Gly Gly Gly Ser Gly
            20                  25
```

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Glu Pro Lys Ser Cys Asp Lys Thr His Thr Ser Pro Pro Cys Pro Ala
 1               5                  10                  15

Pro Gly Gly Gly Ser Ser Gly Gly Gly Ser Gly
                20                  25
```

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Glu Pro Lys Ser Cys Asp Lys Thr His Thr Cys Pro Pro Ser Pro Gly
 1               5                  10                  15

Gly Gly Ser Ser Gly Gly Gly Ser Gly
            20                  25
```

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Glu Pro Lys Ser Cys Asp Lys Thr His Thr Cys Pro Pro Ser Pro Ala
 1               5                  10                  15

Pro Gly Gly Gly Ser Ser Gly Gly Gly Ser Gly
                20                  25
```

<210> SEQ ID NO 14

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Pro Lys Ser Cys Asp Lys Thr His Thr Cys Pro Pro Cys Pro Ala
 1               5                  10                  15

Pro Gly Gly Gly Ser Ser Gly Gly Gly Ser Gly
             20                  25

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Pro Lys Ser Cys Asp Lys Thr His Thr Cys Pro Pro Cys Pro Gly
 1               5                  10                  15

Gly Gly Ser Ser Gly Gly Gly Ser Gly
             20                  25

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Gly Lys Thr Ile Ser Lys Lys Ala Lys
 1               5                  10

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Ser Gly Gly Gly Gly Ser
 1               5                  10                  15

<210> SEQ ID NO 18
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser Gly Gly Gly Ser Gly Gly Gly Gly Ser Gly
 1               5                  10                  15

Gly Gly Ser Gly Gly Gly Ala Ser
             20                  25

<210> SEQ ID NO 19
<211> LENGTH: 9
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 aagatctcc                                                                 9

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Ser Lys Tyr Gly Pro Pro
 1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Pro Ser Cys Pro
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Pro Glu Phe Leu Gly Gly Pro
 1               5

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Ser Lys Tyr Gly Pro Pro Cys Pro Ser Cys Pro Glu Pro Lys Ser
 1               5                  10                  15

Cys Asp Thr Pro Pro Cys Pro Arg Cys Pro Ala Pro
             20                  25

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

Cys Pro Glu Pro Lys Ser Cys Asp Thr Pro Pro Cys Pro Arg
 1               5                  10                  15

<210> SEQ ID NO 25
<211> LENGTH: 1875
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

| | |
|---|---:|
| cagatccagt tggtgcagtc tggacctgag ctgaagaagc ctggagagac agtcaagatc | 60 |
| tcctgcaagg cttctggttt taccttcaca gactattcaa tacactgggt gaaacaggct | 120 |
| ccaggaaagg gtttaaagtg gatgggctgg ataaacactg agactggtga gccaacatat | 180 |
| acagatgact tcaagggacg atttgccttc tctttggtga cctctgccac cactgcctat | 240 |
| ttgcagatca caaccctcaa caatgaggac acggctacat ttttctgtgc tagattcatc | 300 |
| tatgatcctt attgggggtt tgcttactgg ggccagggga ctctggtcac tgtctccgca | 360 |
| gctagcacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaaaactca cacatgccca ccgtgcccag cccaaatc ttgtgacaca | 720 |
| cctcccccat gcccacggtg cccagcacct gaggtggct cgagtggagg cggttccgga | 780 |
| gggcagcccc gagaaccaca ggtgtacacc ctgcccccat cccgggatga gctgaccaag | 840 |
| aaccaggtca gcctgacctg cctggtcaaa ggcttctatc ccagcgacat cgccgtggag | 900 |
| tgggagagca atgggcagcc ggagaacaac tacaagacca cgcctcccgt gctggactcc | 960 |
| gacggctcct tcttcctcta cagcaagctc accgtggaca agagcaggtg gcagcagggg | 1020 |
| aacgtcttct catgctccgt gatgcatgag gctctgcaca accactacac gcagaagagc | 1080 |
| ctctccctgt ctccgggttc cggcgggggt ggatccggtg aggggggctc cggcggtggc | 1140 |
| gggtccgagg tacaactggt ggagtctggg ggaggcttag tgaagcctgg agggtccctg | 1200 |
| aggctctcct gtgcagcctc tggattcact ttcagtgact attacatgta ttggtttcgc | 1260 |
| caggcccccgg gaaaggggct ggagtgggtc gcaaccatta gtgatggtgg tagttacacc | 1320 |
| tactatccag acagtgtgaa ggggcgattc accatctcca gagacaatgc caagaacagc | 1380 |
| ctctacctgc agatgagcag cctgagggct gaggacacag ctgtgtatta ctgcgcaaga | 1440 |
| gaggagaatg gtaacttta ctactttgac tactggggcc aagggaccac ggtcaccgtc | 1500 |
| tcctctgggg gcgggggggtc cggggaggc gggtcgggag gtgcggaag tgatatccag | 1560 |
| atgacccagt ctccatcatc cttgtctgca tcggtgggag acagggtcac tatcacttgc | 1620 |
| aaggcgggtc aggacattaa aagctattta agctggtacc agcagaaacc agggaaagcg | 1680 |
| cctaagcttc tgatctatta tgcaacaagg ttggcagatg ggtcccatc aagattcagt | 1740 |
| ggcagtggat ctggtacaga ttatactcta accatcagca gcctgcagcc tgaggatttc | 1800 |
| gcaacttatt actgtctaca gcatggtgag agcccgtgga cgttcggtgg aggcaccaag | 1860 |
| ctggagatca aatga | 1875 |

<210> SEQ ID NO 26

```
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26
```

| | | | | | | | | | | | | | | | |
|---|---|---|---|---|---|---|---|---|---|---|---|---|---|---|---|
| Gln | Ile | Gln | Leu | Val | Gln | Ser | Gly | Pro | Glu | Leu | Lys | Lys | Pro | Gly | Glu |
| 1 | | | | 5 | | | | | 10 | | | | | 15 | |
| Thr | Val | Lys | Ile | Ser | Cys | Lys | Ala | Ser | Gly | Phe | Thr | Phe | Thr | Asp | Tyr |
| | | | 20 | | | | | 25 | | | | | 30 | | |
| Ser | Ile | His | Trp | Val | Lys | Gln | Ala | Pro | Gly | Lys | Gly | Leu | Lys | Trp | Met |
| | | 35 | | | | | 40 | | | | | 45 | | | |
| Gly | Trp | Ile | Asn | Thr | Glu | Thr | Gly | Glu | Pro | Thr | Tyr | Thr | Asp | Asp | Phe |
| | 50 | | | | | 55 | | | | | 60 | | | | |
| Lys | Gly | Arg | Phe | Ala | Phe | Ser | Leu | Val | Thr | Ser | Ala | Thr | Thr | Ala | Tyr |
| 65 | | | | | 70 | | | | | 75 | | | | | 80 |
| Leu | Gln | Ile | Asn | Asn | Leu | Asn | Asn | Glu | Asp | Thr | Ala | Thr | Phe | Phe | Cys |
| | | | | 85 | | | | | 90 | | | | | 95 | |
| Ala | Arg | Phe | Ile | Tyr | Asp | Pro | Tyr | Trp | Gly | Phe | Ala | Tyr | Trp | Gly | Gln |
| | | | 100 | | | | | 105 | | | | | 110 | | |
| Gly | Thr | Leu | Val | Thr | Val | Ser | Ala | Ala | Ser | Thr | Lys | Gly | Pro | Ser | Val |
| | | 115 | | | | | 120 | | | | | 125 | | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Lys | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Glu | Pro | Lys | Ser | Cys | Asp | Thr |
| 225 | | | | | 230 | | | | | 235 | | | | | 240 |
| Pro | Pro | Pro | Cys | Pro | Arg | Cys | Pro | Ala | Pro | Gly | Gly | Ser | Ser | Gly | |
| | | | | 245 | | | | | 250 | | | | | 255 | |
| Gly | Gly | Ser | Gly | Gly | Gln | Pro | Arg | Glu | Pro | Gln | Val | Tyr | Thr | Leu | Pro |
| | | | 260 | | | | | 265 | | | | | 270 | | |
| Pro | Ser | Arg | Asp | Glu | Leu | Thr | Lys | Asn | Gln | Val | Ser | Leu | Thr | Cys | Leu |
| | | 275 | | | | | 280 | | | | | 285 | | | |
| Val | Lys | Gly | Phe | Tyr | Pro | Ser | Asp | Ile | Ala | Val | Glu | Trp | Glu | Ser | Asn |
| | 290 | | | | | 295 | | | | | 300 | | | | |
| Gly | Gln | Pro | Glu | Asn | Asn | Tyr | Lys | Thr | Thr | Pro | Pro | Val | Leu | Asp | Ser |
| 305 | | | | | 310 | | | | | 315 | | | | | 320 |
| Asp | Gly | Ser | Phe | Phe | Leu | Tyr | Ser | Lys | Leu | Thr | Val | Asp | Lys | Ser | Arg |
| | | | | 325 | | | | | 330 | | | | | 335 | |
| Trp | Gln | Gln | Gly | Asn | Val | Phe | Ser | Cys | Ser | Val | Met | His | Glu | Ala | Leu |
| | | | 340 | | | | | 345 | | | | | 350 | | |
| His | Asn | His | Tyr | Thr | Gln | Lys | Ser | Leu | Ser | Leu | Ser | Pro | Gly | Ser | Gly |
| | | 355 | | | | | 360 | | | | | 365 | | | |
| Gly | Gly | Gly | Ser | Gly | Gly | Gly | Ser | Gly | Gly | Gly | Gly | Ser | Glu | Val | |
| | 370 | | | | | 375 | | | | | 380 | | | | |

Gln Leu Val Glu Ser Gly Gly Leu Val Lys Pro Gly Ser Leu
385                 390                 395                 400

Arg Leu Ser Cys Ala Ala Ser Gly Phe Thr Phe Ser Asp Tyr Tyr Met
            405                 410                 415

Tyr Trp Phe Arg Gln Ala Pro Gly Lys Gly Leu Glu Trp Val Ala Thr
        420                 425                 430

Ile Ser Asp Gly Gly Ser Tyr Thr Tyr Tyr Pro Asp Ser Val Lys Gly
    435                 440                 445

Arg Phe Thr Ile Ser Arg Asp Asn Ala Lys Asn Ser Leu Tyr Leu Gln
450                 455                 460

Met Ser Ser Leu Arg Ala Glu Asp Thr Ala Val Tyr Tyr Cys Ala Arg
465                 470                 475                 480

Glu Glu Asn Gly Asn Phe Tyr Tyr Phe Asp Tyr Trp Gly Gln Gly Thr
            485                 490                 495

Thr Val Thr Val Ser Ser Gly Gly Gly Ser Gly Gly Gly Gly Ser
        500                 505                 510

Gly Gly Gly Gly Ser Asp Ile Gln Met Thr Gln Ser Pro Ser Ser Leu
    515                 520                 525

Ser Ala Ser Val Gly Asp Arg Val Thr Ile Thr Cys Lys Ala Gly Gln
530                 535                 540

Asp Ile Lys Ser Tyr Leu Ser Trp Tyr Gln Gln Lys Pro Gly Lys Ala
545                 550                 555                 560

Pro Lys Leu Leu Ile Tyr Tyr Ala Thr Arg Leu Ala Asp Gly Val Pro
            565                 570                 575

Ser Arg Phe Ser Gly Ser Gly Ser Gly Thr Asp Tyr Thr Leu Thr Ile
        580                 585                 590

Ser Ser Leu Gln Pro Glu Asp Phe Ala Thr Tyr Tyr Cys Leu Gln His
    595                 600                 605

Gly Glu Ser Pro Trp Thr Phe Gly Gly Gly Thr Lys Leu Glu Ile Lys
610                 615                 620

<210> SEQ ID NO 27
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
caacttgtgc tcactcagtc atcttcagtc tctttctccc tgggagcctc agcaaaactc      60
acgtgcacct tgagtagtca gcacagtacg tacaccattg aatggtatca gcaacagccc     120
ctcaagcctc ctaagtatgt gatggagctt aagaaagatg gaagccacag cacaggtgat     180
gggattcctg atcgcttctc tggatccagc tctggtgctg atcgctacct tagcatttcc     240
aacatccagc tgaagatgaa gcaatatac atctgtggtg tgggtgatac aattaaggaa     300
caatttgtgt atgttttcgg cggtggaacc aaggtcgaaa tcaaacgtac ggtggctgca     360
ccatctgtct tcatcttccc gccatctgat gagcagttga atctggaac tgcctctgtt     420 gtgtgcctgc tgaataactt ctatcccaga gaggccaaag tacagtggaa ggtggataac     480
gccctccaat cgggtaactc ccaggagagt gtcacagagc aggacagcaa ggacagcacc     540
tacagcctca gcagcaccct gacgctgagc aaagcagact acgagaaaca caaagtctac     600
gcctgcgaag tcacccatca gggcctgagc tcgcccgtca caaagagctt caacagggga     660
gagtgttga                                                             669

<210> SEQ ID NO 28
<211> LENGTH: 222
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Gln Leu Val Leu Thr Gln Ser Ser Val Ser Phe Ser Leu Gly Ala
1               5                   10                  15

Ser Ala Lys Leu Thr Cys Thr Leu Ser Ser Gln His Ser Thr Tyr Thr
                20                  25                  30

Ile Glu Trp Tyr Gln Gln Pro Leu Lys Pro Pro Lys Tyr Val Met
            35                  40                  45

Glu Leu Lys Lys Asp Gly Ser His Ser Thr Gly Asp Gly Ile Pro Asp
        50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Ile Tyr Ile Cys Gly Val Gly Asp
                85                  90                  95

Thr Ile Lys Glu Gln Phe Val Tyr Val Phe Gly Gly Gly Thr Lys Val
                100                 105                 110

Glu Ile Lys Arg Thr Val Ala Ala Pro Ser Val Phe Ile Phe Pro Pro
            115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 29
<211> LENGTH: 1902
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
gaggtacaac tggtggagtc tgggggaggc ttagtgaagc ctggagggtc cctgaggctc     60
tcctgtgcag cctctggatt cactttcagt gactattaca tgtattggtt tcgccaggcc    120
ccgggaaagg ggctggagtg ggtcgcaacc attagtgatg gtggtagtta cacctactat    180
ccagacagtg tgaaggggcg attcaccatc tccagagaca atgccaagaa cagcctctac    240
ctgcagatga gcagcctgag gctgaggac acagctgtgt attactgcgc aagagaggag    300
aatggtaact tttactactt tgactactgg ggccaaggga ccacggtcac cgtctcctct    360
gggggcgggg gtccgggggg aggcgggtcg ggaggtggcg gaagtgatat ccagatgacc    420
cagtctccat catccttgtc tgcatcggtg ggagacaggg tcactatcac ttgcaaggcg    480

```
ggtcaggaca ttaaaagcta tttaagctgg taccagcaga aaccaggaa agcgcctaag    540 cttctgatct attatgcaac aaggttggca gatggggtcc catcaagatt cagtggcagt    600
ggatctggta cagattatac tctaaccatc agcagcctgc agcctgagga tttcgcaact    660
tattactgtc tacagcatgg tgagagcccg tggacgttcg gtggaggcac caagctggag    720
atcaaaggcg gtggagggtc cggtggaggg ggctctggag ggggcggttc agggggcggt    780
ggatcggggg gaggtggctc ccagatccag ttggtgcagt ctggacctga gctgaagaag    840
cctggagaga cagtcaagat ctcctgcaag gcttctggtt ttaccttcac agactattca    900
atacactggg tgaaacaggc tccaggaaag ggtttaaagt ggatgggctg gataaacact    960
gagactggtg agccaacata tacagatgac ttcaagggac gatttgcctt ctctttggtg   1020
acctctgcca ccactgccta tttgcagatc aacaacctca caatgagga cacggctaca   1080 tttttctgtg ctagattcat ctatgatcct tattgggggt ttgcttactg gggccagggg   1140
actctggtca ctgtctccgc agctagcacc aagggcccat cggtcttccc cctggcaccc   1200
tcctccaaga gcacctctgg gggcacagcg gccctgggct gcctggtcaa ggactacttc   1260
cccgaaccgg tgacggtgtc gtggaactca ggcgccctga ccagcggcgt gcacaccttc   1320
ccggctgtcc tacagtcctc aggactctac tccctcagca gcgtggtgac cgtgccctcc   1380
agcagcttgg gcacccagac ctacatctgc aacgtgaatc acaagcccag caacaccaag   1440
gtggacaaga agttgagcc caaatcttgt gacaaaactc acacatgccc accgtgccca   1500
gagcccaaat cttgtgacac acctccccca tgcccacggt gcccagcacc tgaggtggc    1560 tcgagtggag gcggttccgg agggcagccc cgagaaccac aggtgtacac cctgcccca    1620 tcccgggatg agctgaccaa gaaccaggtc agcctgacct gcctggtcaa aggcttctat   1680
cccagcgaca tcgccgtgga gtgggagagc aatgggcagc cggagaacaa ctacaagacc   1740
acgcctcccg tgctggactc cgacggctcc ttcttcctct acagcaagct caccgtggac   1800
aagagcaggt ggcagcaggg gaacgtcttc tcatgctccg tgatgcatga ggctctgcac   1860
aaccactaca cgcagaagag cctctccctg tctccgggtt ga                       1902
```

<210> SEQ ID NO 30
<211> LENGTH: 633
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 30

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Tyr Met Tyr Trp Phe Arg Gln Ala Pro Gly Lys Gly Leu Glu Trp Val
         35                  40                  45

Ala Thr Ile Ser Asp Gly Gly Ser Tyr Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Ser Ser Leu Arg Ala Glu Asp Thr Ala Val Tyr Tyr Cys
                 85                  90                  95

Ala Arg Glu Glu Asn Gly Asn Phe Tyr Tyr Phe Asp Tyr Trp Gly Gln
            100                 105                 110
```

```
Gly Thr Thr Val Thr Val Ser Ser Gly Gly Gly Ser Gly Gly
            115                 120                 125

Gly Ser Gly Gly Gly Ser Asp Ile Gln Met Thr Gln Ser Pro Ser
    130                 135                 140

Ser Leu Ser Ala Ser Val Gly Asp Arg Val Thr Ile Thr Cys Lys Ala
145                 150                 155                 160

Gly Gln Asp Ile Lys Ser Tyr Leu Ser Trp Tyr Gln Gln Lys Pro Gly
                165                 170                 175

Lys Ala Pro Lys Leu Leu Ile Tyr Tyr Ala Thr Arg Leu Ala Asp Gly
            180                 185                 190

Val Pro Ser Arg Phe Ser Gly Ser Gly Ser Gly Thr Asp Tyr Thr Leu
        195                 200                 205

Thr Ile Ser Ser Leu Gln Pro Glu Asp Phe Ala Thr Tyr Tyr Cys Leu
    210                 215                 220

Gln His Gly Glu Ser Pro Trp Thr Phe Gly Gly Gly Thr Lys Leu Glu
225                 230                 235                 240

Ile Lys Gly Gly Gly Gly Ser Gly Gly Gly Ser Gly Gly Gly Gly
                245                 250                 255

Ser Gly Gly Gly Gly Ser Gly Gly Gly Gly Ser Gln Ile Gln Leu Val
                260                 265                 270

Gln Ser Gly Pro Glu Leu Lys Lys Pro Gly Glu Thr Val Lys Ile Ser
        275                 280                 285

Cys Lys Ala Ser Gly Phe Thr Phe Thr Asp Tyr Ser Ile His Trp Val
        290                 295                 300

Lys Gln Ala Pro Gly Lys Gly Leu Lys Trp Met Gly Trp Ile Asn Thr
305                 310                 315                 320

Glu Thr Gly Glu Pro Thr Tyr Thr Asp Asp Phe Lys Gly Arg Phe Ala
                325                 330                 335

Phe Ser Leu Val Thr Ser Ala Thr Thr Ala Tyr Leu Gln Ile Asn Asn
            340                 345                 350

Leu Asn Asn Glu Asp Thr Ala Thr Phe Phe Cys Ala Arg Phe Ile Tyr
        355                 360                 365

Asp Pro Tyr Trp Gly Phe Ala Tyr Trp Gly Gln Gly Thr Leu Val Thr
    370                 375                 380

Val Ser Ala Ala Ser Thr Lys Gly Pro Ser Val Phe Pro Leu Ala Pro
385                 390                 395                 400

Ser Ser Lys Ser Thr Ser Gly Gly Thr Ala Ala Leu Gly Cys Leu Val
                405                 410                 415

Lys Asp Tyr Phe Pro Glu Pro Val Thr Val Ser Trp Asn Ser Gly Ala
            420                 425                 430

Leu Thr Ser Gly Val His Thr Phe Pro Ala Val Leu Gln Ser Ser Gly
        435                 440                 445

Leu Tyr Ser Leu Ser Ser Val Val Thr Val Pro Ser Ser Ser Leu Gly
    450                 455                 460

Thr Gln Thr Tyr Ile Cys Asn Val Asn His Lys Pro Ser Asn Thr Lys
465                 470                 475                 480

Val Asp Lys Lys Val Glu Pro Lys Ser Cys Asp Lys Thr His Thr Cys
                485                 490                 495

Pro Pro Cys Pro Glu Pro Lys Ser Cys Asp Thr Pro Pro Cys Pro
            500                 505                 510

Arg Cys Pro Ala Pro Gly Gly Gly Ser Gly Gly Gly Ser Gly Gly
        515                 520                 525

Gln Pro Arg Glu Pro Gln Val Tyr Thr Leu Pro Pro Ser Arg Asp Glu
```

```
                  530                 535                 540
Leu Thr Lys Asn Gln Val Ser Leu Thr Cys Leu Val Lys Gly Phe Tyr
545                 550                 555                 560

Pro Ser Asp Ile Ala Val Glu Trp Glu Ser Asn Gly Gln Pro Glu Asn
                565                 570                 575

Asn Tyr Lys Thr Thr Pro Pro Val Leu Asp Ser Asp Gly Ser Phe Phe
                580                 585                 590

Leu Tyr Ser Lys Leu Thr Val Asp Lys Ser Arg Trp Gln Gln Gly Asn
                595                 600                 605

Val Phe Ser Cys Ser Val Met His Glu Ala Leu His Asn His Tyr Thr
                610                 615                 620

Gln Lys Ser Leu Ser Leu Ser Pro Gly
625                 630

<210> SEQ ID NO 31
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caacttgtgc tcactcagtc atcttcagtc tctttctccc tgggagcctc agcaaaactc      60
acgtgcacct tgagtagtca gcacagtacg tacaccattg aatggtatca gcaacagccc     120
ctcaagcctc ctaagtatgt gatggagctt aagaaagatg gaagccacag cacaggtgat     180
gggattcctg atcgcttctc tggatccagc tctggtgctg atcgctacct tagcatttcc     240
aacatccagc tgaagatgaa gcaatatac atctgtggtg tggtgataca aattaaggaa      300
caatttgtgt atgttttcgg cggtggaacc aaggtcgaaa tcaaacgtac ggtggctgca     360
ccatctgtct tcatcttccc gccatctgat gagcagttga aatctggaac tgcctctgtt     420
gtgtgcctgc tgaataactt ctatcccaga gaggccaaag tacagtggaa ggtggataac     480
gccctccaat cgggtaactc ccaggagagt gtcacagagc aggacagcaa ggacagcacc     540
tacagcctca gcagcaccct gacgctgagc aaagcagact acgagaaaca caaagtctac     600
gcctgcgaag tcacccatca gggcctgagc tcgcccgtca caaagagctt caacagggga     660
gagtgttga                                                             669

<210> SEQ ID NO 32
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Leu Val Leu Thr Gln Ser Ser Val Ser Phe Ser Leu Gly Ala
 1               5                  10                  15

Ser Ala Lys Leu Thr Cys Thr Leu Ser Ser Gln His Ser Thr Tyr Thr
                20                  25                  30

Ile Glu Trp Tyr Gln Gln Gln Pro Leu Lys Pro Pro Lys Tyr Val Met
                35                  40                  45

Glu Leu Lys Lys Asp Gly Ser His Ser Thr Gly Asp Gly Ile Pro Asp
                50                  55                  60

Arg Phe Ser Gly Ser Ser Ser Gly Ala Asp Arg Tyr Leu Ser Ile Ser
65                  70                  75                  80
```

Asn Ile Gln Pro Glu Asp Glu Ala Ile Tyr Ile Cys Gly Val Gly Asp
                85                  90                  95

Thr Ile Lys Glu Gln Phe Val Tyr Val Phe Gly Gly Gly Thr Lys Val
            100                 105                 110

Glu Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 33
<211> LENGTH: 1101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
cagatccagt tggtgcagtc tggacctgag ctgaagaagc ctggagagac agtcaagatc     60
tcctgcaagg cttctggttt taccttcaca gactattcaa tacactgggt gaaacaggct    120
ccaggaaagg gtttaaagtg gatgggctgg ataaacactg agactggtga gccaacatat    180
acagatgact tcaagggacg atttgccttc tctttggtga cctctgccac cactgcctat    240
ttgcagatca caaacctcaa caatgaggac acggctacat ttttctgtgc tagattcatc    300
tatgatcctt attgggggtt tgcttactgg ggccagggga ctctggtcac tgtctccgca    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cccaaatc ttgtgacaca    720 cctcccccat gcccacggtg cccagcacct gaggtggct cgagtggagg cggttccgga    780
gggcagcccc gagaaccaca ggtgtacacc ctgcccccat cccgggatga gctgaccaag    840
aaccaggtca gcctgacctg cctggtcaaa ggcttctatc ccagcgacat cgccgtggag    900
tgggagagca atgggcagcc ggagaacaac tacaagacca cgcctcccgt gctggactcc    960
gacggctcct tcttcctcta cagcaagctc accgtggaca agagcaggtg gcagcagggg   1020
aacgtcttct catgctccgt gatgcatgag gctctgcaca accactacac gcagaagagc   1080
ctctccctgt ctccgggttg a                                            1101

<210> SEQ ID NO 34
<211> LENGTH: 366

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34
```

| | | | | | | | | | | | | | | |
|---|---|---|---|---|---|---|---|---|---|---|---|---|---|---|
| Gln | Ile | Gln | Leu | Val | Gln | Ser | Gly | Pro | Glu | Leu | Lys | Lys | Pro | Gly | Glu |
| 1 | | | | 5 | | | | | 10 | | | | | 15 |
| Thr | Val | Lys | Ile | Ser | Cys | Lys | Ala | Ser | Gly | Phe | Thr | Phe | Thr | Asp | Tyr |
| | | | 20 | | | | | 25 | | | | | 30 | | |
| Ser | Ile | His | Trp | Val | Lys | Gln | Ala | Pro | Gly | Lys | Gly | Leu | Lys | Trp | Met |
| | | 35 | | | | | 40 | | | | | 45 | | | |
| Gly | Trp | Ile | Asn | Thr | Glu | Thr | Gly | Glu | Pro | Thr | Tyr | Thr | Asp | Asp | Phe |
| 50 | | | | | 55 | | | | | 60 | | | | | |
| Lys | Gly | Arg | Phe | Ala | Phe | Ser | Leu | Val | Thr | Ser | Ala | Thr | Thr | Ala | Tyr |
| 65 | | | | | 70 | | | | | 75 | | | | | 80 |
| Leu | Gln | Ile | Asn | Asn | Leu | Asn | Asn | Glu | Asp | Thr | Ala | Thr | Phe | Phe | Cys |
| | | | | 85 | | | | | 90 | | | | | 95 | |
| Ala | Arg | Phe | Ile | Tyr | Asp | Pro | Tyr | Trp | Gly | Phe | Ala | Tyr | Trp | Gly | Gln |
| | | | 100 | | | | | 105 | | | | | 110 | | |
| Gly | Thr | Leu | Val | Thr | Val | Ser | Ala | Ala | Ser | Thr | Lys | Gly | Pro | Ser | Val |
| | | 115 | | | | | 120 | | | | | 125 | | | |
| Phe | Pro | Leu | Ala | Pro | Ser | Ser | Lys | Ser | Thr | Ser | Gly | Gly | Thr | Ala | Ala |
| 130 | | | | | 135 | | | | | 140 | | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Lys | Val | Glu | Pro | Lys | Ser | Cys | Asp |
| 210 | | | | | 215 | | | | | 220 | | | | | |
| Lys | Thr | His | Thr | Cys | Pro | Pro | Cys | Pro | Glu | Pro | Lys | Ser | Cys | Asp | Thr |
| 225 | | | | | 230 | | | | | 235 | | | | | 240 |
| Pro | Pro | Pro | Cys | Pro | Arg | Cys | Pro | Ala | Pro | Gly | Gly | Gly | Ser | Ser | Gly |
| | | | | 245 | | | | | 250 | | | | | 255 | |
| Gly | Gly | Ser | Gly | Gly | Gln | Pro | Arg | Glu | Pro | Gln | Val | Tyr | Thr | Leu | Pro |
| | | | 260 | | | | | 265 | | | | | 270 | | |
| Pro | Ser | Arg | Asp | Glu | Leu | Thr | Lys | Asn | Gln | Val | Ser | Leu | Thr | Cys | Leu |
| | | 275 | | | | | 280 | | | | | 285 | | | |
| Val | Lys | Gly | Phe | Tyr | Pro | Ser | Asp | Ile | Ala | Val | Glu | Trp | Glu | Ser | Asn |
| 290 | | | | | 295 | | | | | 300 | | | | | |
| Gly | Gln | Pro | Glu | Asn | Asn | Tyr | Lys | Thr | Thr | Pro | Pro | Val | Leu | Asp | Ser |
| 305 | | | | | 310 | | | | | 315 | | | | | 320 |
| Asp | Gly | Ser | Phe | Phe | Leu | Tyr | Ser | Lys | Leu | Thr | Val | Asp | Lys | Ser | Arg |
| | | | | 325 | | | | | 330 | | | | | 335 | |
| Trp | Gln | Gln | Gly | Asn | Val | Phe | Ser | Cys | Ser | Val | Met | His | Glu | Ala | Leu |
| | | | 340 | | | | | 345 | | | | | 350 | | |
| His | Asn | His | Tyr | Thr | Gln | Lys | Ser | Leu | Ser | Leu | Ser | Pro | Gly | | |
| | | 355 | | | | | 360 | | | | | 365 | | | |

```
<210> SEQ ID NO 35
<211> LENGTH: 1470
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gaggtacaac tggtggagtc tgggggaggc ttagtgaagc ctggagggtc cctgaggctc      60
tcctgtgcag cctctggatt cactttcagt gactattaca tgtattggtt tcgccaggcc     120
ccgggaaagg gctggagtg gtcgcaacc attagtgatg gtggtagtta cacctactat       180
ccagacagtg tgaaggggcg attcaccatc tccagagaca tgccaagaa cagcctctac      240
ctgcagatga gcagcctgag ggctgaggac acagctgtgt attactgcgc aagagaggag     300
aatggtaact tttactactt tgactactgg ggccaaggga ccacggtcac cgtctcctct     360
gggggcgggg ggtccggggg aggcgggtcg ggaggtggcg gaagtgatat ccagatgacc     420
cagtctccat catccttgtc tgcatcggtg ggagacaggg tcactatcac ttgcaaggcg     480
ggtcaggaca ttaaaagcta tttaagctgg taccagcaga accagggaa agcgcctaag      540
cttctgatct attatgcaac aaggttggca gatggggtcc catcaagatt cagtggcagt     600
ggatctggta cagattatac tctaaccatc agcagcctgc agcctgagga tttcgcaact     660
tattactgtc tacagcatgg tgagagcccg tggacgttcg gtggaggcac caagctggag     720
atcaaaggcg gtggagggtc cggtggaggg ggctctggag ggggcggttc aggggggcggt    780
ggatcggggg gaggtggctc ccaacttgtg ctcactcagt catcttcagt ctctttctcc     840
ctgggagcct cagcaaaact cacgtgcacc ttgagtagtc agcacagtac gtacaccatt     900
gaatggtatc agcaacagcc cctcaagcct cctaagtatg tgatggagct taagaaagat     960
ggaagccaca gcacaggtga tgggattcct gatcgcttct ctggatccag ctctggtgct    1020
gatcgctacc ttagcatttc caacatccag cctgaagatg aagcaatata catctgtggt    1080
gtgggtgata caattaagga acaatttgtg tatgttttcg gcggtggaac caaggtcgaa    1140
atcaaacgta cggtggctgc accatctgtc ttcatcttcc cgccatctga tgagcagttg    1200
aaatctggaa ctgcctctgt tgtgtgcctg ctgaataact tctatcccag agaggccaaa    1260
gtacagtgga aggtggataa cgccctccaa tcgggtaact cccaggagag tgtcacagag    1320
caggacagca aggacagcac ctacagcctc agcagcaccc tgacgctgag caaagcagac    1380
tacgagaaac acaaagtcta cgcctgcgaa gtcacccatc agggcctgag ctcgcccgtc    1440
acaaagagct tcaacagggg agagtgttga                                      1470
```

<210> SEQ ID NO 36
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Tyr Trp Phe Arg Gln Ala Pro Gly Lys Gly Leu Glu Trp Val
        35                  40                  45

Ala Thr Ile Ser Asp Gly Gly Ser Tyr Thr Tyr Tyr Pro Asp Ser Val
    50                  55                  60
```

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
            85                  90                  95

Ala Arg Glu Glu Asn Gly Asn Phe Tyr Tyr Phe Asp Tyr Trp Gly Gln
            100                 105                 110

Gly Thr Thr Val Thr Val Ser Ser Gly Gly Gly Gly Ser Gly Gly Gly
            115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Lys Ala
145                 150                 155                 160

Gly Gln Asp Ile Lys Ser Tyr Leu Ser Trp Tyr Gln Gln Lys Pro Gly
                165                 170                 175

Lys Ala Pro Lys Leu Leu Ile Tyr Tyr Ala Thr Arg Leu Ala Asp Gly
                180                 185                 190

Val Pro Ser Arg Phe Ser Gly Ser Gly Ser Gly Thr Asp Tyr Thr Leu
            195                 200                 205

Thr Ile Ser Ser Leu Gln Pro Glu Asp Phe Ala Thr Tyr Tyr Cys Leu
210                 215                 220

Gln His Gly Glu Ser Pro Trp Thr Phe Gly Gly Gly Thr Lys Leu Glu
225                 230                 235                 240

Ile Lys Gly Gly Gly Gly Ser Gly Gly Gly Gly Ser Gly Gly Gly Gly
            245                 250                 255

Ser Gly Gly Gly Gly Ser Gly Gly Gly Gly Ser Gln Leu Val Leu Thr
            260                 265                 270

Gln Ser Ser Ser Val Ser Phe Ser Leu Gly Ala Ser Ala Lys Leu Thr
    275                 280                 285

Cys Thr Leu Ser Ser Gln His Ser Thr Tyr Thr Ile Glu Trp Tyr Gln
290                 295                 300

Gln Gln Pro Leu Lys Pro Pro Lys Tyr Val Met Glu Leu Lys Lys Asp
305                 310                 315                 320

Gly Ser His Ser Thr Gly Asp Gly Ile Pro Asp Arg Phe Ser Gly Ser
                325                 330                 335

Ser Ser Gly Ala Asp Arg Tyr Leu Ser Ile Ser Asn Ile Gln Pro Glu
            340                 345                 350

Asp Glu Ala Ile Tyr Ile Cys Gly Val Gly Asp Thr Ile Lys Glu Gln
                355                 360                 365

Phe Val Tyr Val Phe Gly Gly Gly Thr Lys Val Glu Ile Lys Arg Thr
370                 375                 380

Val Ala Ala Pro Ser Val Phe Ile Phe Pro Pro Ser Asp Glu Gln Leu
385                 390                 395                 400

Lys Ser Gly Thr Ala Ser Val Val Cys Leu Leu Asn Asn Phe Tyr Pro
            405                 410                 415

Arg Glu Ala Lys Val Gln Trp Lys Val Asp Asn Ala Leu Gln Ser Gly
            420                 425                 430

Asn Ser Gln Glu Ser Val Thr Glu Gln Asp Ser Lys Asp Ser Thr Tyr
            435                 440                 445

Ser Leu Ser Ser Thr Leu Thr Leu Ser Lys Ala Asp Tyr Glu Lys His
            450                 455                 460

Lys Val Tyr Ala Cys Glu Val Thr His Gln Gly Leu Ser Ser Pro Val
465                 470                 475                 480

Thr Lys Ser Phe Asn Arg Gly Glu Cys

485

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Ser Ser Gly Gly Gly Ser Gly
 1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Ser Ser Gly Gly Gly Ser Gly Gly
 1               5                   10

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Pro Lys Ser Cys Asp Lys Thr His Thr Cys Pro Pro Cys Pro Ala
 1               5                   10                  15
Pro

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Ser Lys Tyr Gly Pro Pro Cys Pro Ser Cys Pro Ala Pro
 1               5                   10

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Pro Glu Pro Lys Ser Cys Asp Thr Pro Pro Cys Pro Arg
 1               5                   10                  15

<210> SEQ ID NO 42
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 42

Gly Gly Gly Gly Ser Gly Gly Gly Gly Ser
  1               5                  10

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Gly Gly Gly
  1

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Gly Gly Gly Gly Ser Gly Gly Gly Ser Gly Gly Gly Gly Ser
  1               5                  10                  15

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Gly Ser Gly Gly Gly Gly Ser Gly Gly Gly Gly Ser Gly
  1               5                  10                  15

Gly Gly Gly Ser Gly Gly Gly Gly Ser
             20                  25

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Gly Gly Ser
                  5
```

US 8,084,026 B2

MULTISPECIFIC BINDING MOLECULES COMPRISING CONNECTING PEPTIDES

RELATED APPLICATIONS

This application is a continuation application of International Patent Application No. PCT/US2006/000505, filed Jan. 5, 2006, titled "Multispecific Binding Molecules Comprising Connecting Peptides" which claims the benefit of U.S. Ser. No. 60/641,761, titled "Multispecific Binding Molecules Comprising Connecting Peptides" filed on Jan. 5, 2005.

This application is also related to U.S. Ser. No. 60/515,351, titled "Modified Antibody Molecules Comprising Connecting Peptides," filed on Oct. 28, 2003 and to U.S. Ser. No. 60/516,030, titled "Modified Antibody Molecules Comprising Connecting Peptides," filed Oct. 30, 2003. This application is also related to U.S. Ser. No. 10/880,028, titled "Modified Binding Molecules Comprising Connecting Peptides," filed Jun. 28, 2004. This application is also related to U.S. Ser. No. 60/555,805, titled "Receptor Coupling Agents and Therapeutic Uses Thereof" filed on Mar. 23, 2004.

The contents of each of the above applications are incorporated in their entirety by this reference.

BACKGROUND OF THE INVENTION

Antibodies are dimeric molecules; each monomer making up the dimer comprises one light and one heavy chain. Solutions of antibody molecules exist in two forms associated with hinge heterogeneity. Using SDS-PAGE analysis of purified Mab MAb, typically the two forms are observed as two protein bands, a major band (MW approximately 150-160 kDa) and a minor band (MW approximately 75-80 kDa). This latter form is typically observed after SDS-PAGE analysis of purified IgG4 preparations, but can be identified at much lower frequencies in all IgG isotypes, including purified, recombinant MAbs (Angal et al. 1993. *Mol. Immunol.* 30:105; Norderhaug et al. 1990. *Eur. J. Immunol.* 21:2370). The larger molecular weight isoform, referred to as Form A, contains covalent interchain disulfide bonds at positions corresponding to 239 and 242, Kabat numbering system (positions 226 and 229, EU numbering system) (Kabat, E, Wu, T T, Perry, H M, Gottesman, K S, Foeller, C: Sequences of Proteins of Immunological Interest. Bethesda, US Department of Health and Human Services, NIH, 1991). The second isoform, Form B, is thought to contain no covalent linkages between the two heavy chains and an intrachain disulfide bond between the two neighboring cysteine residues as evidenced by the 75-80 kDa seen in non-reducing SDS-PAGE electrophoresis. The two heavy chains of Form B are presumably held together by strong non-covalent (e.g., ionic) interactions associated with the CH3 domain region of the molecule. These mixtures of A and B forms are not present in solutions of MAb fragments that contain an intact hinge, but lack a CH3 domain, such as, for example, F(ab)$_2$ fragments. Typically, genetically engineered or enzymatically digested F(ab)$_2$ MAb preparations lack the B-form, since the molecule lacks the necessary domains for maintaining non-covalent interactions (e.g., hydrogen bonding). However, they are present in MAb preparations that do contain a CH3 domain, such as IgG4, CH2 domain deleted MAb fragments (e.g., as described in 02/060955 A2) and minibodies (see, e.g., Hu et al. 1996. *Cancer Research* 56:3055).

The application of protein engineering techniques to therapeutic antibody design has also produced a number of antibody formats that have been shown to have altered, and in some cases, improved pharmacodynamic, biodistribution, and activity profiles. Some altered antibody molecules have been made in which the number of cysteine residues in the hinge region is reduced to one to facilitate assembly of antibody molecules as it is only necessary to form a single disulfide bond. This also provides a specific target for attaching the hinge region either to another hinge region or to an effector or reporter molecule (U.S. Pat. No. 5,677,425). The number of cysteine residues in the antibody hinge has also been increased (U.S. Pat. No. 5,677,425). Other mutated antibodies have been constructed in which the IgG1 hinge region and the CH2 domain have been replaced with the human IgG3 hinge region (WO 97/11370). These molecules contain 11 sulfhydryl groups for substitution of multiple haptens via thiol groups.

CH2 domain deleted antibodies have a molecular mass of approximately 120 kDa and have been shown to penetrate tumors significantly better than full length IgG. Minibodies, which also have deletion of the CH2 domain, have similar characteristics. These domain deleted molecules accumulate at tumor sites more efficiently than other MAb fragments, such as F(ab)'$_2$s, but without the unfavorable pharmacodynamic profiles seen with intact IgG antibody. CH2 domain deleted antibodies consist of a VLCL light chain and a VH1 heavy chain domain and a portion of the hinge region (e.g., the upper and middle hinge) genetically fused (either directly or through a modified peptide spacer) to a CH3 domain. As an example, the biosynthesis of recombinant CH2 domain deleted ddCC49, a domain deleted antibody that recognizes the tumor associated TAG72 antigen expressed on a variety of human carcinomas, produces the A and B isoforms in approximately 50:50 distribution in cell cultures. Cells engineered to express alternative forms of CH2 domain deleted antibodies, for example, tetravalent CH2 domain deleted antibodies, minibodies, or tetravalent minibodies also express a mixture consisting of A and B isoforms and/or monomeric half-mer molecules.

Form A and Form B are extremely difficult to separate even after MAb purification, since they are composed of identical amino acids and, therefore, have identical molecular weight and similar physical and chemical properties. They cannot be separated by standard gel filtration, affinity chromatography, or ion exchange chromatography typically used to purify antibody molecules, including recombinant MAb proteins. Current manufacturing processes discard at least 50% of the total antibody produced, having a negative impact on overall yield. Moreover, the presence of the two isoforms increases efforts required for downstream processing.

The manufacture of a homogenous preparation of binding molecules is also important where the binding molecules are intended to bind to more than one type of target molecule. Such is the case with multispecific binding molecules which comprise binding sites with variable binding specificities. For example, a single bispecific binding molecule is capable of binding to and/or coupling two distinct target molecules that are not otherwise capable of being targeted by a single agent. To retain the desired bispecificity, it is vital that bispecific dimeric polypeptides are prepared with minimal amount of Form B isoforms or monomeric half-mer molecules, as these contaminants lack the desired activity of a bispecific binding molecule. Accordingly, methods which facilitate the preferential manufacture of Form A isoforms of bispecific binding molecules would be of great benefit.

SUMMARY OF THE INVENTION

The invention is based, at least in part, on the finding that in a composition comprising a mixture of multispecific dimeric polypeptide binding molecules comprising different isoforms (molecules comprising two heavy chain portions in which a fraction of the binding molecules comprise two heavy chain portions that are linked via at least one interchain disulfide linkage (Form A) and a portion of the multispecific binding molecules comprise two heavy chain portions that are not linked via at least one interchain disulfide linkage (Form B)) one form or the other can be preferentially obtained, e.g., by separation using hydrophobic interaction chromatography or by inclusion of synthetic connecting peptides which result in the preferential biosynthesis of either Form A or Form B.

In particular, the instant invention is especially useful in producing multispecific molecules which are capable of binding to at least two target molecules. Preferably, at least one of the first and second target molecules to which a multispecific binding molecule of the invention binds is a member of the TNF family of receptors ("TNFRs"). In one embodiment, at least one of the first and second target molecules to which a multispecific binding molecule of the invention binds is a tumor cell antigen. In another exemplary embodiment, the first and second target molecules to which a multispecific binding molecule of the invention binds are both TNFRs. A limiting factor in the treatment of tumors with monospecific TNFR binding molecules is that often only a subset of tumors appear to be sensitive to such therapies. Multispecific TNFR binding molecules can specifically activate TNFRs, and enhance receptor signaling by, for example, bringing the TNFRs into close proximity. The invention provides improved multispecific TNFR binding molecules which can target more than one TNFR or TNFR type and enhance signaling, thus providing an improved method of treating disorders such as cancer.

Accordingly, in a first aspect, the invention is directed to a composition comprising multispecific dimeric binding molecules said molecules comprising:
 a) at least a first binding site specific for a tumor necrosis factor (TNF) receptor family member or a ligand of a TNF receptor family member and at least a second binding site; and
 b) at least two polypeptide chains comprising at least one heavy chain portion and a synthetic connecting peptide;
wherein greater than about 50% of the dimeric binding molecules comprise polypeptide chains that are linked via at least one interchain disulfide linkage.

In certain embodiments, the first binding site comprises an anti-TNF receptor family member antigen binding site. In other embodiments, the first binding site comprises a receptor binding portion of a ligand that binds to a TNF receptor family member.

In other embodiments, the second binding site is individually selected from the group consisting of: an antigen binding site and a ligand binding portion of a receptor.

In one embodiment, the first and second binding sites are both specific for one or more TNF receptor family members or one or more TNF ligand family member. In another embodiment, the first binding site is specific for a TNF receptor family member or a TNF ligand family member and the second binding site is specific for a cell surface molecule. In one embodiment, the first and second binding sites bind to different epitopes of the same TNF receptor family member or TNF ligand family member. In another embodiment, the first and second binding sites bind to two different TNF receptor family members or two different TNF ligand family members.

In another embodiment, the first binding site is specific for a TNF receptor family member or a TNF ligand family member and the second binding site is specific for a soluble molecule. In one embodiment, the soluble molecule is a soluble ligand.

In certain embodiments, the soluble ligand is selected from the group consisting of a hormone, a cytokine, a chemokine, a clotting factor, and a growth factor. In an exemplary embodiment, the soluble ligand is a TNF ligand family member.

In one embodiment, the cell surface molecule is a cell-surface receptor. In certain embodiments, the cell-surface receptor is selected from the group consisting of: a hormone receptor, a growth factor receptor, a cytokine receptor, and a cell adhesion molecule. In preferred embodiments, the cell surface molecule is a tumor cell antigen. In exemplary embodiments, the binding site is derived from an antibody selected from the group consisting of: 2B8, Lym 1, Lym 2, LL2, Her2, B1, MB1, BH3, B4, B72.3, CC49, 5E8, B3F6, and 5E10.

In an exemplary embodiment, the TNF ligand family member is selected from the group consisting of TNF-alpha, LT-alpha, FasL, APO-3L, TRAIL, RANKL, EDAR1 ligand, XEDAR ligand, Fn14 ligand, Troy/Trade ligand, NGF-β, NGF-2/NTF3, NTF5, BDNF, IFRD1, HVEM ligand, CD27L, CD30L, CD40L, 4-1BB-L, OX40L, GITRL, and BAFF.

In another exemplary embodiment, at least one binding site binds to a TNF receptor family member containing a death domain. In a more specific embodiment, the TNF receptor family member is selected from the group consisting of: TNFR1, Fas-R, DR-3, TRAIL-R1, TRAIL-R2, and DR6. In another exemplary embodiment, at least one binding site binds to a TNF receptor family member lacking a death domain. In one embodiment, the TNF receptor lacking a death domain is involved in tissue differentiation. In a more specific embodiment, the TNF receptor involved in tissued differentiation is selected from the group consisting of LTβR, RANK, EDAR1, XEDAR, Fn14, Troy/Trade, and NGFR. In another embodiment, the TNF receptor lacking a death domain is involved in immune regulation. In a more specific embodiment, TNF receptor family member involved in immune regulation is selected from the group consisting of TNFR2, HVEM, CD27, CD30, CD40, 4-1BB, OX40, and GITR.

In certain embodiments, the binding molecules are fusion proteins. In other embodiments, the binding molecules are antibody molecules. In one embodiment, the antibody molecules are domain-deleted antibodies. In another embodiment the antibody molecules are CH2 domain-deleted antibodies.

In certain embodiments, the multivalent binding molecules of the invention comprise four binding sites. In an exemplary embodiment, the multivalent binding molecules are scFv tetravalent minibody molecules. In another exemplary embodiment, the multivalent binding molecules are scFv2 tetravalent antibody molecules. In yet another exemplary embodiment, the multivalent binding molecules are diabodies.

In other embodiments, greater than about 90% of the multispecific dimeric binding molecules of the invention comprise polypeptide chains that are linked via at least one interchain disulfide linkage. In other embodiments, the polypeptide chains are linked via two or more interchain disulfide linkages.

In other embodiments, multispecific dimeric binding molecules of the invention comprise polypeptide chains lacking all or part of a CH2 domain.

In other embodiments, the compositions of the invention comprise a synthetic connecting peptide comprising a proline residue at position 243, Kabat numbering system. In another embodiment, the synthetic connecting peptide further comprises an alanine residue at position 244 and a proline residue at position 245, Kabat numbering system.

In other embodiments, the compositions of the invention comprise a synthetic connecting peptide comprising a chimeric hinge. In one embodiment, the synthetic connecting peptide comprises at least a portion of an IgG1 hinge domain and at least a portion of an IgG3 hinge domain.

In other embodiments, the compositions of the invention comprise an amino acid sequence selected from the group consisting of: SEQ ID NOs: 7-15 and 23.

In a second aspect, the invention is directed to a composition comprising dimeric multispecific binding molecules said molecules comprising:
 a) at least a first binding site specific for LTβR and at least a second binding site specific for TRAIL-R2; and
 b) at least two polypeptide chains comprising at least one heavy chain portion and a synthetic connecting peptide;
wherein greater than about 50% of the dimers comprise polypeptide chains that are linked via at least one interchain disulfide linkage.

In certain embodiments, the binding molecules are fusion proteins. In other embodiments, the binding molecules are antibody molecules. In one embodiment, the antibody molecules are domain-deleted antibodies. In another embodiment the antibody molecules are CH2 domain-deleted antibodies.

In certain embodiments, the multivalent binding molecules of the invention comprise four binding sites. In another embodiment, the binding molecules comprise two binding sites specific for LTβR and two binding sites specific for TRAIL-R2.

In one embodiment, the binding molecules are scFv tetravalent minibody molecules. In an exemplary embodiment, the binding molecules C-scFv tetravalent minibody molecules. In another exemplary embodiment, the binding molecules are $N_H$-scFv tetravalent minibody molecules. In yet another exemplary embodiment, the binding molecules are $N_L$-scFv tetravalent minibody molecules.

In another embodiment, the multivalent binding molecules are diabodies.

In another embodiment, the binding molecules are sc(Fv)2 tetravalent antibody molecules. In one embodiment, the binding molecules are C-scFv tetravalent antibody molecules. In an exemplary embodiment, the binding molecules are C-scFv tetravalent antibodies comprising at least one heavy chain portion comprising the amino acid sequence shown in FIG. 10B (SEQ ID NO: 26). In another exemplary embodiment, the binding molecules are C-scFv tetravalent antibodies comprising at least one light chain portion comprising the amino acid sequence shown in FIG. 11B (SEQ ID NO: 28). In another embodiment, the binding molecules are $N_H$-scFv tetravalent antibody molecules. In an exemplary embodiment, the binding molecules are $N_H$-scFv tetravalent antibodies comprising at least one heavy chain portion comprising the amino acid sequence shown in FIG. 12B (SEQ ID NO: 30). In another exemplary embodiment, the binding molecules are $N_H$-scFv tetravalent antibodies comprising at least one light chain portion comprising the amino acid sequence shown in FIG. 13B (SEQ ID NO: 32). In yet another embodiment, the binding molecules are $N_L$-scFv tetravalent antibody molecules. In an exemplary embodiment, the binding molecules are $N_L$-scFv tetravalent antibodies comprising at least one heavy chain portion comprising the amino acid sequence shown in FIG. 14B (SEQ ID NO: 34). In another exemplary embodiment, the binding molecules are $N_L$-scFv tetravalent antibodies comprising at least one light chain portion comprising the amino acid sequence shown in FIG. 15B (SEQ ID NO: 36).

In certain embodiments, greater than about 90% of the multispecific dimeric binding molecules of the invention comprise polypeptide chains that are linked via at least one interchain disulfide linkage. In other embodiments, the polypeptide chains are linked via two or more interchain disulfide linkages.

In other embodiments, multispecific dimeric binding molecules of the invention comprise polypeptide chains lacking all or part of a CH2 domain.

In other embodiments, the compositions of the invention comprise a synthetic connecting peptide comprising a proline residue at position 243, Kabat numbering system. In another embodiment, the synthetic connecting peptide further comprises an alanine residue at position 244 and a proline residue at position 245, Kabat numbering system.

In other embodiments, the compositions of the invention comprise a synthetic connecting peptide comprising a chimeric hinge. In one embodiment, the synthetic connecting peptide comprises at least a portion of an IgG1 hinge domain and at least a portion of an IgG3 hinge domain.

In other embodiments, the compositions of the invention comprise an amino acid sequence selected from the group consisting of: SEQ ID NOs: 7-15 and 23.

In a third aspect, the invention provides a method of treating a subject that would benefit from treatment with an antigen binding molecule comprising administering a composition of the invention such that treatment occurs. In one embodiment, the subject is suffering from cancer. In another embodiment, the subject is suffering from lymphoma.

In a fourth aspect, the invention provides nucleic acid molecules encoding the dimeric polypeptide binding molecules of the invention, as well as vectors and host cells comprising said nucleic acid molecules. In one embodiment, the nucleic acid molecule comprises the nucleotide sequence shown in FIG. 10A (SEQ ID NO:25). In another embodiment, the nucleic acid molecule comprises the nucleotide sequence shown in FIG. 11A (SEQ ID NO:27). In another embodiment, the nucleic acid molecule comprises the nucleotide sequence shown in FIG. 12A (SEQ ID NO:29). In another embodiment, the nucleic acid molecule comprises the nucleotide sequence shown in FIG. 13A (SEQ ID NO:31). In another embodiment, the nucleic acid molecule comprises the nucleotide sequence shown in FIG. 14A (SEQ ID NO:33). In another embodiment, the nucleic acid molecule comprises the nucleotide sequence shown in FIG. 15A (SEQ ID NO:35).

BRIEF DESCRIPTION OF THE DRAWINGS

FIG. 9 shows a schematic diagram of a four chain tetravalent scFv CH2 domain deleted bispecific antibody ($N_L$-scFv tetravalent CH2 domain deleted bispecific antibody) comprising a scFv appended to the amino terminus of VL and comprising a hinge connecting peptide. Each heavy chain portion of the bispecific antibody contains an Fv region with binding specificity for the TRAIL R2 antigen and a scFv region with binding specificity for the LTβR antigen. The orientation of the VH and VL domains in the scFv may be changed and the respective antigen binding specificities may be altered.

FIG. 10A (SEQ ID NO:25) shows the single-stranded DNA sequence of a heavy chain CH2 domain-deleted sc(Fv)2 tetravalent (C-scFv tetravalent CH2 domain deleted) anti-LTBR×anti-TRAIL bispecific antibody gene containing the synthetic G1/G3:/Pro243Ala244Pro245+[Gly/Ser] hinge connecting peptide. FIG. 10B (SEQ ID NO:26) shows the corresponding amino acid sequence of heavy chain CH2 domain-deleted sc(Fv)2 tetravalent (C-scFv tetravalent CH2 domain deleted) anti-LTBR×anti-TRAIL bispecific antibody.

FIG. 11A (SEQ ID NO:27) single-stranded DNA sequence of light chain CH2 domain-deleted sc(Fv)2 tetravalent (C-scFv tetravalent CH2 domain deleted) anti-LTBR×anti-TRAIL bispecific antibody gene. FIG. 11B (SEQ ID NO:28) shows the corresponding amino acid sequence of the light chain CH2 domain-deleted sc(Fv)2 tetravalent (C-scFv tetravalent CH2 domain deleted) anti-LTBR×anti-TRAIL bispecific antibody gene.

FIG. 12A (SEQ ID NO:29) shows the single-stranded DNA sequence of heavy chain CH2 domain-deleted sc(Fv)2 tetravalent ($N_H$-scFv tetravalent CH2 domain deleted) anti-LTBR×anti-TRAIL bispecific antibody gene containing the synthetic G1/G3:/Pro243Ala244Pro245+[Gly/Ser] hinge connecting peptide. FIG. 12B (SEQ ID NO:30) shows the corresponding amino acid sequence of heavy chain CH2 domain-deleted sc(Fv)2 tetravalent (C-scFv tetravalent CH2 domain deleted) anti-LTBR×anti-TRAIL bispecific antibody.

FIG. 13A (SEQ ID NO:31) shows the single-stranded DNA sequence of light chain CH2 domain-deleted sc(Fv)2 tetravalent ($N_H$-scFv tetravalent CH2 domain deleted) anti-LTBR×anti-TRAIL bispecific antibody gene. FIG. 13B (SEQ ID NO:32) shows the corresponding amino acid sequence of light chain CH2 domain-deleted sc(Fv)2 tetravalent (C-scFv tetravalent C2 domain deleted) anti-LTBR×anti-TRAIL bispecific antibody gene.

FIG. 14A (SEQ ID NO:33) shows the single-stranded DNA sequence of heavy chain CH2 domain-deleted sc(Fv)2 tetravalent ($N_L$-scFv tetravalent CH2 domain deleted) anti-LTBR×anti-TRAIL bispecific antibody gene containing the synthetic G1/G3:/Pro243Ala244Pro245+[Gly/Ser] hinge connecting peptide. FIG. 14B (SEQ ID NO:34) shows the corresponding amino acid sequence of heavy chain CH2 domain-deleted sc(Fv)2 tetravalent (C-scFv tetravalent CH2 domain deleted) anti-LTBR×anti-TRAIL bispecific antibody.

Figure 1:
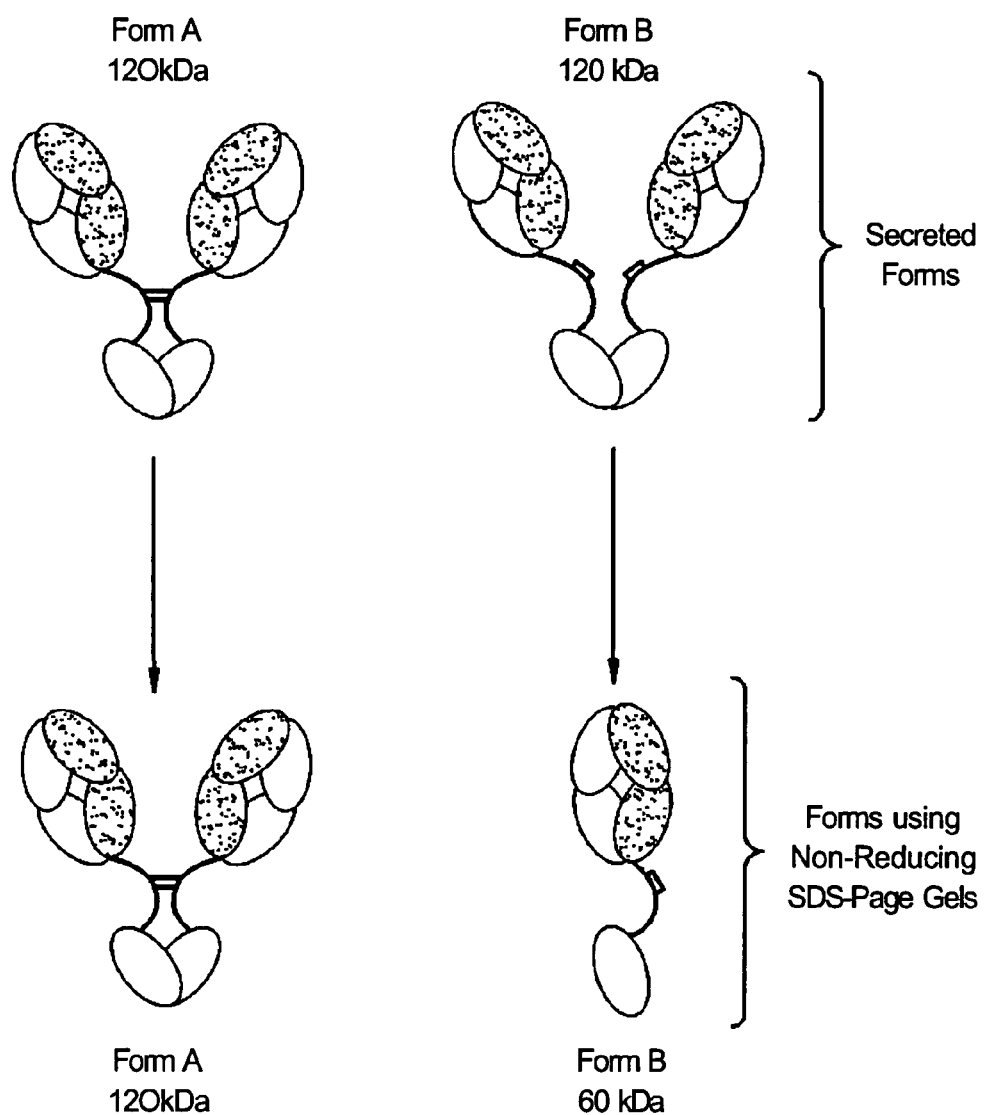
FIG. 1 shows Form A which appears as a 120 kDa dimer and Form B which appears as a 60 kDa monomer in domain deleted antibodies.

FIG. 15A (SEQ ID NO:35) shows the single-stranded DNA sequence of light chain CH2 domain-deleted sc(Fv)2 tetravalent ($N_L$-scFv tetravalent CH2 domain deleted) anti-LTBR×anti-TRAIL bispecific antibody gene. FIG. 15B (SEQ ID NO:36) shows the corresponding amino acid sequence of light chain CH2 domain-deleted sc(Fv)2 tetravalent (C-scFv tetravalent CH2 domain deleted) anti-LTBR×anti-TRAIL bispecific antibody gene.

DETAILED DESCRIPTION OF THE INVENTION

Human immunoglobulins (Igs), including monoclonal antibodies (MAbs), can exist in two forms that are associated with hinge heterogeneity. In native solutions, both of these forms are present as dimeric proteins (each monomer comprising one heavy chain and one light chain). One immunoglobulin molecule comprises a stable four chain construct of approximately 150-160 kDa in which the dimers are held together by an interchain heavy chain disulfide bond (Form A) and one comprises form in which the dimers are not linked via interchain disulfide bonds (Form B). Form B also forms a stable dimer under native conditions, but can be identified under denaturing, non-reducing conditions, in which the heavy chains dissociate yielding a 75-80 kDa molecule. These forms have been extremely difficult to separate, even after MAb affinity purification.

The frequency of appearance of the B form in various intact IgG isotypes is due to, but not limited to, structural differences associated with the hinge region isotype of the MAb molecule. In fact, a single amino acid substitution in the hinge region of the human IgG4 hinge can significantly reduce the appearance of the B form (Angal et al. 1993. Molecular Immunology 30:105) to levels typically observed using a human IgG1 hinge. However, applying this same amino acid substitution to MAb fragments in which the CH3 domain was retained did not eliminate Form B from preparations. Typically, all recombinant CH2 domain deleted antibodies produced in cell cultures often result in hinge heterogeneity which is not corrected via similar molecular mutations in the hinge.

The instant invention advances the state of the art by providing methods of, e.g., separating a first dimeric polypeptide from a second dimeric polypeptide wherein the first and second polypeptides comprise at least two polypeptide chains and at least two of the polypeptide chains comprise at least one heavy chain portion. In one embodiment, the polypeptides of the invention lack all or part of a CH2 domain. The monomers are linked via at least one interchain disulfide linkage (referred to herein as "Form A") and the monomers of the second polypeptide are not linked via at least one interchain disulfide linkage (referred to herein as "Form B"). These forms can be separated from each other using hydrophobic interaction chromatography. In addition, the invention pertains to polypeptides that comprise connecting peptides. The inclusion of certain connecting peptides results in the preferential biosynthesis of polypeptide dimers comprising polypeptide chains that are linked via at least one interchain disulfide linkage or that are not linked via at least one interchain disulfide linkage.

The instant invention is especially useful in producing multispecific, e.g., bispecific molecules. Preferably, at least one of the first and second target molecules to which a bispecific binding molecule of the invention binds is a member of the TNF family of receptors ("TNFRs"). In another exemplary embodiment, the first and second target molecules to which a bispecific binding molecule of the invention binds are both TNFRs. A limiting factor in the treatment of tumors with monospecific TNFR binding molecules is that often only a subset of tumors appears to be sensitive to such therapies. Multispecific TNFR binding molecules can specifically activate TNFRs, and enhance receptor signaling by, for example, bringing the TNFRs into close proximity. The invention provides multispecific TNFR binding molecules which can target more than one TNFR or TNFR type and enhance signaling, thus providing an improved method of treating cancer. As such, multispecific TNFR binding molecules can deliver stronger or more complex signaling, and are, therefore, more effective on a wider range of tumors. In one embodiment, the multispecific TNFR binding molecule increases the signal strength by binding to two or more TNFRs of the same type increasing the number of TNFRs being brought together. In another more preferred embodiment, the multispecific TNFR binding molecule is capable of binding to two different receptors of the TNF family, forming novel heteromeric receptor complexes that embody novel signaling characteristics and/or relocalize a receptor into an environment where signaling is more, or less, effective.

Before further description of the invention, for convenience, certain terms are described below:

I. Definitions

The polypeptides of the invention are binding molecules, i.e., polypeptide molecules or the nucleic acid molecules that encode them, that comprise at least one binding domain which comprises a binding site that specifically binds to a target molecule (such as an antigen or binding partner). For example, in one embodiment, a binding molecule of the invention comprises an immunoglobulin antigen binding site or the portion of a receptor molecule responsible for ligand binding or the portion of a ligand molecule that is responsible for receptor binding. The binding molecules of the invention are polypeptides or the nucleic acid molecules which encode them.

In one embodiment, the binding molecules comprise at least two binding sites. In one embodiment, the binding molecules comprise two binding sites. In one embodiment, the binding molecules comprise three binding sites. In another embodiment, the binding molecules comprise four binding sites.

The polypeptides of the invention are multimers. For example, in one embodiment, the polypeptides of the invention are dimers. In one embodiment, the dimers of the invention are homodimers, comprising two identical monomeric subunits. In another embodiment, the dimers of the invention are heterodimers, comprising two non-identical monomeric subunits. The subunits of the dimer may comprise one or more polypeptide chains. For example, in one embodiment, the dimers comprise at least two polypeptide chains. In one embodiment, the dimers comprise two polypeptide chains. In another embodiment, the dimers comprise four polypeptide chains (e.g., as in the case of antibody molecules).

The polypeptides of the invention comprise at least one amino acid sequence derived from an immunoglobulin domain. A polypeptide or amino acid sequence "derived from" a designated protein refers to the origin of the polypeptide. Preferably, the polypeptide or amino acid sequence which is derived from a particular starting polypeptide or amino acid sequence has an amino acid sequence that is essentially identical to that of the starting sequence, or a portion thereof wherein the portion consists of at least 10-20 amino acids, preferably at least 20-30 amino acids, more preferably at least 30-50 amino acids, or which is otherwise identifiable to one of ordinary skill in the art as having its origin in the starting sequence.

Preferred binding polypeptides comprise an amino acid sequence derived from a human amino acid sequence. However, binding polypeptides may comprise one or more amino acids from another mammalian species. For example, a primate heavy chain portion, hinge portion, or binding site may be included in the subject binding polypeptides and/or connecting polypeptides. Alternatively, one or more murine amino acids may be present in a binding polypeptide, e.g., in an antigen binding site of a binding molecule. Preferred binding molecules of the invention are not immunogenic.

It will also be understood by one of ordinary skill in the art that the binding molecules of the invention (e.g., the heavy chain or light chain portions or binding portions of the subject polypeptides) may be modified such that they vary in amino acid sequence from the naturally occurring immunoglobulin molecule from which they were derived. For example, nucleotide or amino acid substitutions leading to conservative substitutions or changes at "non-essential" amino acid residues may be made.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into polypeptides of the invention and screened for their ability to bind to the desired antigen.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, a polypeptide of the invention comprises a polypeptide chain comprising a CH1 domain, at least a portion of a hinge domain, and a CH2 domain. In another embodiment, a polypeptide of the invention comprises a polypeptide chain comprising a CH1 domain and a CH3 domain. In another embodiment, a polypeptide of the invention comprises a polypeptide chain comprising a CH1 domain, at least a portion of a hinge domain, and a CH3 domain. In another embodiment, a polypeptide of the invention comprises a polypeptide chain comprising a CH3 domain. In one embodiment, a polypeptide of the invention lacks at least a portion of a CH2 domain (e.g., all or part of a CH2 domain). In another embodiment, a polypeptide of the invention comprises a complete Ig heavy chain. As set forth above, it will be understood by one of ordinary skill in the art that these domains (e.g., the heavy chain portions) may be modified such that they vary in amino acid sequence from the naturally occurring immunoglobulin molecule.

In one embodiment, at least two of the polypeptide chains of a binding molecule of the invention comprise at least one heavy chain portion derived from an antibody or immunoglobulin molecule. In one embodiment, at least two heavy chain portions of a polypeptide of the invention are present on different polypeptide chains and interact, e.g., via at least one disulfide linkage (Form A) or via non-covalent interactions (Form B) to form a dimeric polypeptide, each monomer of the dimer comprising at least one heavy chain portion.

In one embodiment, the heavy chain portions of one polypeptide chain of a dimer are identical to those on a second polypeptide chain of the dimer. In one embodiment, the monomers (or half-mers) of a dimer of the invention are identical to each other. In another embodiment, they are not identical. For example, each monomer may comprise a different target binding site.

In one embodiment, a dimer of the invention is held together by covalent interactions, e.g., disulfide bonds. In one embodiment, a dimer of the invention is held together by one or more disulfide bonds. In another embodiment, a dimer of the invention is held together by one or more, preferably two disulfide bonds. In another embodiment, a dimer of the invention is held together by one or more, preferably three disulfide bonds. In another embodiment, a dimer of the invention is held together by one or more, preferably four disulfide bonds. In another embodiment, a dimer of the invention is held together by one or more, preferably five disulfide bonds. In another embodiment a dimer of the invention is held together by one or more, preferably six disulfide bonds. In another embodiment, a dimer of the invention is held together by one or more, preferably seven disulfide bonds. In another embodiment, a dimer of the invention is held together by one or more, preferably eight disulfide bonds. In another embodiment, a dimer of the invention is held together by one or more, preferably nine disulfide bonds. In another embodiment, a dimer of the invention is held together by one or more, preferably ten disulfide bonds. In a further embodiment, a dimer of the invention is not held together by disulfide bonds, but is held together, e.g., by non-covalent interactions.

The heavy chain portions of a polypeptide may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule. As used herein, the term "light chain portion" includes amino acid sequences derived from an immunoglobulin light chain. Preferably, the light chain portion comprises at least one of a VL or CL domain.

In one embodiment a polypeptide of the invention comprises an amino acid sequence or one or more moieties not derived from an Ig molecule. Exemplary modifications are described in more detail below. For example, in one embodiment, a polypeptide of the invention may comprise a flexible linker sequence. In another embodiment, a polypeptide may be modified to add a functional moiety (e.g., PEG, a drug, or a label).

In one embodiment, a binding polypeptide of the invention is a fusion protein. Fusion proteins are chimeric molecules which comprise a binding domain comprising at least one target binding site and at least one heavy chain portion. In one embodiment, a fusion protein further comprises a synthetic connecting peptide.

A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric polypeptides include fusion proteins and the chimeric hinge connecting peptides of the invention.

The term "heterologous" as applied to a polynucleotide or a polypeptide, means that the polynucleotide or polypeptide is derived from a genotypically distinct entity from that of the rest of the entity to which it is being compared. For instance, a heterologous polynucleotide or antigen may be derived from a different species origin, different cell type, or the same type of cell of distinct individuals.

The term "ligand binding domain" or "ligand binding portion of a receptor" as used herein refers to any native receptor (e.g., cell surface receptor) or any region or derivative thereof retaining at least a qualitative ligand binding ability, and preferably the biological activity of a corresponding native receptor.

The term "receptor binding domain" or "receptor binding portion of a ligand" as used herein refers to any native ligand or any region or derivative thereof retaining at least a qualitative receptor binding ability, and preferably the biological activity of a corresponding native ligand.

In one embodiment, a binding molecule of the invention is a fusion protein. A fusion protein of the invention is a chimeric molecule that comprises a binding domain (which comprises at least one binding site) and a dimerization domain (which comprises at least one heavy chain portion). The heavy chain portion may be from any immunoglobulin, such as IgG1, IgG2, IgG3, or IgG4 subtypes, IgA, IgE, IgD or IgM.

In another embodiment of the invention, a binding molecule is an "antibody-fusion protein chimera." Such molecules comprise a molecule which combines at least one binding domain of an antibody with at least one fusion protein. Preferably, the interface between the two polypeptides is a CH3 domain of an immunoglobulin molecule.

In one embodiment, the binding molecules of the invention are "antibody" or "immunoglobulin" molecules, e.g., naturally occurring antibody or immunoglobulin molecules or genetically engineered antibody molecules that bind antigen in a manner similar to antibody molecules. As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "immunoglobulin" comprises five distinct classes of antibody that can be distinguished biochemically. All five classes of antibodies are clearly within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains.

As used herein, the term "binding site" or "binding domain" comprises a region of a polypeptide which is responsible for selectively binding to a target molecule of interest (e.g. an antigen, ligand, receptor, substrate or inhibitor).

Exemplary binding domains include an antibody variable domain, a receptor binding domain of a ligand, a ligand binding domain of a receptor or an enzymatic domain.

In one embodiment, the binding molecules have at least one binding site specific for a molecule targeted for reduction or elimination, e.g., a cell surface antigen or a soluble antigen.

In preferred embodiments, the binding domain is an antigen binding site. An antigen binding site is formed by variable regions that vary from one polypeptide to another. In one embodiment, the polypeptides of the invention comprise at least two antigen binding sites. As used herein, the term "antigen binding site" includes a site that specifically binds (immunoreacts with) an antigen (e.g., a cell surface or soluble antigen). The antigen binding site includes an immunoglobulin heavy chain and light chain variable region and the binding site formed by these variable regions determines the specificity of the antibody. In one embodiment, an antigen binding molecule of the invention comprises at least one heavy or light chain CDR of an antibody molecule (e.g., the sequence of which is known in the art or described herein). In another embodiment, an antigen binding molecule of the invention comprises at least two CDRs from one or more antibody molecules. In another embodiment, an antigen binding molecule of the invention comprises at least three CDRs from one or more antibody molecules. In another embodiment, an antigen binding molecule of the invention comprises at least four CDRs from one or more antibody molecules. In another embodiment, an antigen binding molecule of the invention comprises at least five CDRs from one or more antibody molecules. In another embodiment, an antigen binding molecule of the invention comprises at least six CDRs from one or more antibody molecules. Exemplary antibody molecules comprising at least one CDR that can be included in the subject antigen binding molecules are known in the art and exemplary molecules are described herein.

The polypeptides comprising two heavy chain portions disclosed herein may be linked to form two associated Ys so there will be four binding sites forming a "tetravalent" molecule (see e.g., WO02/096948A2)). In another embodiment, tetravalent minibodies or domain deleted antibodies can be made.

The term "multispecific" includes binding molecules having specificity for more than one target antigen. Such molecules have more than one binding site where each binding site specifically binds (e.g., immunoreacts with) a different target molecule or a different antigenic site on the same target.

In one embodiment, a multispecific binding molecule of the invention is a bispecific molecule (e.g., antibody, minibody, domain deleted antibody, or fusion protein) having binding specificity for at least two targets, e.g., more than one target molecule or more than one epitope on the same target molecule. In one embodiment, a bispecific molecule has at least one binding site specific for a molecule targeted for reduction or elimination and a target molecule on a cell. In another embodiment, a bispecific molecules has at least one target binding site specific for a molecule targeted for reduction or elimination and at least one binding site specific for a drug. In yet another embodiment, a bispecific molecule has at least one binding site specific for a molecule targeted for reduction or elimination and at least one binding site specific for a prodrug.

In one embodiment, a bispecific molecule comprises one specificity for a soluble molecule and one specificity for a cell surface molecule. In another embodiment, a bispecific molecule has two binding specificities for two targets present on one or more soluble molecules. In another embodiment, a bispecific molecule has two binding specificities for two targets present on one or more cell surface molecules.

In a preferred embodiment, a bispecific molecule is a tetravalent antibody that has four binding sites. A tetravalent bispecific molecule may is bivalent for each specificity. Further description of bispecific molecules is provided below.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen).

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system, Kabat E A et al. Sequences of Proteins of Immunological Interest. Bethesda, US Department of Health and Human Services, NIH. 1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083).

In one embodiment, a binding molecule of the invention comprises a connecting peptide. The connecting peptides of the invention are synthetic. As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

Connecting peptides of the invention connect two domains (e.g., a binding domain and a dimerization domain) of a binding molecule of the invention. For example, connecting peptides connect a heavy chain portion to a binding domain comprising a binding site. In one embodiment, a connecting peptide connects two heavy chain constant region domains, such as CH1 and CH2 domains; CH1 and CH3 domains; hinge and CH1 domains; hinge and CH3 domains; VH and hinge domains, or a CH3 domain and a non-immunoglobulin polypeptide) in a linear amino acid sequence of a polypeptide chain. Preferably, such connecting peptides provide flexibility to the polypeptide molecule and facilitate dimerization via disulfide bonding. In one embodiment, the connecting peptides of the invention are used to replace one or more heavy chain domains (e.g., at least a portion of a constant region domain (e.g., at least a portion of a CH2 domain) and/or at least a portion of the hinge region (e.g., at least a portion of the lower hinge region domain) in a domain deleted construct). For example, in one embodiment, a VH domain is fused to a CH3 domain via a connecting peptide (the C-terminus of the connecting peptide is attached to the N-terminus of the CH3 domain and the N-terminus of the connecting peptide is attached to the C-terminus of the VH domain). In another embodiment, a VL domain is fused to a CH3 domain via a connecting peptide (the C-terminus of the connecting peptide is attached to the N-terminus of the CH3 domain and the N-terminus of the connecting peptide is attached to the C-terminus of the VL domain. In another embodiment, a CH1 domain is fused to a CH3 domain via a connecting peptide (the C-terminus of the connecting peptide is attached to the N-terminus of the CH3 domain and the N-terminus of the connecting peptide is attached to the C-terminus of the CH1 domain).

In one embodiment, a synthetic connecting peptide comprises a portion of a constant region domain. For example, in one embodiment, a connecting peptide that replaces a CH2 domain can comprise a portion of the CH2 domain.

In one embodiment, a connecting peptide comprises or consists of a gly-ser linker. As used herein, the term "gly-ser linker" refers to a peptide that consists of glycine and serine residues An exemplary gly/ser linker comprises the amino acid sequence GGGSSGGGSG (SEQ ID NO:1). In one embodiment, a connecting peptide of the invention comprises at least a portion of an upper hinge region (e.g., derived from an IgG1, IgG3, or IgG4 molecule), at least a portion of a middle hinge region (e.g., derived from an IgG1, IgG3, or IgG4 molecule) and a series of gly/ser amino acid residues (e.g., a gly/ser linker such as GGGSSGGGSG (SEQ ID NO:1)). In one embodiment, the connecting peptide comprises a substitution of one or more amino acids as compared to naturally occurring IgG1 or IgG3 hinge regions. In another embodiment, a connecting-peptide comprises an amino acid sequence such as described in WO 02/060955. Connecting peptides are described in more detail below.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

It is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In one embodiment, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate compliment binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. More generally, those skilled in the art will realize that antibodies modified as described herein may exert a number of subtle effects that may or may not be readily appreciated. However the resulting physiological profile, bioavailability and other biochemical effects of the modifications, such as tumor localization, biodistribution and serum half-life, may easily be measured and quantified using well know immunological techniques without undue experimentation.

In one embodiment, modified forms of antibodies can be made from a whole precursor or parent antibody using techniques known in the art. Exemplary techniques are discussed in more detail below. In particularly preferred embodiments both the variable and constant regions of polypeptides of the invention are human. In one embodiment, fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make antibodies are described in U.S. Pat. Nos. 6,150,584; 6,458,592; 6,420,140. Other techniques are known in the art.

A polypeptide comprising a heavy chain portion may or may not comprise other amino acid sequences or moieties not derived from an immunoglobulin molecule. Such modifications are described in more detail below. For example, in one embodiment, a polypeptide of the invention may comprise a flexible linker sequence. In another embodiment, a polypeptide may be modified to add a functional moiety such as PEG.

The polypeptides of the instant invention comprise at least two binding sites that provide for the association of the polypeptide with the selected target molecule.

In one embodiment, a binding molecule of the invention comprises an antibody molecule, e.g., an intact antibody molecule, or a fragment of an antibody molecule. In another embodiment, binding molecule of the invention is a modified or synthetic antibody molecule. In one embodiment, a binding molecule of the invention comprises all or a portion of (e.g., at least one antigen binding site from, at least one CDR from, or at least one heavy chain portion from) a monoclonal antibody, a humanized antibody, a chimeric antibody, or a recombinantly produced antibody.

In embodiments where the binding molecule is an antibody or modified antibody, the antigen binding site and the heavy chain portions need not be derived from the same immunoglobulin molecule. In this regard, the variable region may or be derived from any type of animal that can be induced to mount a humoral response and generate immunoglobulins against the desired antigen. As such, the variable region of the polypeptides may be, for example, of mammalian origin e.g., may be human, murine, non-human primate (such as cynomolgus monkeys, macaques, etc.), lupine, camelid (e.g., from camels, llamas and related species). In another embodiment, the variable region may be condricthoid in origin (e.g., from sharks).

Polypeptides of the invention can be made using techniques that are known in the art. In one embodiment, the polypeptides of the invention are antibody molecules that have been "recombinantly produced," i.e., are produced using recombinant DNA technology. Exemplary techniques for making antibody molecules are discussed in more detail below.

In one embodiment, the polypeptides of the invention are modified antibodies. As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a binding molecule of the invention is a fusion protein comprising at least one heavy chain portion lacking a CH2 domain and comprising a binding domain of a polypeptide comprising the binding portion of one member of a ligand and its receptor.

In one embodiment, the term, "modified antibody" according to the present invention includes immunoglobulins, antibodies, or immunoreactive fragments or recombinants thereof, in which at least a fraction of one or more of the constant region domains has been deleted or otherwise altered so as to provide desired biochemical characteristics such as the ability to non-covalently dimerize, increased ability to localize at the site of a tumor, or reduced serum half-life when compared with a whole, unaltered antibody of approximately the same immunogenicity. In a preferred embodiment, the polypeptides of the present invention are domain deleted antibodies which comprise a polypeptide chain similar to an immunoglobulin heavy chain, but which lack at least a portion of one or more heavy chain domains. More preferably, one entire domain of the constant region of the modified antibody will be deleted and even more preferably all or part of the CH2 domain will be deleted.

In preferred embodiments, a polypeptide of the invention will not elicit a deleterious immune response in a human. Modifications to the constant region compatible with the instant invention comprise additions, deletions or substitutions of one or more amino acids in one or more domains. That is, the polypeptides of the invention disclosed herein may comprise alterations or modifications to one or more of the three heavy chain constant domains (CH1, CH2 or CH3) and/or to the light chain constant region domain (CL).

In one embodiment, the polypeptides of the invention may be modified to reduce their immunogenicity using art-recognized techniques. For example, antibodies or polypeptides of the invention can be humanized, deimmunized, or chimeric antibodies can be made. These types of antibodies are derived from a non-human antibody, typically a murine antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81: 6851-5 (1984); Morrison et al., *Adv. Immunol.* 44: 65-92 (1988); Verhoeyen et al., *Science* 239: 1534-1536 (1988); Padlan, *Molec. Immun.* 28: 489-498 (1991); Padlan, *Molec. Immun.* 31: 169-217 (1994), and U.S. Pat. Nos. 5,585,089, 5,693,761 and 5,693,762 all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of polypeptides of the invention that are tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified. In one embodiment, the binding molecule comprises a chimeric antibody. In the context of the present application the term "chimeric antibodies" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse) and the constant region is human. Preferably, the variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

As used herein the term "properly folded polypeptide" includes polypeptides (e.g., antigen binding molecules such as antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein, the term "neoplasia" includes uncontrolled cell growth, including either benign or malignant tumors. As used herein, the term "malignancy" refers to a non-benign tumor or a cancer.

As used herein, the term "cancer" includes a malignancy characterized by deregulated or uncontrolled cell growth, for instance carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor). A subject having "cancer", for example, may have a tumor or a white blood cell proliferation such as leukemia. In certain embodiments, a subject having cancer is a subject having a tumor, such as a solid tumor. Cancers involving a solid tumor include but are not limited to non small cell lung cancer (NSCLC), testicular cancer, lung cancer, ovarian cancer, uterine cancer, cervical cancer, pancreatic cancer, colorectal cancer (CRC), breast cancer, as well as on prostate, gastric, skin, stomach, esophagus and bladder cancer.

In one embodiment, a binding molecule of the invention binds to a tumor cell. Exemplary antibodies which comprise antigen binding sites that bind to antigens expressed on tumor cells are known in the art and one or more CDRs from such antibodies can be included in a binding molecule of the invention. Exemplary antibodies include: 2B8, Lym 1, Lym 2, LL2, Her2, B1, MB1, BH3, B4, B72.3, 5E8, B3F6 and 5E10. In a preferred embodiment, a polypeptide of the invention is a C2B8 antibody which binds to CD20. In another preferred embodiment, a polypeptide of the invention is a CC49 antibody which recognizes TAG72.

In one embodiment, a binding molecule of the invention binds to a molecule which is useful in treating an autoimmune or inflammatory disease or disorder.

As used herein, the term "autoimmune disease or disorder" refers to disorders or conditions in a subject wherein the immune system attacks the body's own cells, causing tissue destruction. Autoimmune diseases include general autoimmune diseases, i.e., in which the autoimmune reaction takes place simultaneously in a number of tissues, or organ specific autoimmune diseases, i.e., in which the autoimmune reaction targets a single organ. Examples of autoimmune diseases that can be diagnosed, prevented or treated by the methods and compositions of the present invention include, but are not limited to, Crohn's disease; Inflammatory bowel disease (IBD); systemic lupus erythematosus; ulcerative colitis; rheumatoid arthritis; goodpasture's syndrome; Grave's disease; Hashimoto's thyroiditis; pemphigus vulgaris; myasthenia gravis; scleroderma; autoimmune hemolytic anemia; autoimmune thrombocytopenic purpura; polymyositis and dermatomyositis; pernicious anemia; Sjögren's syndrome; ankylosing spondylitis; vasculitis; type I diabetes mellitus; neurological disorders, multiple sclerosis, and secondary diseases caused as a result of autoimmune diseases.

As used herein the term "inflammatory disease or disorder" includes diseases or disorders which are caused, at least in part, or exacerbated by inflammation, e.g., increased blood flow, edema, activation of immune cells (e.g., proliferation, cytokine production, or enhanced phagocytosis). Exemplary disorders include those in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, mitochondria, apoptosis, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories.

Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, osteoarthritis, rheumatoid arthritis, acute and chronic infections (bacterial, viral and fungal); acute and chronic bronchitis, sinusitis, and other respiratory infections, including the common cold; acute and chronic gastroenteritis and colitis; acute and chronic cystitis and urethritis; acute respiratory distress syndrome; cystic fibrosis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; and burns (thermal, chemical, and electrical).

As used herein the term "medium that separates polypeptides based on hydrophobic interaction" includes a medium comprising hydrophobic ligands (e.g., alkyl or aryl groups) covalently attached to a matrix. Such a medium can be used to separate polypeptides based on interaction between a solvent and accessible non-polar groups on the surface of the polypeptides and the hydrophobic ligands of the medium. An exemplary medium is Phenyl 5PW-HR available from Tosoh Bioscience.

As used herein, the term "conductivity" includes electrical conductivity of a solution as measured in microSiemens/cm (formerly micromhos/cm). The greater the ion content of a solution, the greater the conductivity of the solution. Conductivity can be readily measured using techniques that are well known in the art (e.g., by measuring the current passing between two electrodes).

The separation methods of the invention can be used with solutions having a pH ranging from acid to neutral, e.g., from about pH 3.5 to approximately neutral. As used herein, the term "approximately neutral pH" includes pH values of approximately 7. For example, in one embodiment, a separation method of the invention can be performed using a solution (e.g., a buffer) having a pH of about 3, about 4, about 5, about 6, about 7, or about 8. Preferably, the pH of the solution is about 6 or about 7. In one embodiment, the pH of the solution is about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0.

As used herein the term "affinity matrix" includes a matrix, such as agarose, controlled pore glass, or poly (styrenedivinyl) benzene to which an affinity ligand is attached. The affinity ligand binds to the desired polypeptide and the contaminating polypeptides are not bound to the affinity ligand. The desired polypeptide can be eluted from the affinity matrix using known protocols.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the binding molecules of the invention are engineered, e.g., to express a connecting peptide of the invention.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

As used herein, the phrase "subject that would benefit from administration of a binding molecule" includes subjects, such as mammalian subjects, that would benefit from administration of a binding molecule used, e.g., for detection of an antigen recognized by a binding molecule (e.g., for a diagnostic procedure) and/or from treatment with a binding molecule to reduce or eliminate the target recognized by the binding molecule. For example, in one embodiment, the subject may benefit from reduction or elimination of a soluble or particulate molecule from the circulation or serum (e.g., a toxin or pathogen) or from reduction or elimination of a population of cells expressing the target (e.g., tumor cells). As described in more detail herein, the binding molecule can be used in unconjugated form or can be conjugated, e.g., to a drug, prodrug, or an isotope.

The term "apoptosis" or "apoptotic cell death" as used herein includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. As used herein, the term "modulates apoptosis" includes either up regulation or down regulation of apoptosis in a cell.

The term "TNF receptor" or "TNF receptor family member" refers to any receptor belonging to the Tumor Necrosis Factor ("TNF") superfamily of receptors. Members of the TNF Receptor Superfamily ("TNFRSF") are characterized by an extracellular region with two or more cysteine-rich domains (~40 amino acids each) arranged as cysteine knots (see Dempsey et al., *Cytokine Growth Factor Rev.* (2003). 14(3-4): 193-209). Upon binding their cognate TNF ligands, TNF receptors transduce signals by interacting directly or indirectly with cytoplasmic adapter proteins known as TRAFs (TNF receptor associate factors). TRAFs can induce the activation of several kinase cascades that ultimately lead to the activation of signal transduction pathways such as NF-KappaB, JNK, ERK, p38 and PI3K, which in turn regulate cellular processes ranging from immune function and tissue differentiation to apoptosis.

The nucleotide and amino acid sequences of several TNF receptors family members are known in the art and include at least 29 human genes: TNFRSF1A (TNFR1, also known as DR1, CD120a, TNF-R-I p55, TNF-R, TNFRI, TNFAR, TNF-R55, p55TNFR, p55R, or TNFR60, GenBank GI No. 4507575; see also U.S. Pat. No. 5,395,760)), TNFRSF1B (CD120b, also known as p75, TNF-R, TNF-R-I, TNFR80, TNFR2, TNF-R75, TNFBR, or p75TNFR; GenBank GI No. 4507577), TNFRSF3 (Lymphotoxin Beta Receptor (LTβR), also known as TNFR2-RP, CD18, TNFR-RP, TNFCR, or TNF-R-III; GI Nos. 4505038 and 20072212), TNFRSF4 (OX40, also known as ACT35, TXGP1L, or CD134 antigen; GI Nos. 4507579 and 8926702), TNFRSF5 (CD40, also known as p50 or Bp50; GI Nos. 4507581 and 23312371), TNFRSF6 (FAS, also known as FAS-R, DcR-2, DR2, CD95, APO-1, or APT1; GenBank GI Nos. 4507583, 23510421, 23510423, 23510425, 23510427, 23510429, 23510431, and 23510434)), TNFRSF6B (DcR3, DR3; GenBank GI Nos. 4507569, 23200021, 23200023, 23200025, 23200027, 23200029, 23200031, 23200033, 23200035, 23200037, and 23200039), TNFRSF7 (CD27, also known as Tp55 or S152; GenBank GI No. 4507587), TNFRSF8 (CD30, also known as Ki-1, or D1S166E; GenBank GI Nos. 4507589 and 23510437), TNFRSF9 (4-1-BB, also known as CD137 or ILA; GI Nos. 5730095 and 728738), TNFRSF10A (TRAIL-R1, also known as DR4 or Apo2; GenBank GI No. 21361086), TNFRSF10B (TRAIL-R2, also known as DR5, KILLER, TRICK2A, or TRICKB; GenBank GI Nos. 22547116 and 22547119), TNFRSF10C (TRAIL-R3, also known as DcR1, LIT, or TRID; GenBank GI No. 22547121), TNFRSF10D (TRAIL-R4, also known as DcR2 or TRUNDD) TNFRSF11A (RANK; GenBank GI No. 4507565; see U.S. Pat. Nos. 6,562,948; 6,537,763; 6,528,482; 6,479,635; 6,271,349; 6,017,729), TNFRSF11B (Osteoprotegerin (OPG), also known as OCIF or TR1; GI Nos. 38530116, 22547122 and 33878056), TNFRSF12 (Translocating chain-Association Membrane Protein (TRAMP), also known as DR3, WSL-1, LARD, WSL-LR, DDR3, TR3, APO-3, Fn14, or TWEAKR; GenBank GI No. 7706186; US Patent Application Publication No. 2004/0033225A1), TNFRSF12L (DR3L), TNFRSF13B (TACI; GI No. 6912694), TNFRSF13C (BAFFR; GI No. 16445027), TNFRSF14 (Herpes Virus Entry Mediator (HVEM), also known as ATAR, TR2, LIGHTR, or HVEA; GenBank GI Nos. 23200041, 12803895, and 3878821), TNFRSF16 (Low-Affinity Nerve Growth Factor Receptor (LNGFR), also known as Neurotrophin Receptor or p75(NTR); GenBank GI Nos. 128156 and 4505393), TNFRSF17 (BCM, also known as BCMA; GI No. 23238192), TNFRSF18 (AITR, also known as GITR; GenBank GI Nos. 4759246, 23238194 and 23238197), TNFRSF19 (Troy/Trade, also known as TAJ; GenBank GI Nos. 23238202 and 23238204), TNFRSF20 (RELT, also known as FLJ14993; GI Nos. 21361873 and 23238200), TNFRSF21 (DR6), TNFRSF22 (SOBa, also known as Tnfrh2 or 2810028K06Rik), and TNFRSF23 (mSOB, also known as Tnfrh1). Other TNF family members include EDAR1 (Ectodysplasin A Receptor, also known as Downless (DL), ED3, ED5, ED1R, EDA3, EDA1R, EDA-A1R; GenBank GI No. 11641231; U.S. Pat. No. 6,355,782); XEDAR (also known as EDA-A2R; GenBank GI No. 11140823); and CD39 (GI Nos. 2135580 and 765256).

The term "TNF ligand" or "TNF ligand family member" refers to a ligand belonging to the Tumor Necrosis Factor (TNF) superfamily. TNF ligands bind to distinct receptors of the TNF receptor superfamily and exhibit 15-25% amino acid sequence homology with each other (Gaur et al., *Biochem. Pharmacol.* (2003), 66(8):1403-8). The nucleotide and amino acid sequences of several TNF Receptor (Ligand) Superfamily ("TNFSF") members are known in the art and include at least 16 human genes: TNFSF1 (also known as Lymphotoxin-α (LTA), TNFβ or LT, GI No. 34444 and 6806893), TNFSF2 (also known as TNF, TNFα, or DIF; GI No. 25952111), TNFSF3 (also known as Lymphotoxin-β (LTB), TNFC, or p33), TNFSF4 (also known as OX-40L, gp34, CD134L, or tax-transcriptionally activated glycoprotein 1, 34 kD (TXGP1); GI No. 4507603), TNFSF5 (also known as CD40LG, IMD3, HIGM1, CD40L, hCD40L, TRAP, CD154, or gp39; GI No. 4557433), TNFSF6 (also known as FasL or APT1LG1; GenBank GI No. 4557329), TNFSF7 (also known as CD70, CD27L, or CD27LG; GI No. 4507605), TNFSF8 (also known as CD30LG, CD30L, or CD153; GI No. 4507607), TNFSF9 (also known as 4-1BB-L or ILA ligand; GI No. 4507609), TNFSF10 (also known as TRAIL, Apo-2L, or TL2; GI No. 4507593), TNFSF11 (also known as TRANCE, RANKL, OPGL, or ODF; GI Nos. 4507595 and 14790152), TNFSF12 (also known as Fn14L, TWEAK, DR3LG, or APO3L; GI Nos. 4507597 and 23510441), TNFSF13 (also known as APRIL), TNFSF14 (also known as LIGHT, LTg, or HVEM-L; GI Nos. 25952144 and 25952147), TNFSF15 (also known as TL1 or VEGI), or TNFSF16 (also known as AITRL, TL6, hGITRL, or GITRL; GI No. 4827034). Other TNF ligand family members include EDAR1 & XEDAR ligand (ED1; GI No. 4503449; Monreal et al. (1998) *Am J Hum Genet.* 63:380), Troy/Trade ligand, BAFF (also known as TALL1; GI No. 5730097), and NGF ligands (e.g. NGF-β (GI No. 4505391), NGF-2/NTF3; GI No. 4505469), NTF5 (GI No. 5453808)), BDNF (GI Nos. 25306267, 25306235, 25306253, 25306257, 25306261, 25306264; IFRD1 (GI No. 450-4607)).

II. Synthetic Connecting Peptides

At least one polypeptide chain of a dimer of the invention can comprise a synthetic connecting peptide of the invention. In one embodiment, at least two chains of a dimer of the invention comprise a connecting peptide. In a preferred embodiment, two chains of a dimer of the invention comprise a connecting peptide.

In one embodiment, connecting peptides can be used to join two heavy chain portions in frame in a single polypeptide chain. For example, in one embodiment, a connecting peptide of the invention can be used to fuse a CH3 domain (or synthetic CH3 domain) to a hinge region (or synthetic hinge region). In another embodiment, a connecting peptide of the invention can be used to fuse a CH3 domain (or synthetic CH3 domain) to a CH1 domain (or synthetic CH1 domain). In still another embodiment, a connecting peptide can act as a peptide spacer between the hinge region (or synthetic hinge region) and a CH2 domain (or a synthetic CH2 domain).

In another embodiment, a CH3 domain can be fused to an extracellular protein domain (e.g., a VL domain (or synthetic domain), a VH domain (or synthetic domain), a CH1 domain (or synthetic domain), a hinge domain (or synthetic hinge), or to the ligand binding portion of a receptor or the receptor binding portion of a ligand). For example, in one embodiment, a VH or VL domain is fused to a CH3 domain via a connecting peptide (the C-terminus of the connecting peptide is attached to the N-terminus of the CH3 domain and the N-terminus of the connecting peptide is attached to the C-terminus of the VH or VL domain). In another embodiment, a CH1 domain is fused to a CH3 domain via a connecting peptide (the C-terminus of the connecting peptide is attached to the N-terminus of the CH3 domain and the N-terminus of the connecting peptide is attached to the C-terminus of the CH1 domain). In another embodiment, a connecting peptide of the invention can be used to fuse a CH3 domain (or synthetic CH3 domain) to a hinge region (or synthetic hinge region) or portion thereof. In still another embodiment, a connecting peptide can act as a peptide spacer between the hinge region (or synthetic hinge region) and a CH2 domain (or a synthetic CH2 domain).

In one embodiment, a connecting peptide can comprise or consist of a gly/ser spacer. For example, a domain deleted CC49 construct having a short amino acid spacer GGSSGGGSG (SEQ. ID No. 37) substituted for the CH2 domain and the lower hinge region (CC49.ΔCH2 [gly/ser]) can be used. In another embodiment, a connecting peptide comprises the amino acid sequence IGKTISKKAK (SEQ ID NO:16).

In another embodiment, connecting peptide can comprise at least a portion of an immunoglobulin hinge region. For example, chimeric hinge domains can be constructed which combine hinge elements derived from different antibody isotypes. In one embodiment, a connecting peptide comprises at least a portion of an IgG1 hinge region. In another embodiment, a connecting peptide can comprise at least a portion of an IgG3 hinge region. In another embodiment, a connecting peptide can comprise at least a portion of an IgG1 hinge region and at least a portion of an IgG3 hinge region. In one embodiment, a connecting peptide can comprise an IgG1 upper and middle hinge and a single IgG3 middle hinge repeat motif.

Because the numbering of individual amino acids in such connecting peptides comprising an amino acid sequence derived from an immunoglobulin hinge region may vary depending upon the length of the connecting peptide, the numbering of amino acid positions in these molecules is given using Kabat numbering see, e.g., Table 2). Table 1 shows naturally occurring hinge sequence for IgG1, IgG3, and IgG4 molecules. Table 2 shows Kabat numbering for portions of these hinge molecules and also shows Kabat numbering for connecting peptide amino acid residues presented in that table.

In one embodiment, a connecting peptide of the invention comprises a non-naturally occurring immunoglobulin hinge region domain, e.g., a hinge region domain that is not naturally found in the polypeptide comprising the hinge region domain and/or a hinge region domain that has been altered so that it differs in amino acid sequence from a naturally occurring immunoglobulin hinge region domain. In one embodiment, mutations can be made to hinge region domains to make a connecting peptide of the invention. In one embodiment, a connecting peptide of the invention comprises a hinge domain which does not comprise a naturally occurring number of cysteines, i.e., the connecting peptide comprises either fewer cysteines or a greater number of cysteines than a naturally occurring hinge molecule. In a preferred embodiment, incorporation of a connecting peptide (e.g., comprising a non-naturally occurring number of cysteines) into a polypeptide results in a composition in which greater than 50%, 60%, 70%, 80% or 90% of the dimeric molecules present in a form in which the two heavy chain portions are linked via at least one interchain disulfide linkage.

In one embodiment of the invention, a connecting peptide comprises hinge region domain comprising a proline residue at an amino acid position corresponding to amino acid position 243 in the Kabat numbering system (position 230, EU numbering system). In one embodiment, a connecting peptide comprises an alanine residue at an amino acid position corresponding to position 244, Kabat numbering system (position 246, EU numbering system). In another embodiment, a connecting peptide of the invention comprises a proline residue at an amino acid position corresponding to position 245 (Kabat numbering system; position 247, EU numbering system)). In one embodiment, a connecting peptide comprises a cysteine residue at an amino acid position corresponding to position 239, Kabat numbering system (position 226, EU numbering system). In one embodiment, a connecting peptide comprises a serine residue at an amino acid position corresponding to position 239, Kabat numbering system (position 226, EU numbering system). In one embodiment, a connecting peptide comprises a cysteine residue at an amino acid position corresponding to position 242, Kabat numbering system (position 229, EU numbering system). In one embodiment, a connecting peptide comprises a serine residue at an amino acid position corresponding to position 242, Kabat numbering system (position 229, EU numbering system).

In one embodiment, the connecting peptide can be chosen to result in the preferential synthesis of a particular isoform of polypeptide, e.g., in which the two heavy chain portions are linked via disulfide bonds or are not linked via disulfide bonds. For example, as described in the instant examples, the G1/G3/Pro243+[gly/ser] linker (SEQ ID NO: 8), G1/G3/Pro243Ala244Pro245+[gly/ser] linker (SEQ ID NO: 9), Pro243+[gly/ser] linker (SEQ ID NO:15), and Pro243Ala244Pro245+[gly/ser] linker (SEQ ID NO: 14), connecting peptides resulted in the production of only Form A CH2 domain-deleted antibody with no detectable Form B. In contrast, CH2 domain-deleted Cys242Ser:Pro243 (SEQ ID NO: 12), and CH2 domain-deleted Cys242Ser:Pro243Ala244Pro245 (SEQ ID NO: 13), both resulted in a preference for the Form B isoform. These synthetic hinge region connecting peptides would thus be useful for favoring synthesis of Form A or B isoform. This is true for any isotype of antibody, (e.g., IgG1, IgG2, IgG3, or IgG4) based on the high degree of homology among the CH3 domains for all four human isotypes. (Including identical and conserved amino acid residues, IgG1 CH3 domain is 98.13% homologous to IgG2 CH3, 97.20% homologous to IgG3 CH3, and 96.26% homologous to IgG4 CH3). The parentheticals referring to connecting peptides and various binding molecules of the invention represent equivalent terminology unless otherwise indicated.

In one embodiment, a connecting peptide of the invention comprises a hinge region domain followed by a flexible gly/ser linker. Exemplary connecting peptides are shown in Table 2 and in SEQ ID NOs: 7-15, and 23. It will be understood that variant forms of these exemplary connecting peptides can be created by introducing one or more nucleotide substitutions, additions or deletions into the nucleotide sequence encoding a connecting peptide such that one or more amino acid substitutions, additions or deletions are introduced into the connecting peptide. For example, mutations may be introduced by standard techniques, such as site-directed mutagenesis and PCR-mediated mutagenesis. Preferably, conservative amino acid substitutions are made at one or more non-essential amino acid residues such that the ability of the connecting peptide to preferentially enhance synthesis of Form A or Form B is not altered. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Connecting peptides of the invention can be of varying lengths. In one embodiment, a connecting peptide of the invention is from about 15 to about 50 amino acids in length. In another embodiment, a connecting peptide of the invention is from about 20 to about 45 amino acids in length. In another embodiment, a connecting peptide of the invention is from about 25 to about 40 amino acids in length. In another embodiment, a connecting peptide of the invention is from about 30 to about 35 amino acids in length. In another embodiment, a connecting peptide of the invention is from about 24 to about 27 amino acids in length. In another embodiment, a connecting peptide of the invention is from about 40 to about 42 amino acids in length.

Connecting peptides can be introduced into polypeptide sequences using techniques known in the art. For example, in one embodiment, the Splicing by Overlap Extension (SOE) method (Horton, R. M. 1993 Methods in Molecular Biology, Vol 15: PCR Protocols: Current Methods and applications. Ed. B. A. White) can be used. Modifications can be confirmed by DNA sequence analysis. Plasmid DNA can be used to transform host cells for stable production of the polypeptides produced.

In one embodiment, incorporation of one of the subject connecting peptides into a polypeptide yields a composition comprising polypeptide molecules having at least two binding sites and at least two polypeptide chains, wherein at least two of the polypeptide chains comprise a synthetic connecting peptide and wherein greater than 50% of the molecules are present in a form in which the two heavy chain portions are linked via at least one interchain disulfide linkage. In another embodiment, greater than 60% of the molecules are present in a form in which the two heavy chain portions are linked via at least one interchain disulfide linkage. In another embodiment, greater than 70% of the molecules are present in a form in which the two heavy chain portions are linked via at least one interchain disulfide linkage. In another embodiment, greater than 80% of the molecules are present in a form in which the two heavy chain portions are linked via at least one interchain disulfide linkage. In another embodiment, greater than 90% of the molecules are present in a form in which the two heavy chain portions are linked via at least one interchain disulfide linkage.

In one embodiment, incorporation of one of the subject connecting peptides into an IgG4 molecule yields a composition in which greater than 95% of the molecules are present in a form in which the two heavy chain portions are linked via at least one interchain disulfide linkage.

III. Binding Molecules

The polypeptides of the invention comprise at least two binding sites which bind to at least one target molecule of interest. Exemplary binding sites include, e.g., sites which bind to an antigen (antigen binding sites), sites which bind to a receptor (receptor binding sites), or sites which bind to a ligand (ligand binding sites). In one embodiment, the binding molecules comprise at least two binding sites. In one embodiment, the binding molecules comprise two binding sites. In one embodiment, the binding molecules comprise three binding sites. In another embodiment, the binding molecules comprise four binding sites.

In one embodiment, the binding molecules have at least one target binding site specific for a molecule which mediates a biological effect (e.g., which modulates cellular activation (e.g., by binding to a cell surface receptor and resulting in transmission or inhibition of an activating or inhibitory signal), which results in death of the cell (e.g., by complement fixation or exposure to a payload present on the binding molecule), or which modulates a disease or disorder in a subject (e.g., by promoting lysis of a fibrin clot or promoting clot formation, or by modulating the amount of a substance which is bioavailable (e.g., by enhancing or reducing the amount of a ligand such as TNFα in the subject)).

In another embodiment, the binding molecules of the invention have at least one target that transduces a signal to a cell, e.g., by binding to a cell surface receptor, such as a TNF family receptor. By "transduces a signal" it is meant that by binding to the cell, the binding molecule converts the extracellular influence on the cell surface receptor into a cellular response, e.g., by modulating a signal transduction pathway.

In one embodiment, the binding molecules have at least one target binding site specific for a molecule targeted for reduction or elimination, e.g., a cell surface antigen or a soluble antigen. In one embodiment, binding of the binding molecule to the target results in reduction or elimination of the target, e.g., from a tissue or from the circulation. In another embodiment, the binding molecules have at least one binding site specific for a molecule that can be used to detect the presence of a target molecule (e.g., to detect a contaminant or diagnose a condition or disorder). In yet another embodiment, a binding molecule of the invention comprises at least one binding site that targets the binding molecule to a specific site in a subject (e.g., to a tumor cell or blood clot).

Exemplary binding sites that can be included in the binding domain of a binding molecule of the invention include: the receptor binding portion of a ligand, the ligand binding portion of a receptor, the substrate binding portion of an enzyme, the enzyme binding portion of a substrate, or one or more antigen binding portions of an antibody.

In one embodiment, at least one target binding site of a binding molecule (e.g., an antibody molecule, a bispecific antibody, or a modified antibody) is catalytic (Shokat and Schultz. 1990. Annu. Rev. Immunol. 8:335).

In one embodiment, a heavy chain variable portion and a light chain variable portion of a binding molecule are present in the same polypeptide, e.g., as in a single chain antibody or a minibody (see e.g., U.S. Pat. No. 5,837,821 or WO 94/09817A1). In another embodiment, the heavy chain portion and the light chain portion of a polypeptide are present in different polypeptide chains, e.g., as in antibody molecules.

The target binding polypeptides of the invention are multimeric molecules. In one embodiment, the target binding polypeptides are dimers. In one embodiment, the dimers of the invention are homodimers, comprising two identical monomeric subunits. In another embodiment, the dimers of the invention are heterodimers, comprising two non-identical monomeric subunits. The dimers comprise at least two polypeptide chains. In one embodiment, the binding molecules comprise two polypeptide chains. In another embodiment, the binding molecules comprise three polypeptide chains. In another embodiment, the binding molecules comprise four polypeptide chains.

In a preferred embodiment, a binding molecule of the invention comprises at least one CDR of an antibody, e.g., an antibody known in the art to bind to a target of interest. In another embodiment, a binding molecule of the invention comprises at least two CDRs. In another embodiment, a binding molecule of the invention comprises at least three CDRs. In another embodiment, a binding molecule of the invention comprises at least four CDRs. In another embodiment, a binding molecule of the invention comprises at least five CDRs. In another embodiment, a binding molecule of the invention comprises at least six CDRs. In a preferred embodiment, a binding molecule of the invention comprises at least one VH domain of an antibody, e.g., an antibody known in the art to bind to a target of interest. In a preferred embodiment, a binding molecule of the invention comprises at least one VL domain. In another preferred embodiment, a binding molecule of the invention comprises at least one VH domain and one VL domain of an antibody.

In one embodiment, an antigen binding site consists of a VH domain, e.g., derived from camelids, which is stable in the absence of a VL chain (Hamers-Casterman et al. 1993. Nature 363:446; Desmyter et al. 1996. Nat. Struct. Biol. 3:803; Desmyter, A., 1996. Nat. Struct. Biol. 3:803; Decanniere, K., et al. 1999. Structure 7:361; Davies et al. 1996. Protein Eng. 9:531; Kortt et al. 1995. J. Protein Chem. 14:167).

A. Fusion Proteins

The invention also pertains to binding molecules which comprise one or more immunoglobulin domains. The fusion proteins of the invention comprise a binding domain (which comprises at least one binding site) and a dimerization domain (which comprises at least one heavy chain portion). The subject fusion proteins may be bispecific (with one binding site for a first target and a second binding site for a second target) or may be multivalent (with two binding sites for the same target).

Exemplary fusion proteins reported in the literature include fusions of the T cell receptor (Gascoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin (homing receptor) (Watson et al., J. Cell. Biol. 110:2221-2229 (1990); and Watson et al., Nature 349: 164-167 (1991)); CD44 (Aruffo et al., Cell 61:1303-1313 (1990)); CD28 and B7 (Linsley et al., J. Exp. Med. 173:721-730 (1991)); CTLA-4 (Lisley et al., J. Exp. Med. 174:561-569 (1991)); CD22 (Stamenkovic et al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); and IgE receptor a (Ridgway and Gorman, J. Cell. Biol. Vol. 115, Abstract No. 1448 (1991)).

In one embodiment a fusion protein combines the binding domain(s) of the ligand or receptor (e.g. the extracellular domain (ECD) of a receptor) with at least one heavy chain domain and a synthetic connecting peptide. In one embodiment, when preparing the fusion proteins of the present invention, nucleic acid encoding the binding domain of the ligand or receptor will be fused C-terminally to nucleic acid encoding the N-terminus of an immunoglobulin constant domain sequence. N-terminal fusions are also possible. In one embodiment, a fusion protein includes a CH2 and a CH3 domain. Fusions may also be made to the C-terminus of the Fc portion of a constant domain, or immediately N-terminal to the CH1 of the heavy chain or the corresponding region of the light chain.

In one embodiment, the sequence of the ligand or receptor domain is fused to the N-terminus of the Fc domain of an immunoglobulin molecule. It is also possible to fuse the entire heavy chain constant region to the sequence of the ligand or receptor domain. In one embodiment, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. The precise site at which the fusion is made is not critical; particular sites are well known and may be selected in order to optimize the biological activity, secretion, or binding characteristics of the molecule. Methods for making fusion proteins are known in the art.

For bispecific fusion proteins, the fusion proteins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Additional exemplary ligands and their receptors that may be included in the subject binding molecules include the following molecules or molecules which bind to them:

Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, and interferons such as interferon-α, β, or γ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IFNγ (EP0240975), and the TNF family of receptors (e.g., TNFα (e.g. TNFR-1 (EP 417, 563), TNFR-2 (EP 417,014) lymphotoxin beta receptor).

Adhesion Proteins

Adhesion molecules are membrane-bound proteins that allow cells to interact with one another. Various adhesion proteins, including leukocyte homing receptors and cellular adhesion molecules, of receptor binding portions thereof, can be incorporated in a binding molecule of the invention. Leucocyte homing receptors are expressed on leucocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

Chemokines

Chemokines, chemotactic proteins which stimulate the migration of leucocytes towards a site of infection, can also be incorporated into a binding molecule of the invention. Exemplary chemokines include Macrophage inflammatory proteins (MIP-1-α and MIP-1-β), neutrophil chemotactic factor, and RANTES (regulated on activation normally T-cell expressed and secreted).

Growth Factors and Growth Factor Receptors

Growth factors or their receptors (or receptor binding or ligand binding portions thereof) or molecules which bind to them may be incorporated in the binding molecule of the invention. Exemplary growth factors include angiopoietin, Vascular Endothelial Growth Factor (VEGF) and its isoforms (U.S. Pat. No. 5,194,596); Epidermal Growth Factors (EGFs); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); stem-cell factor (SCF), thrombopoietin (c-Mpl ligand), and the Wnt polypeptides (U.S. Pat. No. 6,159,462).

Exemplary growth factor receptors which may be used include EGF receptors (EGFRs); VEGF receptors (e.g. Flt1 or Flk1/KDR), PDGF receptors (WO 90/14425); HGF receptors (U.S. Pat. Nos. 5,648,273, and 5,686,292); IGF receptors (e.g. IGFR1 and IGFR2) and neurotrophic receptors including the low affinity receptor (LNGFR), also termed as $p75^{NTR}$ or p75, which binds NGF, BDNF, and NT-3, and high affinity receptors that are members of the trk family of the receptor tyrosine kinases (e.g. trkA, trkB (EP 455,460), trkC (EP 522,530)). In another embodiment, both IGFR1 and VEGF are targeted. In yet another embodiment, VLA4 and VEGF are targeted.

Other cell surface receptors and/or their ligands can also be targeted (e.g., the TNF family receptors or their ligands (as described in more detail herein).

Hormones

Exemplary growth hormones or molecules which bind to them for use as targeting agents in the binding molecule of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH), calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

Clotting Factors

Exemplary blood coagulation factors for use as targeting agents in the binding molecules of the invention include the clotting factors (e.g., factors V, VII, VIII, X, IX, XI, XII and XIII, von Willebrand factor); tissue factor (U.S. Pat. Nos. 5,346,991, 5,349,991, 5,726,147, and 6,596,84); thrombin and prothrombin; fibrin and fibrinogen; plasmin and plasminogen; plasminogen activators, such as urokinase or human urine or tissue-type plasminogen activator (t-PA).

Another exemplary molecule that may be included in a binding molecule of the invention is immunoglobulin super family member 9 (IGSF9; Genomics. 2002. 79:663-70).

Fusion proteins are taught, e.g., in WO0069913A1 and WO0040615A2. Fusion proteins can be prepared using methods that are well known in the art (see for example U.S. Pat. Nos. 5,116,964 and 5,225,538). Ordinarily, the ligand or receptor domain is fused C-terminally to the N-terminus of the constant region of the heavy chain (or heavy chain portion) and in place of the variable region. Any transmembrane regions or lipid or phospholipids anchor recognition sequences of ligand binding receptor are preferably inactivated or deleted prior to fusion. DNA encoding the ligand or receptor domain is cleaved by a restriction enzyme at or proximal to the 5' and 3' ends of the DNA encoding the desired ORF segment. The resultant DNA fragment is then readily inserted into DNA encoding a heavy chain constant region. The precise site at which the fusion is made may be selected empirically to optimize the secretion or binding characteristics of the soluble fusion protein. DNA encoding the fusion protein is then transfected into a host cell for expression.

B. Antibodies or Portions Thereof

In one embodiment, a binding molecule, e.g., antigen binding molecule, of the invention is an antibody molecule. Using art recognized protocols, for example, antibodies are preferably raised in mammals by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature*, 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, DNA encoding a desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be modified as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. *Immunol. Today* 21:371; Nagy et al. 2002. *Nat. Med.* 8:801; Huie et al. 2001. *Proc. Natl. Acad. Sci. USA* 98:2682; Lui et al. 2002 *J. Mol. Biol.* 315:1063, each of which is incorporated herein by reference. Several publications (e.g., Marks et al. *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. *Nat. Biotechnol.* 18:1287; Wilson et al. 2001. *Proc. Natl. Acad. Sci. USA* 98:3750; or Irving et al. 2001 *J. Immunol. Methods* 248:31. In yet another embodiment, cell surface libraries can be screened for antibodies (Boder et al. 2000. *Proc. Natl. Acad. Sci. USA* 97:10701; Daugherty et al. 2000 *J. Immunol. Methods* 243:211. Such procedures provide alternatives to traditional hybridoma techniques for the isolation and subsequent cloning of monoclonal antibodies.

Yet other embodiments of the present invention comprise the generation of human or substantially human antibodies in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the Vh and Vl genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the polypeptides of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or modified to provide obtain polypeptides of the present invention.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

Variable and constant region domains can be obtained from any source and be incorporated into a modified antibody of the invention. To clone antibodies, mRNA can be isolated from hybridoma, spleen, or lymph cells, reverse transcribed into DNA, and antibody genes amplified by PCR. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250); or based on known variable region framework amino acid sequences from the Kabat (Kabat et al. 1991. Sequences of Proteins of Immunological Interest. Bethesda, Md.: JS Dep. Health Hum. Serv. 5$^{th}$ ed.) or the V-base databases (e.g., Orlandi et al. 1989. Proc. Natl. Acad. Sci. USA 86:3833; Sblattero et al. 1998. Immunotechnology 3:271; or Krebber et al. 1997. J. Immunol. Methods 201:35). Constant region domains can be selected having a particular effector function (or lacking a particular effector function) or with a particular modification to reduce immunogenicity. Variable and constant domains can be cloned, e.g., using the polymerase chain reaction and primers which are selected to amplify the domain of interest. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270).

Alternatively, V domains can be obtained from libraries of V gene sequences from an animal of choice. Libraries expressing random combinations of domains, e.g., VH and VL domains, can be screened with a desired antigen to identify elements which have desired binding characteristics. Methods of such screening are well known in the art. For example, antibody gene repertoires can be cloned into a bacteriophage expression vector (Huse, W D et al. 1989. Science 2476:1275). In addition, cells (Boder and Wittrup. 1997. Nat. Biotechnol. 15:553; Daugtherty, P. et al. 2000. J. Immunol. Methods. 243:211; Francisco et al. 1994. Proc. Natl. Acad. Sci. USA 90:10444; Georgiou et al. 1997. Nature Biotechnology 15:29) or viruses (e.g., Hoogenboom, HR. 1998 Immunotechnology 4:1 Winter et al. 1994. Annu. Rev. Immunol. 12:433; Griffiths, A D. 1998. Curr. Opin. Biotechnol. 9:102) expressing antibodies on their surface can be screened. Ribosomal display can also be used to screen antibody libraries (Hanes J., et al. 1998. Proc. Natl. Acad. Sci. USA 95:14130; Hanes, J. and Pluckthun. 1999. Curr. Top. Microbiol. Immunol. 243:107; He, M. and Taussig. 1997. Nucleic Acids Research 25:5132).

Preferred libraries for screening are human V gene libraries. VL and VH domains from a non-human source may also be used. In one embodiment, such non-human V domains can be altered to reduce their immunogenicity using art recognized techniques.

Libraries can be naïve, from immunized subjects, or semi-synthetic (Hoogenboom, H. R. and Winter. 1992. J. Mol. Biol. 227:381; Griffiths, A D, et al. EMBO J. 13:3245; de Kruif, J. et al. 1995. J. Mol. Biol. 248:97; Barbas, C. F., et al. 1992. Proc. Natl. Acad. Sci. USA 89:4457).

In addition, the sequences of many antibody V and C domains are known and such domains can be synthesized using methods well known in the art.

In one embodiment, mutations can be made to immunoglobulin domains to create a library of nucleic acid molecules having greater heterogeneity (Thompson, J., et al. 1996. J. Mol. Biol. 256:77; Lamminmaki, U. et al. 1999. J. Mol. Biol. 291:589; Caldwell, R. C. and Joyce G F. 1992. PCR Methods Appl. 2:28; Caldwell R C and Joyce G F. 1994. PCR Methods Appl. 3:S136. Standard screening procedures can be used to select high affinity variants. In another embodiment, changes to VH and VL sequences can be made to increase antibody avidity, e.g., using information obtained from crystal structures using techniques known in the art.

Exemplary antibodies or fragments thereof for use in the binding molecules of the invention include antibodies that recognize the targets listed above under subheading A.

C. Modified Antibodies

Exemplary constructs include, e.g., minibodies, diabodies, diabodies fused to CH3 molecules, tetravalent antibodies, intradiabodies (e.g., Jendreyko et al. 2003. J. Biol. Chem. 278:47813), bispecific antibodies, fusion proteins (e.g., antibody cytokine fusion proteins, proteins fused to at least a portion of an Fc receptor), bispecific antibodies. Other immunoglobulins (Ig) and certain variants thereof are described, for example in U.S. Pat. No. 4,745,055; EP 256,654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444, 878; WO 88/03565; and EP 68,763 and references cited therein.

In one embodiment, a polypeptide of the invention comprises an immunoglobulin heavy chain having deletion or substitution of at least one amino acid. For example, the mutation of one or more single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Accordingly, in one embodiment, a binding molecule of the invention lacks all or part of a CH2 domain. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other preferred embodiments may comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

In another embodiment, mutations to naturally occurring hinge regions can be made. Such modifications to the constant region in accordance with the instant invention may easily be made using well known biochemical or molecular engineering techniques well within the skill of the art.

In one embodiment, polypeptides of the invention comprise modified constant regions wherein one or more domains are partially or entirely deleted ("domain deleted antibodies"). In especially preferred embodiments compatible modified antibodies will comprise domain deleted constructs or variants wherein the entire CH2 domain has been removed. A variety of modified antibody constructs are described in more detail below.

i. Minibodies

In one embodiment, the modified antibodies of the invention are minibodies. Minibodies are dimeric molecules made up of two polypeptide chains each comprising an ScFv molecule (a single polypeptide comprising one or more antigen binding sites, e.g., a VL domain linked by a flexible linker to a VH domain fused to a CH3 domain via a connecting peptide.

ScFv molecules can be constructed in a VH-linker-VL orientation or VL-linker-VH orientation.

The flexible hinge that links the VL and VH domains that make up the antigen binding site preferably comprises from about 10 to about 50 amino acid residues. An exemplary connecting peptide for this purpose is (Gly4Ser)3 (SEQ ID NO:17) (Huston et al. 1988. Proc. Natl. Acad. Sci. USA 85:5879). Other connecting peptides are known in the art.

Methods of making single chain antibodies are well known in the art, e.g., Ho et al. 1989. Gene 77:51; Bird et al. 1988 Science 242:423; Pantoliano et al. 1991. Biochemistry 30:10117; Milenic et al. 1991. Cancer Research 51:6363; Takkinen et al. 1991. Protein Engineering 4:837.

Minibodies can be made by constructing an ScFv component and connecting peptide-CH3 component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis.

In one embodiment, a minibody of the invention comprises a connecting peptide. In one embodiment, the connecting peptide comprises a gly/ser linker, e.g., GGGSSGGGSGG (SEQ ID NO: 38).

In another embodiment, a tetravalent minibody can be constructed. Tetravalent minibodies can be constructed in the same manner as minibodies, except that two ScFv molecules are linked using a flexible linker, e.g., having an amino acid sequence $(G4S)_4G3AS$ (SEQ. ID NO: 18).

ii. Domain Deleted Antibodies

In another embodiment, the modified antibodies of the invention are CH2 domain deleted antibodies. Domain deleted constructs can be derived from a vector (e.g., from IDEC Pharmaceuticals, San Diego) encoding an $IgG_1$ human constant domain (see, e.g., WO 02/060955A2 and WO02/096948A2). Essentially, the vector was engineered to delete the CH2 domain and provide a modified vector expressing a domain deleted $IgG_1$ constant region. Genes encoding the murine variable region of the C2B8 antibody, 5E8 antibody, B3F6 antibody, or the variable region of the humanized CC49 antibody were then inserted in the modified vector and cloned. When expressed in transformed cells, these vectors provided C2B8.ΔCH2, 5E8.ΔCH2, B3F6.ΔCH2 or huCC49.ΔCH2 or respectively. These constructs exhibit a number of properties that make them particularly attractive candidates for monomeric subunits.

Besides the deletion of whole constant region domains, it will be appreciated that the antibodies of the present invention can be engineered to partially delete or substitute of a few amino acids or even a single amino acid. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement C1Q binding). Such partial deletions of the constant regions may improve selected characteristics of the antibody (serum half-life) while leaving other desirable functions associated with the subject constant region domain intact. Creation of a $C_H2$ domain deleted version can be accomplished by way of overlapping PCR mutagenesis. The gamma 1 constant domain begins with a plasmid encoded Nhe I site with is in translational reading frame with the immunoglobulin sequence. A 5' PCR primer was constructed encoding the Nhe I site as well as sequence immediately downstream. A 3' PCR primer mate was constructed such that it anneals with the 3' end to the immunoglobulin hinge region and encodes in frame the first several amino acids of the gamma 1 CH3 domain. A second PCR primer pair consisted of the reverse complement of the 3' PCR primer from the first pair (above) as the 5' primer and a 3' primer that anneals at a loci spanning the BsrG I restriction site within the $C_H3$ domain. Following each PCR amplification, the resultant products were utilized as template with the Nhe I and BsrG I 5' and 3', respectively primers. The amplified product was then cloned back into N5KG1 to create the plasmid N5KG1ΔC$_H$2. This construction places the intact CH3 domain immediately downstream and in frame with the intact hinge region. A similar procedure can be used to create a domain deleted construct in which the CH3 domain is immediately downstream of a connecting peptide. For example, a domain deleted version of the C2B8 antibody was created in this manner as described in U.S. Pat. Nos. 5,648,267 and 5,736,137 each of which is incorporated herein by reference.

In one embodiment, tetravalent domain-deleted antibodies can be produced by combining a DNA sequence encoding a domain deleted antibody with a ScFv molecule. For example, in one embodiment, these sequences are combined such that the ScFv molecule is linked at its N-terminus to the CH3 domain of the domain deleted antibody via a flexible linker (e.g., a gly/ser linker such as $(Gly4Ser)_3$ (SEQ ID NO: 17).

In another embodiment a tetravalent antibody can be made by fusing an ScFv molecule to a connecting peptide, which is fused to a CH1 domain to construct an ScFv-Fab tetravalent molecule. (Coloma and Morrison. 1997. Nature Biotechnology. 15:159; WO 95/09917).

iii. Diabodies

Diabodies are similar to scFv molecules, but usually have a short (less than 10 and preferably 1-5) amino acid residue linker connecting both V-domains, such that the VL and VH domains on the same polypeptide chain can not interact. Instead, the VL and VH domain of one polypeptide chain interact with the VH and VL domain (respectively) on a second polypeptide chain (WO 02/02781). In one embodiment, a binding molecule of the invention is a diabody fused to at least one heavy chain portion. In a preferred embodiment, a binding molecule of the invention is a diabody fused to a CH3 domain.

In one embodiment a modified antibody of the invention a binding molecule comprises a tetravalent or bispecific tetravalent CH2 domain-deleted antibody with a scFv appended to the N-terminus of the light chain. In another embodiment of the invention, a binding molecule comprises a tetravalent or bispecific tetravalent CH2 domain-deleted antibody with a scFv appended to the N-terminus of the heavy chain. In one embodiment, the attachment of the scFv to the N-terminus results in reduced aggregation of the molecules as compared to molecules in which the scFv is attached at the carboxy-terminus. In one embodiment, less than about 30% aggregates are present in a composition of binding molecules produced by cells expressing a N-terminal fusion construct. In one embodiment, less than about 20% aggregates are present in a composition of binding molecules produced by cells expressing a N-terminal fusion construct. In one embodiment, less than about 10% aggregates are present in a composition of binding molecules produced by cells expressing a N-terminal fusion construct. In one embodiment, less than about 5% aggregates are present in a composition of binding molecules produced by cells expressing a N-terminal fusion construct.

Other forms of modified antibodies are also within the scope of the instant invention (e.g., WO 02/02781 A1; 5,959,083; 6,476,198 B1; US 2002/0103345 A1; WO 00/06605; Byrn et al. 1990. Nature. 344:667-70; Chamow and Ashkenazi. 1996. Trends Biotechnol. 14:52).

D. Catalytic Antibodies

In one embodiment, at least one binding specificity of a modified antibody molecule of the invention is catalytic. Catalytic binding specificities can be made using art recognized techniques (see, e.g., U.S. Pat. No. 6,590,080, U.S. Pat. No. 5,658,753). Catalytic binding specificities can work by a number of basic mechanisms similar to those identified for enzymes to stabilize the transition state, thereby reducing the free energy of activation. For example, general acid and base residues can be optimally positioned for participation in catalysis within catalytic active sites; covalent enzyme-substrate intermediates can be formed; catalytic antibodies can also be in proper orientation for reaction and increase the effective concentration of reactants by at least seven orders of magnitude (Fersht, A. R., et al., Am. Chem. Soc. 90 (1968): 5833) and thereby greatly reduce the entropy of a chemical reaction. Finally, catalytic antibodies can convert the energy obtained upon substrate binding to distort the reaction towards a structure resembling the transition state.

In one embodiment, acid or base residues can be brought into the binding site by using a complementary charged molecule as an immunogen. This technique proved successful for elicitation of antibodies with a hapten containing a positively-charged ammonium ion (Shokat, et al., Chem. Int. Ed. Engl. 27 (1988):269-271).

In another approach, antibodies can be elicited to stable compounds that resemble the size, shape, and charge of the transition state of a desired reaction (i.e., transition state analogs). See U.S. Pat. No. 4,792,446 and U.S. Pat. No. 4,963,355 which describe the use of transition state analogues to immunize animals and the production of catalytic antibodies. Both of these patents are hereby incorporated by reference. In one embodiment, such molecules can be administered as part of an immunoconjugate, e.g., with an immunogenic carrier molecule, such as KLH.

Exemplary catalytic binding specificities can have, e.g., esterase activity (involving a charged transition state whose electrostatic and shape characteristics can be mimicked by a phosphonate structure; Jacobs, et al., J. Am. Chem. Soc. 109 (1987): 2174-2176; Durfor, et al., J. Am. Chem. Soc. 110 (1988): 8713-8714; Tramontano, et al., J. Am. Chem. Soc. 110 (1988): 2282; Pollack, et al., J. Am. Chem. Soc. 111 (1989): 5961-5962); peptidase or amidase activity (Janda, et al., Science 241 (1988): 1188-1191; Iverson, et al., Science 243 (1989): 1184-1188; Paul, et al., Science 244 (1989): 1158-1162); Claisen rearrangement (Jackson, et al., J. Am. Chem. Soc. 110 (1988): 4841-4842; Hilvert, et al., Proc. Natl. Acad. Sci. USA 85 (1988): 4953-4955; Hilvert, et al., J. Am. Chem. Soc. 110 (1988): 5593-5594); redox reactions (Shokat, et al., Angew. Chem. Int. Ed. Engl. 27 (1989): 269-271); photochemical cleavage of a thymine dimer (Cochran, et al., J. Am. Chem. Soc. 110 (1988): 7888-7890); stereospecific transesterification rearrangements (Napper, et al., Science 237 (1987): 1041-1043); or a bimolecular amide synthesis (Benkovic, et al., Proc. Natl. Acad. Sci. USA 85 (1988): 5355-5358; Janda, et al., Science 241 (1988): 1188-1191).

In another approach, conventional binding specificities can be mutated to render them catalytic.

Methods of screening for catalytic antibody activity are well known in the art (e.g., Reymond, J. L. 2002. Journal of Immunological Methods 269:125; Mouratou et al. 2002. J. of Immunological Methods. 269:147. In yet another embodiment, catalytic B cells can be selected, e.g., as described in U.S. Pat. No. 6,590,080 using a molecule can be constructed which facilitates selection of catalytic B cells.

In another embodiment, catalytic binding specificities can be developed as part of a two step process. Catalytic antibodies can be selected only if displaying the following binding features: binding both the substrate and a reactive group in such a way that the two groups are in a reactive position towards each other. Second, the selected antibodies can be chemically engineered by covalently binding a reactive group into the binding pocket of the antibody. J Immunol Methods. 2002. 269:81-98.

In one embodiment, a catalytic binding specificity is specific for a prodrug. Such a binding specificity can be used to catalyze the conversion of a prodrug into a drug which is effective in vivo. Preferably, the reaction catalyzed is one that cannot be accomplished by natural enzymes in vivo. Examples of prodrug activation by antibodies are known in the art (see, e.g., Miyashita et al. 1993. Proc. Natl. Acad. Sci. USA 90:5337).

In one embodiment, a modified antibody molecule of the invention comprises at least one binding specificity for a target cell and at least one binding specificity for a prodrug. For example, in a preferred embodiment, an modified antibody molecule of the invention comprises at least one binding specificity for a tumor cell and at least one binding specificity for a prodrug which can be converted to cytotoxic drug. In one example, a modified antibody of the invention comprises a binding specificity for a carbamate prodrug 4-[N,N,-bis(2-chloroethyl)]aminophenyl-N-[(1S-(1,3-dicarboxy)propyl] carbamate and generates the corresponding cytotoxic nitrogen mustard (Wentworth et al. 1996. Proc Natl. Acad. Sci. USA. 93:799).

In one embodiment, the modified antibody is administered prior to administration of the prodrug to allow accumulation at the site of the target cell. Exemplary prodrugs are known in the art. Prodrugs can also be synthesized by incorporating a portion designed to be released by catalytic action, e.g., by sequential retro-aldol/retro-Michael reactions catalyzed by an antibody with aldolase activity. (Shabat et al. 2001. Proc. Natl. Acad. Sci. USA 98:7428). Such drug masking portions can be made, e.g., by modification of hydroxyl or thiol groups of drugs.

E. Multispecific Binding Molecules

In one embodiment, a binding molecule of the invention is multispecific, i.e., has at least one binding site that binds to a first target molecule or epitope of the target molecule and at least one second binding site that binds to a second, different target molecule or to a second, different epitope of the first target molecule.

In one embodiment, a binding molecule of the invention is bispecific. Bispecific molecules can bind to two different target sites, e.g., on the same target molecule or on different target molecules. For example, in the case of antibodies, bispecific molecules can bind to two different epitopes, e.g., on the same antigen or on two different antigens. Bispecific molecules can be used, e.g., in diagnostic and therapeutic applications. For example, they can be used to immobilize enzymes for use in immunoassays. They can also be used in diagnosis and treatment of cancer, e.g., by binding both to a tumor associated molecule and a detectable marker (e.g., a chelator which tightly binds a radionuclide. Bispecific molecules can also be used for human therapy, e.g., by directing cytotoxicity to a specific target (for example by binding to a pathogen or tumor cell and to a cytotoxic trigger molecule, such as the T cell receptor or the Fcγ receptor. Bispecific antibodies can also be used, e.g., as fibrinolytic agents or vaccine adjuvants.

In one embodiment, the bispecific binding molecules of the invention include those with at least one arm (i.e. binding site) directed against a cell-surface molecule, and at least one arm directed against a soluble molecule. In another embodiment, a bispecific antibody of the invention has two binding sights that bind to soluble molecules. In another embodiment, a bispecific antibody of the invention has two binding sites that bind to cel surface molecules.

Exemplary cell-surface molecules include receptors or tumor cell antigens that are overexpressed on the surface of a tumor or neoplastic cell. Exemplary soluble molecules include anti-tumor agents (e.g. toxins, chemotherapeutics, and prodrugs thereof) and soluble enzymes (e.g. prodrug converting enzymes).

Bispecific molecules which bind to both tumor cell antigens and anti-tumor agents or soluble enzymes can therefore localize the anti-cancer agent to a tumor cell expressing said tumor cell antigen, thereby maximizing the toxic effects of the anti-cancer agent on a tumor cell and minimizing a toxic effect of the anti-cancer agent on normal cells.

Exemplary bispecific binding molecules with at least one binding site for a tumor antigen and at least one binding site for a toxin include anti-saporin/anti-Id-1, anti-CD22/anti-saporin, anti-CD7/anti-saporin, anti-CD38/anti-saporin, anti-CEA/anti-ricin A chain, anti-interferon-.alpha.(IFN-.alpha.)/anti-hybridoma idiotype, anti-CEA/anti-vinca alkaloid). Exemplary bispecific binding molecules with at least one binding site for a cell-surface molecule and at least one binding site for a prodrug converting enzyme include for example, anti-CD30/anti-alkaline phosphatase (which catalyzes conversion of mitomycin phosphate prodrug to the chemotherapeutic mitomycin alcohol).

In other embodiments, the bispecific binding molecules bind to both tumor cell antigens and diagnostic agents, thereby localizing said diagnostic agent to a tumor cell expressing said tumor cell antigen and facilitating tumor detection in vitro or in vivo. Exemplary bispecific binding molecules include anti-CEA/anti-EOTUBE, anti-CEA/anti-DPTA, anti-CEA/anti-.beta.-galactosidase, and anti-p185HER2/anti-hapten).

In other embodiments, bispecific binding molecules of the invention bind to both soluble molecules (e.g. soluble antigens) and cell surface molecules on non-tumor cells (e.g. immune cells). For example, can be used to target soluble immune complexes to cell surface receptors on immune cells, thereby facilitating their clearance from the body by cell-mediated immune mechanisms. Exemplary bispecific molecules of this type include anti-low density lipoprotein (LDL)/anti-Fc receptor (e.g. Fc.gamma.RI, Fc.gamma.RII or Fc.gamma.RIII)) and bispecific binding molecules for use in therapy of infectious diseases (such as anti-CD3/anti-herpes simplex virus (HSV), anti-T-cell receptor:CD3 complex/anti-influenza, anti-Fc.gamma.R/anti-HIV.

In other embodiments, bispecific binding molecules of the invention are capable of binding to both cell surface receptors and soluble ligands thereof. In one embodiment, the ligand is the cognate ligand of a TNF family receptor.

Exemplary cell surface receptors to which the bispecific binding molecules can bind are tumor cell antigens or immune cell receptors. Exemplary cell surface receptors also include cytokine receptors, adhesion molecules, or growth factor receptors, e.g., as described in section A supra. Exemplary soluble ligands include cytokines, chemokines, hormones, growth factors, or clotting factors, e.g., as described in section A supra.

Exemplary bispecific binding molecules include anti-VLA4/anti-Mac-1, anti-VLA4/anti-VEGF, anti-VLA4/anti-angiopoietin, anti-VLA4/anti-TNFα, anti-IGFR1/anti-VEGF, anti-IGFR1/anti-angiopoietin, anti-IGFR1/anti-EGFR, anti-HGF-SF/anti-VEGF, anti-HGF-SF/anti-angiopoietin, and HGF-SF/any second antigen (See, e.g., Cao et al. Proc. Natl. Acad. Sci. 2001. 98:7443; Lu et al. 2004. J. Biol. Chem. 279:2856).

In other embodiments, the bispecific binding molecules of the invention include those with at least one arm (i.e. binding site) directed against a first soluble molecule (e.g. soluble ligand), and at least one arm directed against a second soluble molecule (e.g. soluble ligand). Such bispecific binding molecules can be employed as diagnostic tools (e.g. anti-rabbit IgG/anti-ferritin, anti-horse radish peroxidase (HRP)/anti-hormone, anti-somatostatin/anti-substance P, anti-HRP/anti-FITC (see Nolan et al., supra)) or fibrinolytic agents (e.g. anti-fibrin/anti-tissue plasminogen activator (tPA), anti-fibrin/anti-urokinase-type plasminogen activator (uPA)).

In a preferred embodiment, the soluble molecule to which a bispecific binding molecule of the invention binds is a soluble ligand of the TNF family. Examples of TNF family ligands include, but are not limited to, LTA (which binds TNFR1/TNFRSF1A), TNF (which binds CD120b/TNFRSF1B), LTB (which binds LTBR/TNFRSF3), OX40L (which binds OX40/TNFRSF4), CD40L (which binds CD40/TNFRSF5), (which binds Fas/TNFRSF6 and DcR3/TNFRSF6B), CD27L (which binds CD27/TNFRSF7), CD30L (which binds CD30/TNFRSF8), 4-1-BB-L (which binds 4-1-BB/TNFRSF9), TRAIL (which binds TRAIL-R1/TNFRSF10A, TRAIL-R2/TNFRSF10B, TRAIL-R3/TNFRSF10C, and TRAIL-R4/TNFRSF10D), RANKL (which binds RANK/TNFRSF11A and Osteoprotegrin/TNFRSF11B), APO-3L (which binds APO-3/TNFRSF12 and DR3L/TNFRSF12L), APRIL (which binds TACI/TNFRSF13B), BAFF (which binds BAFFR/TNFRSF13A), LIGHT (which binds HVEM/TNFRSF14), NGF ligands (which bind LNGFR, e.g. NGF-β, NGF-2/NTF3, NTF5, BDNF, IFRD1), GITRL (which binds GITR/TNFRSF18), EDAR1 & XEDAR ligand, Fn14 ligand, and Troy/Trade ligand.

In other exemplary embodiments, the bispecific binding molecules of the invention have at least one binding site for a first cell-surface molecule and at least one binding site for a second cell-surface molecule. In one embodiment, the first and second cell-surface molecules are located on different cells (e.g. different cell types). For example, bispecific molecules may have at least one arm directed against a tumor cell antigen and at least one arm directed against cell-surface receptor on a non-tumor cell (e.g. an immune cell). Exemplary bispecific binding molecules of this type include those having at least one binding site for a tumor cell antigen and at least one binding site directed against a cytotoxic trigger molecule of an immune effector cell (such as anti-Fc.gamma.RI/anti-CD15, anti-p185.sup.HER2/Fc.gamma.RIII (CD16), anti-p185.sup.HER2/anti-VEGF, anti-CD3/anti-malignant B-cell (1D10), anti-CD3/anti-p185.sup.HER2, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, and anti-pan carcinoma associated antigen (AMOC-31)/anti-CD3)). Bispecific molecules which bind to both tumor cell antigens and cytotoxic trigger molecule are capable of effectively juxtaposing a tumor cell with an immune effector cell, thereby activating the effector cell to destroy the tumor cell by cell-mediated immune mechanisms.

In another embodiment, the first and second cell-surface molecules to which a bispecific binding molecule is capable of binding are located on the same cell or cell type. By crosslinking the first and second receptors on the same cell, the bispecific binding molecules of the invention may inhibit or enhance an activity (e.g. signal transduction activity) associated with one or both of the first and second receptors. In one embodiment the first and second cell surface molecules are of the same type (e.g., are in the same family of molecules). In another embodiment said first and second cell surface molecules are distinct types (e.g., are in different families of molecules). Exemplary cell surface receptors to which the bispecific binding molecules bind include tumor cell antigens or immune cell receptors. Exemplary cell surface receptors include any of the cytokine receptors, adhesion molecules, or growth factor receptors described in section A supra.

In one embodiment, exemplary target molecules to which a binding molecule of the invention binds include one or more epitopes of e.g., heparin sulfate, growth factors or their receptors (e.g., epidermal growth factor receptor, insulin-like growth factor receptor, hepatocyte growth factor (HGF/SF) receptor (See, e.g., Cao et al. Proc. Natl. Acad. Sci. 2001. 98:7443; Lu et al. 2004. J. Biol. Chem. 279:2856).

In an exemplary embodiment, at least one of the molecules to which a bispecific binding molecule of the invention binds is a member of the TNF receptor (TNFR) family. In another exemplary embodiment, the first and second target molecules to which a bispecific binding molecule of the invention binds are both TNFR family members. In another embodiment, a binding molecule of the invention binds to a TNFR family ligand. In yet another embodiment, a binding molecule of the invention binds to one TNFR family member and an antigen expressed on the surface of a tumor cell, e.g., preferentially expressed on a tumor cell. The limiting factor in the treatment of tumors with monospecific TNFR binding molecules is that often only a subset of tumors appears to be sensitive to such therapies. Bispecific TNFR binding molecules can specifically activate TNFRs, and enhance receptor signaling by, for example, bringing the TNFRs into close proximity. The invention provides improved bispecific TNFR binding molecules which can target more than one TNFR or TNFR type and enhance signaling, thus providing an improved method of treating cancer. In one embodiment, the bispecific TNFR binding molecule increases the signal strength by binding to two or more TNFRs of the same type increasing the number of TNFRs being brought together. In another more preferred embodiment, the bispecific TNFR binding molecule is capable of binding to two different receptors of the TNF family.

In one embodiment, at least one of the TNFRs to which a bispecific TNFR binding molecule binds contains a death domain. The term "death domain" refers to a cytoplasmic region of a TNF family receptor which is involved TNF-mediated cell death or apoptotic signaling and cell-cytotoxicity induction mediated by these receptors. This region couples the receptor to caspase activation via adaptor proteins resulting in activation of the extrinsic death pathway.

Examples of TNF receptors which contain death domains include, but are not limited to, TNFR1 (TNFRSF1A), Fas (TNFRSF6), DR-3 (TNFRSF6B), LNGFR (TNFRSF16) TRAIL-R1 (TNFRSF10A), TRAIL-R2 (TNFRSF10B) and DR6 (TNFRSF21). The apoptotic signaling of these receptors is modulated upon binding of a cognate ligand and formation of any of the following receptor-ligand pairs: TNFR1/TNFα, Fas/FasL, DR-3/DR-3LG, TRAIL-R1/TRAIL, or TRAIL-R2/TRAIL.

Bispecific TNFR binding molecules that target TNF family receptors containing death domains are useful for the treatment of cancer since the TNFRs of this type are often overexpressed on tumor cells and stimulating of the receptor can activate tumor cell apoptosis. In preferred embodiments, the death-domain containing TNFR to which the bispecific TNFR binding molecule of the invention binds is TRAIL-R2. TRAIL-R2 is preferred for human tumor therapy since its activation does not trigger hepatocyte apoptosis and hence should have reduced toxicity.

While the activation of some of death domain containing receptors, e.g. TNFR1 or Fas, has been toxic in in vivo applications, it is likely that tethering these receptors to other TNF receptors may diminish toxicity and thus render a toxic antibody less toxic.

In one embodiment, a bispecific TNFR binding molecule of the invention comprises at least one binding site directed to a TNFR containing a death domain and at least one binding site directed to a TNFR lacking a death domain.

In certain exemplary embodiments, TNFRs lacking a death domain include TNFRs involved in tissue differentiation. Examples of TNFR receptors involved in tissue differentiation include LTβR, RANK, EDAR1, XEDAR, Fn14, Troy/Trade, and NGFR. TNFRs involved in tissue differentiation may influence tissue differentiation following binding of a cognate ligand. TNFR binding molecules that target TNFRs involved in tissue differentiation can affect tumors in several ways. First, they have the potential to directly slow tumor growth by altering cell cycle progression. Second, tissue differentiation in the context of tumor cell transformation may lead to cell cycle conflict and default apoptosis. Third, such conflicting input may render a cell more sensitive to chemotherapy.

In certain preferred embodiments, TNFR involved in tissue differentiation is lymphotoxin β receptor (LTβR). LTβR is involved in the control of the maturation status of various specialized stromal cells in the immune system and plays a critical role during the development of the stromal elements of the lymph node anlagen. It has been proposed that activation of a developmental program in epithelial or fibroblastoid cells in the context of a transformed cell is detrimental to their survival and this action may account for some of the anti-tumor activity of LTβR activation. These receptors can also initiate inflammatory programs that involve chemokine release or promote immunological anti-tumor responses. Such release could affect the inflammatory status of the tumor and/or invoke infiltration of lymphoid elements promoting an immunological reaction to the tumor. Thus, bispecific TNFR binding molecules which bind LTβR, alone or in combination with TNF receptors containing death domains (e.g. TRAIL-R2), are encompassed by the invention.

In certain exemplary embodiments, the TNFRs lacking a death domain include TNFRs involved in immune regulation. Such receptors include TNFR2, HVEM, CD27, CD30, CD40, 4-1BB, OX40, GITR, TACI, BAFF-R, BCMA, and RELT. Additional TNF family receptors involved in immune regulation include TRAIL-R3 and TRAIL-R4.

Other target TNF family receptors with a role in tumor formation can be identified using existing RNA databases of receptor expression in various cell types which allow one to define TNF family receptors that are present or ideally overexpressed on various tumors. Moreover, existing RNA databases provide an additional advantage in that the pair of TNF family receptors to which a bispecific TNFR binding molecule of the invention binds could be optimized by identifying those receptor pairs that are more uniquely expressed on a tumor type or subset of tumors but are not abundant on normal tissues, especially liver and vasculature. In such a manner receptor pairs (or more) are identified that could deliver a potent signal to the tumor and spare normal tissues.

The multispecific binding molecules of the invention may be monovalent for each specificity or multivalent for each specificity. In one embodiment, a bispecific binding molecule of the invention may comprise one binding site that reacts with a first target molecule and one binding site that reacts with a second target molecule (e.g. a bispecific antibody molecule, fusion protein, or minibody). In another embodiment, a bispecific binding molecule of the invention may comprise two binding sites that react with a first target molecule and two binding sites that react with a second target molecule (e.g. a bispecific scFv2 tetravalent antibody, tetravalent minibody, or diabody).

In one embodiment, at least one binding site of a multispecific binding molecule of the invention is an antigen binding region of an antibody or an antigen binding fragment thereof.

Figure 2:
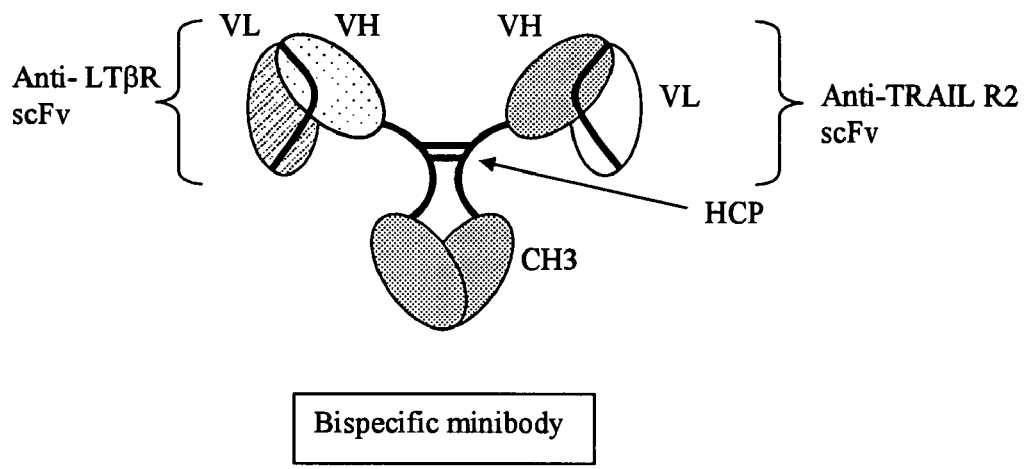
FIG. 2 shows a schematic diagram of an exemplary bispecific two chain dimeric minibody comprising a hinge connecting peptide (HCP). The exemplary minibody contains a first chain portion comprising a scFv with binding specificity for TRAIL R2 antigen and a second chain portion comprising a scFv with binding specificity for the LTβR antigen. The orientation of the VH and VL domains in the scFv may be changed and the respective binding specificities may be altered. $G_4S$ is disclosed as SEQ ID NO: 46 and $(G_4S)_4G_3AS$ is disclosed as SEQ ID NO: 18.

In another embodiment, at least one binding site of multispecific binding molecule is a single chain Fv fragment. In one embodiment, the multispecific binding molecules of the invention are bivalent minibodies with one arm containing a scFv fragment directed to a first target molecule and a second arm containing a scFv directed to a second target molecule. An exemplary bispecific bivalent minibody construct is shown in FIG. 2. In FIG. 2 a CH3 domain is fused at its N-terminus to a connecting peptide which is fused at its N-terminus to a VH domain which is fused via its N-terminus to a flexible linker which is fused at its N-terminus to a VL domain.

Figure 3:
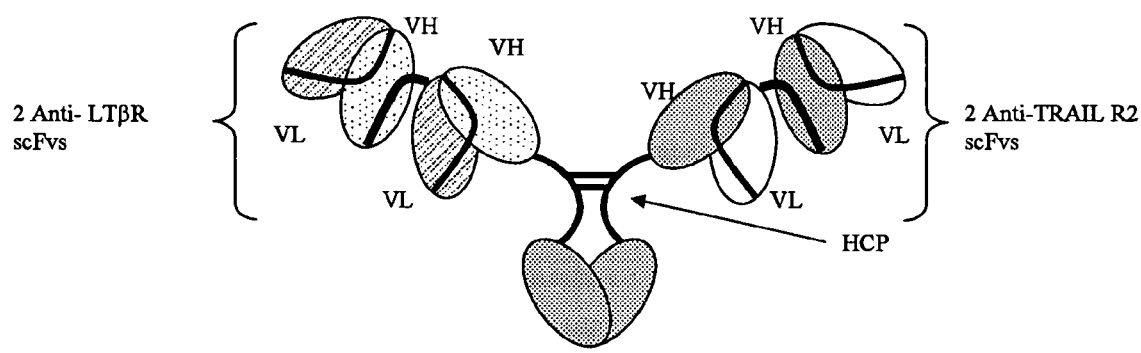
FIG. 3 shows a schematic diagram of an exemplary bispecific two chain dimeric tetravalent minibody (Bispecific N-scFv tetravalent minibody) comprising scFv fragments appended to the amino termini of a bivalent minibody and further comprising a hinge connecting peptide (HCP). The exemplary bivalent tetravalent minibody contains a first chain portion with comprising 2 scFvs with binding specificity for TRAIL R2 antigen and a second chain portion comprising 2 scFvs with binding specificity for the LTβR antigen. Other configurations are also possible, for example, the bispecific tetravalent minibody can also be constructed such that each chain portion contains 2 scFv fragments with different specificities. In another embodiment, the orientation of the VH and VL domains in the scFv may be changed. $G_4S$ is disclosed as SEQ ID NO: 46 and $(G_4S)_4G_3AS$ is disclosed as SEQ ID NO: 18.
Figure 4:
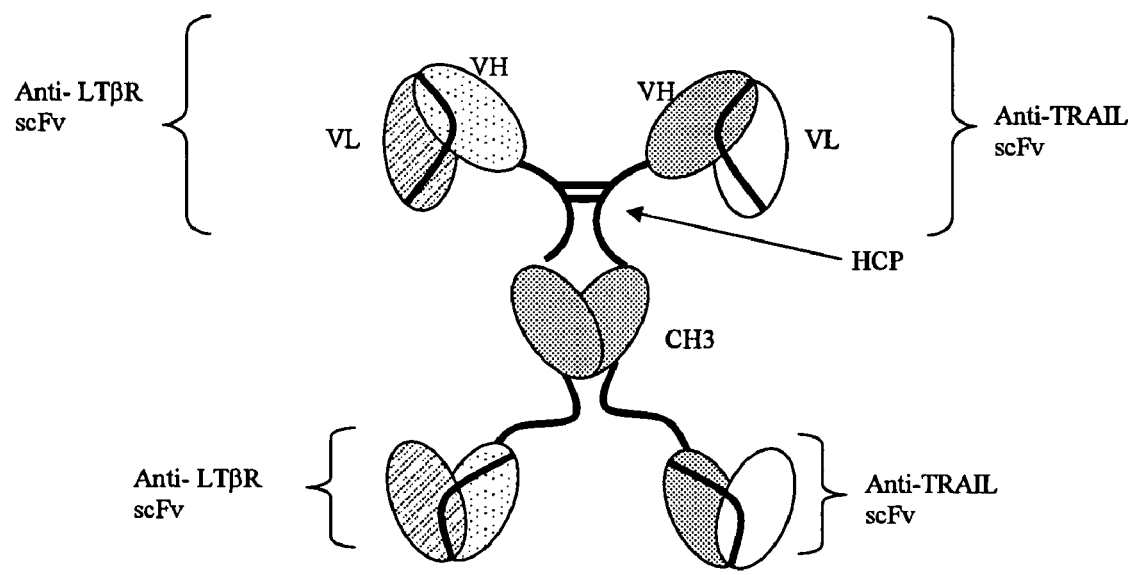
FIG. 4 shows a schematic diagram of an exemplary bispecific two chain dimeric tetravalent minibody (Bispecific C-scFv tetravalent minibody) comprising scFv fragments appended to both carboxyl termini of a bivalent minibody and further comprising a hinge connecting peptide (HCP). The exemplary bivalent tetravalent minibody contains a first chain portion with comprising 2 scFvs with binding specificity for TRAIL R2 antigen and a second chain portion comprising 2 scFvs with binding specificity for the LTβR antigen. Other configurations are also possible, for example, the bispecific two chain dimeric tetravalent minibodies can also be constructed such that each chain contains 2 scFv fragments with different specificities. In another embodiment, the orientation of the VH and VL domains in the scFv may be changed. $G_4S$ is disclosed as SEQ ID NO: 46 and $(G_4S)_4G_3AS$ is disclosed as SEQ ID NO: 18.

In another embodiment, the multispecific binding molecules of the invention are scFv tetravalent minibodies, with each heavy chain portion of the scFv tetravalent minibody containing first and second scFv fragments. Said second scFv fragment may be linked to the N-terminus of the first scFv fragment (e.g. bispecific $N_H$ scFv tetravalent minibodies or bispecific $N_L$ scFv tetravalent minibodies). An example of a bispecific N-scFv tetravalent minibody is shown in FIG. 3. Alternatively, the second scFv fragment may be linked to the C-terminus of said heavy chain portion containing said first scFv fragment (e.g. bispecific C-scFv tetravalent minibodies). An example of a bispecific C-scFv tetravalent minibody is shown in FIG. 4. In one embodiment, the first and second scFv fragments of may bind the same or different target molecule. Where the first and second scFv fragments of a first heavy chain portion of a bispecific tetravalent minibody bind the same target molecule, at least one of the first and second scFv fragments of the second heavy chain portion of the bispecific tetravalent minibody binds a different target molecule.

Figure 5:
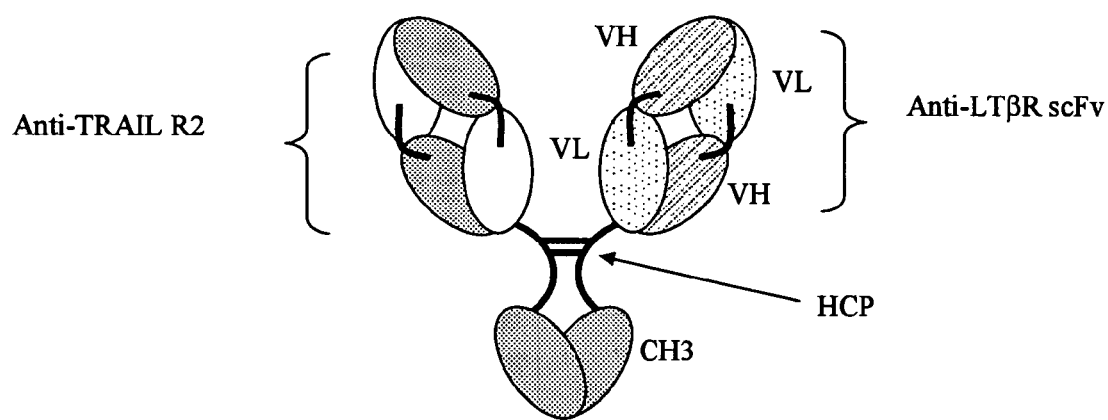
FIG. 5 shows a schematic diagram of a bispecific four chain dimeric diabody comprising a hinge connecting peptide (HCP). Other configurations are also possible, for example, the bispecific two chain dimeric tetravalent minibody comprising a connecting peptide (HCP) can also be constructed such that each arm contains scFv fragments with different specificities. The orientation of the VH and VL domains may be changed.
Figure 5:

In another embodiment, the multispecific binding molecules of the invention are bispecific diabodies, with each arm of the diabody comprising tandem scFv fragments. In one embodiment, a bispecific diabody may comprise a first arm with a first binding specificity and a second arm with a second binding specificity (see, for example, FIG. 5). In another embodiment, each arm of the diabody may comprise a first scFv fragment with a first binding specificity and a second scFv fragment with a second binding specificity.

Figure 6:
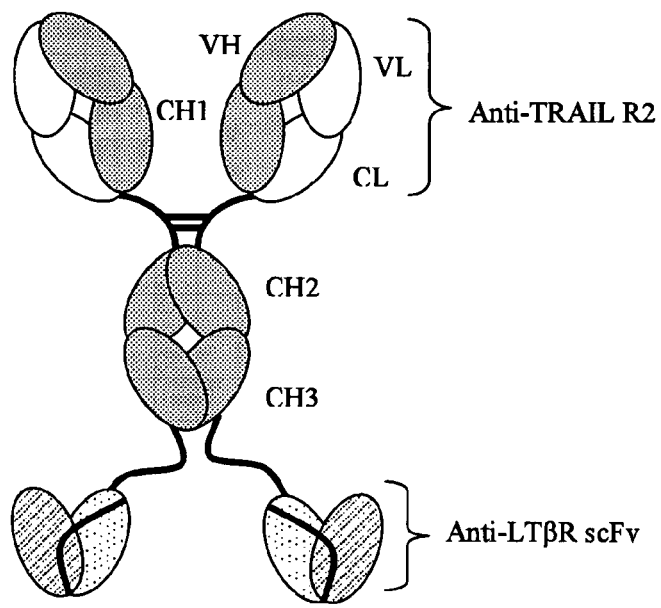
FIG. 6 shows a schematic diagram of a bispecific four chain dimeric tetravalent scFv antibody (C-scFv tetravalent antibody) comprising a scFv appended to the carboxyl terminus of CH3 and a hinge connecting peptide. The orientation of the VH and VL domains in the scFv may be changed. Alternatively, the scFv fragments can be appended to the amino termini of either the heavy or light chain portions to form $N_H$-scFv tetravalent antibodies or $N_L$-scFv tetravalent antibodies, respectively. $G_4S$ is disclosed as SEQ ID NO: 46

In another embodiment, the multispecific binding molecules of the invention are scFv2 tetravalent antibodies with each heavy chain portion of the scFv2 tetravalent antibody containing a scFv fragment. The scFv fragments may be linked to the N-termini of a variable region of the heavy chain portions (e.g. bispecific $N_H$ scFv2 tetravalent antibodies or bispecific $N_L$ scFv2 tetravalent antibodies). Alternatively, the scFv fragments may be linked to the C-termini of the heavy chain portions of the scFv2 tetravalent antibody (e.g. bispecific C-scFv2 tetravalent antibodies, see for example FIG. 6). Each heavy chain portion of the scFv2 tetravalent antibody may have variable regions and scFv fragments that bind the same or different target molecules. Where the scFv fragment and variable region of a first heavy chain portion of a bispecific scFc2 tetravalent antibody bind the same target molecule, at least one of the first and second scFv fragments of the second heavy chain portion of the bispecific tetravalent minibody binds a different target molecule.

In another embodiment, the multispecific binding molecules of the invention are scFv2 tetravalent domain-deleted antibodies with each heavy chain portion of the scFv2 tetravalent antibody containing a scFv fragment. The scFv fragments may be linked to the N-termini of a variable region of the heavy chain portions (e.g. bispecific $N_H$ scFv2 tetravalent domain-deleted antibodies (see FIG. 8) or bispecific $N_L$ scFv2 tetravalent antibodies (see FIG. 9)). Alternatively, the scFv fragments may be linked to the C-termini of the heavy chain portions of the scFv2 tetravalent antibody (e.g. bispecific C-scFv2 tetravalent antibodies, see for example FIG. 7).

Methods of producing bispecific molecules are well known in the art. For example, recombinant technology can be used to produce bispecific molecules, e.g., diabodies, single-chain diabodies, tandem scFvs, etc. Exemplary techniques for producing bispecific molecules are known in the art (e.g., Kontermann et al. Methods in Molecular Biology Vol. 248: Antibody Engineering: Methods and Protocols. Pp 227-242 US 2003/0207346 A1 and the references cited therein). In one embodiment, a multimeric bispecific molecules are prepared using methods such as those described e.g., in US 2003/0207346A1 or U.S. Pat. No. 5,821,333, or US2004/0058400.

In another embodiment, a multispecific binding molecule of the invention is a multispecific fusion protein. As used herein the phrase "multispecific fusion protein" designates fusion proteins (as hereinabove defined) having at least two binding specificities (i.e. combining two or more binding domains of a ligand or receptor). Multispecific fusion proteins can be assembled as heterodimers, heterotrimers or heterotetramers, essentially as disclosed in WO 89/02922 (published Apr. 6, 1989), in EP 314, 317 (published May 3, 1989), and in U.S. Pat. No. 5,116,964 issued May 2, 1992. Preferred multispecific fusion proteins are bispecific. Examples of bispecific fusion proteins include CD4-IgG/TNF receptor-IgG and CD4-IgG/L-selectin-IgG. The last mentioned molecule combines the lymph node binding function of the lymphocyte homing receptor (LHR, L-selectin), and the HIV binding function of CD4, and finds potential application in the prevention or treatment of HIV infection, related conditions, or as a diagnostic.

In another embodiment, the invention pertains to bispecific binding molecules, e.g., antibodies, which incorporate at least one binding site that binds to a known target and at least one binding site which recognizes an unknown target (for example, in one embodiment, the bispecific molecule incorporates binding sites selected from a semi-synthetic antibody phage display library).

In one embodiment of the invention, one of ordinary skill in the art could start with a single chain antibody of known specificity and build a Fab library using techniques known in the art or, alternatively, the skilled artisan could start with an Fab fragment of known specificity and build a single chain library using techniques known in the art. It is known in the art that libraries from nonimmunized sources and prepared by synthetic recombination of V-gene sequences (preferably recombination of VH with, DH and JH, and VL with JL sequences) can be used to isolate antibodies to any antigen. For example, patent application WO92/01047 teaches that antibody fragments can be displayed on the surface of bacteriophage and that they will bind antigen. Antibody fragments (e.g., Fab, Fv, ScFv and VH) can be directly selected using this characteristic. Other methods known in the art include those taught, e.g., in U.S. Pat. Nos. 5,698,426; 6,291,159; 5,658,727; 5,667,988; and 5,969,108.

In another embodiment, scFv which recognize a known target can be dimerized with scFv isolated from a semi-synthetic human phage antibody display library. (see, e.g., Kruif and Logtenberg 1996. J. Biol. Chem. 271:7630).

In one embodiment, the subject bispecific molecule is expressed in any expression system used to express antibody molecules, for example mammalian cells, yeast such as Picchia, E. coli, Bacculovirus, etc. In one embodiment, the subject bispecific molecule is expressed in the NEOSPLA vector system (see, e.g., U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence.

In one embodiment, the subject bispecific molecules comprise a synthetic connecting peptide.

These bispecific molecules have one or more binding sites for a known target and express a library at one or more binding sites. Such bispecific molecules can be used, e.g., to identify molecules in close proximity to or associated with the known target. For example, the skilled artisan could use the subject bispecific molecules in an assay to select for those that induce a particular response, e.g., apoptosis or cellular activation, using screening methods well known in the art. The bispecific molecule identified as producing the response screened for can then be identified and its specificity determined. Using such methods it is possible to identify molecules in close association with particular targets of interest, e.g., T cell markers or other signaling molecules (such as CRIPTO-I, death domain molecules, or molecules involved in apoptosis). The proximity of the known target and the molecule newly identified as a "nearest neighbor" can be confirmed using immunoprecipitation or other techniques known to those of skill in the art. Using these methods it is possible to identify molecules as targets for modulating a particular cellular response.

Binding specificities comprising antigen recognition sites or entire variable regions of multispecific binding molecule, in particular multispecific antibodies or antibody variants of the invention may be derived from one or more parental antibodies. The parental antibodies can include naturally occurring antibodies or antibody fragments, antibodies or antibody fragments adapted from naturally occurring antibodies, antibodies constructed de novo using sequences of antibodies or antibody fragments known to be specific a target molecule. Sequences that may be derived from parental antibodies include heavy and/or light chain variable regions and/or CDRs, framework regions or other portions thereof.

In one exemplary embodiment of the invention, the parental antibodies used to construct a bispecific TNFR binding molecule are an anti-TRAIL-R2 antibody, for example 14A2, and an anti-LTβR antibody, for example CBE11. Multivalent, multispecific antibodies may contain a heavy chain comprising two or more variable regions and/or a light chain comprising one or more variable regions wherein at least two of the variable regions recognize different epitopes of LTβR.

Bispecific TNFR binding molecules may be constructed in a variety different ways using a variety of different sequences derived from parental anti-LTβR antibodies, including murine or humanized BHA10 (Browning et al., J. Immunol. 154:33 (1995); Browning et al. J. Exp. Med. 183:867 (1996)), murine or humanized CBE11 (U.S. Pat. No. 6,312,691 and WO 02/30986, respectively), and/or parental anti-TRAIL-R2 murine or chimeric 14A2. Examples of anti-LTβR antibodies which can be used for the bispecific TNFR binding molecules of the invention include consisting: BKA11, CDH10, BCG6, AGH1, BDA8, CBE11 and BHA10. The following hybridoma cell lines producing monoclonal anti-LT-β-R antibodies may be used to produce anti-LTβR antibodies from which to derive antibody construct sequences, which have been previously deposited with the American Type Culture Collection (ATCC) according to the provisions of the Budapest Treaty and have been assigned the indicated ATCC accession numbers:

| Cell Line | mAb Name | Accession No. |
| --- | --- | --- |
| a) AG.H1.5.1 | AGH1 | HB 11796 |
| b) BD.A8.AB9 | BDA8 | HB 11798 |
| c) BC.G6.AF5 | BCG6 | B 11794 |
| d) BH.A10 | BHA10 | B 11795 |
| e) BK.A11.AC10 | BKA11 | B 11799 |
| f) CB.E11.1 | CBE11 | B 11793 |
| g) CD.H10.1 | CDH10 | B 11797 |

Other examples of anti-TNF receptor antibodies which can be used in the bispecific TNFR binding molecules of the invention include antibodies directed to TNF receptors containing a death domain. A number of antibodies have been generated to death domain containing TNF receptors and are well known in the art. Such antibodies include anti-TNF-R1 monoclonal antibodies (R&D systems anti-TNF-R1; Tularik mAb #985, U.S. Pat. Nos. 6,110,690; 6,437,113), anti-Fas receptor mAb CH-11 (U.S. Pat. No. 6,312,691; WO 95/10540), anti-DR3 antibodies (U.S. Pat. No. 5,985,547; Johnson, et al. (1984) ImmunoBiology of HLA, ed. Dupont, B. O., Springer, New York; U.S. Pat. Nos. 6,462,176; 6,469, 166), and anti-TRAIL-R antibodies (U.S. Pat. Nos. 5,763, 223; 6,072,047; 6,284,236; 6,521,228; 6,569,642; 6,642,358; and U.S. Pat. No. 6,417,328).

A number of antibodies have been also raised to TNF receptors involved in tissue differentiation and are known in the art. Examples of anti-TNF receptor antibodies specific to TNF receptors involved in tissue differentiation include: anti-RANK monoclonal antibodies (Immunex—U.S. Pat. Nos. 6,562,948; 6,537,763; 6,528,482; 6,479,635; 6,271,349; 6,017,729; Komed—WO 03/080671), anti-EDAR polyclonal (anti-human) and monoclonal (anti-mouse) antibodies (R&D Systems—MAB745, BAF157; Elomaa et al. (2001) Human Molecular Genetics. 10:953), anti-XEDAR monoclonal and polyclonal antibodies (R&D Systems—MAB1093 and AF1093), anti-Fn14 monoclonal antibodies (Nakayama et al. (2003) J. Immunology 170:341; ITEM-1, ITEM-2, and ITEM-4 clones available from eBioscience), anti-TROY antibody (T3323 from Sigma-Aldrich), and anti-NGFR (anti-rodent) antibodies (Chemicon USA).

A number of antibodies have been also raised to TNF receptors involved in immune regulation and are known in the art. Examples of anti-TNF receptor antibodies specific to TNF receptors involved in immune regulation include: anti- HVEM antibodies (HGSI—WO 03/086301), anti-CD40 antibodies (Biogen—WO 97/20063; Chiron—U.S. Pat. Nos. 5,677,165; 5,874,082; 6,004,552; 6,056,959; 6,315,998; US Application Publication No. 2002/0106371; US Application Publication Nos. 2003/0059427; US20030118588A1; 2003/021110A1; US2002020142358A1; U.S. Pat. No. 6,312,693; U.S. Pat. No. 6,051,228; Fanslow et al.—U.S. Pat. No. 5,801,227), anti-4-1BB (PCT Publication No. WO 03/084999; EP 0948353; U.S. Pat. No. 6,210,669; Genecraft—WO 03/083069), and anti-BAFF-R antibodies (rabbit polyclonal—ProSci catalog #3097), among many other antibodies raised to immune regulation receptors.

A variety of other multivalent antibody constructs may be developed by one of skill in the art using routine recombinant DNA techniques, for example as described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; Beidler et al. (1988) *J. Immunol.* 141:4053-4060; and Winter and Milstein, Nature, 349, pp. 293-99 (1991)). Preferably non-human antibodies are "humanized" by linking the non-human antigen binding domain with a human constant domain (e.g. Cabilly et al., U.S. Pat. No. 4,816,567; Morrison et al., Proc. Natl. Acad. Sci. U.S.A., 81, pp. 6851-55 (1984)).

Other methods which may be used to prepare multivalent anti-TNF receptor antibody constructs are described in the following publications: Ghetie, Maria-Ana et al. (2001) *Blood* 97:1392-1398; Wolff, Edith A. et al. (1993) *Cancer Research* 53:2560-2565; Ghetie, Maria-Ana et al. (1997) *Proc. Natl. Acad. Sci.* 94:7509-7514; Kim, J. C. et al. (2002) *Int. J. Cancer* 97(4):542-547; Todorovska, Aneta et al. (2001) *Journal of Immunological Methods* 248:47-66; Coloma M. J. et al. (1997) *Nature Biotechnology* 15:159-163; Zuo, Zhuang et al. (2000) *Protein Engineering* (Suppl.) 13(5):361-367; Santos A. D., et al. (1999) *Clinical Cancer Research* 5:3118s-3123s; Presta, Leonard G. (2002) *Current Pharmaceutical Biotechnology* 3:237-256; van Spriel, Annemiek et al., (2000) *Review Immunology Today* 21(8) 391-397.

B. Expression of Polypeptides

Following manipulation of the isolated genetic material to provide polypeptides of the invention as set forth above, the genes are typically inserted in an expression vector for introduction into host cells that may be used to produce the desired quantity of modified antibody that, in turn, provides the claimed polypeptides.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Exemplary vectors include those taught in U.S. Pat. No. 6,159,730 or 6,413,777 or US 2003 0157641 A1). Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

In one embodiment, an inducible expression system can be employed.

Additional elements may also be needed for optimal synthesis of mRNA. These elements may include signal sequences, splice signals, as well as transcriptional promoters, enhancers, and termination signals.

In one embodiment, a secretion signal, e.g., any one of several well characterized bacterial leader peptides (e.g., pelB, phoA, or ompA), can be fused in-frame to the N terminus of a polypeptide of the invention to obtain optimal secretion of the polypeptide. (Lei et al. 1988 Nature 331:543; Better et al. Science 1988. 240:1041; Mullinax et al., 1990. Proc. Natl. Acad. Sci. USA 87:8095).

In one embodiment, a vector can be used which comprises a nucleic acid sequence encoding a peptide linker. In another embodiment, it might be desirable to first assemble the desired coding sequences (e.g., secretion signal, VL, linker peptide, VH, etc.) into a single sequence, for example, by PCR amplification using overlapping primers, followed by ligation into a plasmid or other vector.

In particularly preferred embodiments the cloned variable region genes are inserted into an expression vector along with the heavy and light chain constant region genes (preferably human) modified as discussed above. Preferably, this is effected using a proprietary expression vector of IDEC, Inc., referred to as NEOSPLA see U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. As seen in the examples below, this vector has been found to result in very high level expression of antibodies upon incorporation of variable and constant region genes, transfection in CHO cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the polypeptides of the invention of the instant invention may be expressed using polycistronic constructs such as those disclosed in U.S. provisional application No. 60/331,481 filed Nov. 16, 2001 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a monomeric subunit of the polypeptide (e.g. a modified antibody) has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to any introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

In another embodiment, a host cell is a prokaryotic cell, e.g., a strain which allows the formation of disulfide bonds (Derman, A I, et al. 1993. Science. 262:1744; Bessette, P H. Et al. 1999. Proc. Natl. Acad. Sci. USA 96:13703).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a modified hinge region polypeptide or prior to or subsequent to the HIC chromatography step described herein.

Genes encoding the polypeptide of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules. Where tetravalent forms of antibodies are desired, the subunits will then self-assemble into tetravalent antibodies (WO02/096948A2).

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

IV. Separation of Polypeptides Comprising at Least One Interchain Disulfide Linkage From Those Lacking Interchain Disulfide Linkages In one aspect, the invention pertains to separation of molecules having two heavy chain portions from a mixture, where a fraction of the molecules are present in a form in which the two heavy chain portions are linked via at least one interchain disulfide linkage and a fraction of the molecules comprise heavy chain portions that are not linked via at least one disulfide linkage by hydrophobic interaction chromatography.

Hydrophobic interaction chromatography was first developed following the observation that proteins could be retained on affinity gels which comprised hydrocarbon spacer arms but lacked the affinity ligand. Elution from HIC supports can be effected by alterations in solvent, pH, ionic strength, or by the addition of chaotropic agents or organic modifiers, such as ethylene or propylene glycol. A description of the general principles of hydrophobic interaction chromatography can be found e.g., in U.S. Pat. No. 3,917,527 and in U.S. Pat. No. 4,000,098. HIC in the context of high performance liquid chromatography (HPLC) has been used to separate antibody fragments lacking heavy chain portions (e.g., F(ab')$_2$) from intact antibody molecules in a single step protocol. (Morimoto, K. et al., L Biochem. Biophys. Meth. 24: 107 (1992)).

The separation method of the invention can be performed on an unpurified population of polypeptides (e.g., culture supernatants or preparations or preparations of polypeptides isolated from prokaryotic inclusion bodies). Alternatively, the instant separation methods can be used on polypeptide mixtures obtained after one or more initial purification steps, e.g., after a preparation comprising forms A and B has been eluted from an affinity matrix.

In one embodiment, the binding molecules subjected to HIC chromatography comprise a connecting peptide of the invention.

In a preferred embodiment, HIC can be applied to mixtures that have been partially purified by other protein purification procedures. The term "partially purified" as used herein includes a protein preparation in which the protein of interest is present in at least 5% by weight, more preferably at least 10% and most preferably at least 45%. Initial or subsequent purification steps can be used to remove, e.g., immunoglobulin aggregates, misfolded species, host cell protein, residue material from preceding chromatographic steps (such as Protein A when employed). In one embodiment, HIC can be performed on polypeptides comprising a connecting peptide of the invention. Accordingly, the application of HIC can also be appreciated in the context of an overall purification protocol. Exemplary purification steps that can be used prior to or subsequent to HIC include: affinity chromatography (for example, PROSEP-A® (BioProcessing Ltd., U.K.) which consists of Protein A covalently coupled to controlled pore glass or Protein A SEPHAROSE® Fast Flow (Pharmacia) or TOYOPEARL 650M Protein A (TosoHaas)). Protein A is preferred for human γ1, γ2, or γ4 heavy chains and protein G for mouse isotypes. Bakerbond ABXtm resin can be used if the molecule comprises a CH3 domain. In addition or alternatively, ion exchange chromatography may be employed. In this regard various anionic or cationic substituents may be attached to matrices in order to form anionic or cationic supports for chromatography. Anionic exchange substituents include diethylaminoethyl(DEAE), quaternary aminoethyl (QAE) and quaternary amine(Q) groups. Cationic exchange substituents include carboxymethyl (CM), sulfoethyl(SE), sulfopropyl(SP), phosphate(P) and sulfonate(S). Cellulose ion exchange resins such as DE23, DE32, DE52, CM-23, CM-32 and CM-52 are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow are all available from Pharmacia AB. Further, both DEAE and CM derivitized ethylene glycol-methacrylate copolymer such as TOYOPEARL DEAE-650S or M and TOYOPEARL CM-650S or M are available from Toso Haas Co., Philadelphia, Pa. Because elution from ion exchange supports usually involves addition of salt and because HIC is enhanced under increased salt concentrations, the introduction of a HIC step following an ionic exchange chromatographic step or other salt mediated purification step is preferred. Additional purification protocols may be added including but not necessarily limited to: further ionic exchange chromatography, size exclusion chromatography, viral inactivation, concentration and freeze drying, hydroxylapatite chromatography, gel electrophoresis, dialysis, ethanol precipitation, reverse phase HPLC, chromatography on silica, chromatography on heparin SEQHAROSE™, chromatofocusing, or ammonium sulfate precipitation.

Prior to purification using the subject methods, the composition comprising the mixture of polypeptides to be separated will preferably be placed in a buffer of acidic or approximately neutral pH. This can be done, for example, by adding concentrated buffer, resuspending the sample in the buffer, exchanging the buffer (e.g., using dialysis or ultrafiltration). Alternatively, the pH of the sample buffer can simply be adjusted to be within the desired range.

Hydrophobic interactions are strongest at high ionic strength, therefore, this form of separation is conveniently performed following salt precipitations or ion exchange procedures. Adsorption of the proteins to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++}<; Ca^{++}<; Mg^{++}<; Li^+<; Cs^+<; Na^+<; K^+<; Rb^+<; NH_4^+$, while anions may be ranked in terms of increasing chaotropic effect as $PO^{---}<; SO_4^{--}<; CH_3COOO^-<; Cl^-<; Br^-<; NO_3^-<; ClO_4^-<; I^-<; SCN^-$ In general, Na, K or $NH_4$ sulfates effectively promote ligand-protein interaction in HIC. Salts may be formulated that influence the strength of the interaction as given by the following relationship: $(NH_4)_2SO_4>; Na_2SO_4>; NaCl>; NH_4Cl>; NaBr>; NaSCN$. In general, salt concentrations of between about 0.75 and about 2M ammonium sulfate or between about 1 and 4M NaCl are useful.

A number of chromatographic supports may be employed in the preparation of HIC columns, the most extensively used are agarose, silica and organic polymer or co-polymer resins. The hydrophobic interaction material is generally a base matrix (e.g., a hydrophilic carbohydrate (such as cross-linked agarose) or synthetic copolymer material) to which hydrophobic ligands (e.g., alkyl or aryl groups) are coupled. The preferred HIC material comprises an agarose resin substituted with phenyl groups. Exemplary HIC material includes: phenyl SEPHAROSE™, FAST FLOW with low or high substitution (Pharmacia LKB Biotechnology, AB, Sweden); phenyl SEPHAROSE™ High Performance column; phenyl or butyl-SEPHAROSE® CL-4B, butyl-SEPHAROSE® FF, octyl-SEPHAROSE® FF and phenyl-SEPHAROSE® FF (Pharmacia LKB Biotecheology AB, Sweden); Fractogel™ EMD Propyl or FRACTOGEL™ EMC Phenyl columns (E. Merck, Germany); MACROPREP™ Methyl or MACROPREP™ t-Butyl Supports (Bio-Rad, California); WP HI-Propyl (C3)™ column (J. T. Baker, New Jersey). Exemplary HIC materials are also available from Tosoh Corporation, Tokyo, Japan under the product names TOYOPEARL ether 650, phenyl 650, butyl 650 (Fractogel), ether-5PW-HR, or phenyl-5PW-HR; Miles-Yeda, Rehovot, Israel under the product name alkyl-agarose, wherein the alkyl group contains from 2-10 carbon atoms, and J. T. Baker, Phillipsburg, N.J. under the product name Bakerbond WP-HI-propyl. It is also possible to prepare the desired HIC column using conventional chemistry. (Sa: for example, Er-el. Z. gl all, Biochem. Biophys. Res. Comm. 49:383 (1972) or Ulbrich, V. rd gL Coll. Czech. Chem. Commum. 9:1466 (1964)).

The choice of a particular gel can be determined by the skilled artisan. In general the strength of the interaction of the protein and the HIC ligand increases with the chain length of the alkyl ligands but ligands having from about 4 to about 8 carbon atoms are suitable for most separations. A phenyl group has about the same hydrophobicity as a pentyl group, although the selectivity can be different owing to the possibility of pi-pi orbital interaction with aromatic groups on the protein. Selectively may also be affected by the chemistry of the supporting resin.

Ligand density is an important parameter in that it influences not only the strength of the interaction but the capacity of the column as well. The ligand density of the commercially available phenyl or octyl phenyl gels is on the order of 40 pmoles/ml gel bed. Gel capacity is a function of the particular protein in question as well as pH, temperature and salt type and concentration but generally can be expected to fall in the range of 3-20 mg/ml of gel.

In general, a decrease in temperature decreases the interaction with HIC material. However, any benefit that would accrue by increasing the temperature must also be weighed against adverse effects such an increase may have on the stability of the protein.

In one embodiment, the polypeptides of the invention can be eluted isocratically. In isocratic elution, all compounds begin migration through the column at onset. However, each migrates at a different rate, resulting in faster or slower elution rate. For example, as described in the instant examples, form A can be eluted with the flow through of the column.

In another embodiment, one or more polypeptides of the invention can be bound to the column and eluted, e.g., using stepwise elution or gradient elution. Elution, whether stepwise or in the form of a gradient, can be accomplished in a variety of ways: (a) by changing the salt concentration, (b) by changing the polarity of the solvent or (c) by adding detergents. By decreasing salt concentration adsorbed proteins are eluted in order of increasing hydrophobicity. Changes in polarity may be affected by additions of solvents such as ethylene or propylene glycol or (iso)propanol, thereby decreasing the strength of the hydrophobic interactions. Detergents function as displacers of proteins and have been used primarily in connection with the purification of membrane proteins In performing the separation, the polypeptide mixture can be contacted with the HIC material e.g., using a batch purification technique or using a column. Prior to HIC purification it may be desirable to remove any chaotropic agents or very hydrophobic substances, e.g., by passing the mixture through a precolumn.

For example, for batch purification, HIC material is prepared in or equilibrated to the desired starting buffer. A slurry of the HIC material is obtained. The polypeptide solution is contacted with the slurry to adsorb at least one of the polypeptides to be separated to the HIC material. The solution containing the polypeptides that do not bind to the HIC material is separated from the slurry, e.g., by allowing the slurry to settle and removing the supernatant. The slurry can be subjected to one or more washing steps. If desired, the slurry can be contacted with a solution of lower conductivity to desorb polypeptides that have bound to the HIC material. In order to elute bound polypeptides, the salt concentration can be decreased.

In one embodiment, the HIC material can be packed in a column. A mixture comprising the polypeptides to be separated can be applied to the column allowing at least one of the polypeptides to be separated to adsorb to the column. The polypeptides that do not adsorb to the column pass through and can be collected. In order to elute bound polypeptides, the salt concentration can be decreased, e.g., in a step-wise fashion or using a salt gradient.

Since form B is more hydrophobic than form A, it adsorbs irreversibly to the stationary phase using approximately 0.7 M (e.g., 0.73M)Ammonium Sulfate/20 mM Sodium Phosphate, pH 4.0 to pH 8.0 as the mobile phase. Form A binds to a lesser extent to the stationary phase under these conditions and is therefore eluted isocratically, i.e. it leaves the column with the flowthrough fraction. Subsequent to the isocratic elution of form A, omitting Ammonium sulfate from the mobile phase desorbs form B.

In an exemplary purification scheme, the HIC material is equilibrated in a buffer comprising a salt concentration yielding a conductivity of from between about 160 to about 110, preferably from between about 140 to about 115, even more preferably from between about 130 or about 120 to about 117 mS/cm. For example, an exemplary starting solution comprises a salt concentration of approximately 1M to 0.7M, e.g., 1M to 0.7M ammonium sulfate. In a preferred embodiment, the solution comprising the mixture of polypeptides to be separated is also brought to the same, or approximately the same conductivity (e.g., using a concentrated stock solution of salt). Under these conditions, Form A is eluted from the column at a conductivity of about 120 mS/cm. In order to elute Form B, a stepwise or linear gradient of reducing ammonium sulfate content can be applied to the column. Form B elutes at a conductivity of approximately 115 to approximately 100 mS/cm.

In one embodiment, the subject purification method yields a composition comprising polypeptide molecules having at least two target binding sites and two heavy chain portions, wherein the heavy chain portions lack CH2 domains and wherein greater than about 50% of the molecules are present in a form in which the two heavy chain portions are linked via at least one interchain disulfide linkage. In another embodiment, greater than about 60% of the molecules are present in a form in which the two heavy chain portions are linked via at least one interchain disulfide linkage. In another embodiment, greater than about 70% of the molecules are present in a form in which the two heavy chain portions are linked via at least one interchain disulfide linkage. In another embodiment, greater than about 80% of the molecules are present in a form in which the two heavy chain portions are linked via at least one interchain disulfide linkage. In another embodiment, greater than about 90% of the molecules are present in a form in which the two heavy chain portions are linked via at least one interchain disulfide linkage.

In one embodiment, the subject purification method yields a composition comprising recombinant polypeptide molecules having at least two target binding sites and two heavy chain portions, wherein greater than about 99% of the molecules are present in a form in which the two heavy chain portions are linked via at least one interchain disulfide linkage.

In one embodiment, the subject purification method yields a composition comprising polypeptide molecules having at least two target binding sites and two heavy chain portions, wherein greater than about 95% of the molecules are present in a form in which the two heavy chain portions are linked via at least one interchain disulfide linkage, and wherein the heavy chain portions of the polypeptides are derived from an antibody of the IgG4 isotype.

In one embodiment, the subject purification method yields a composition comprising polypeptide molecules having two light chain portions and two heavy chain portions, wherein the heavy chain portions lack CH2 domains and wherein greater than about 80% of the molecules are present in a form in which the two heavy chain portions are not linked via at least one interchain disulfide linkage.

In another aspect, the instant invention also provides methods for monitoring the results of purification and/or preferential biosynthesis comprising measuring the relative amounts of Form A and Form B in a composition. Form A and Form B can be measured, e.g., as described herein using non-reducing SDS polyacrylamide gel electrophoresis or mass spectrometry.

V. Labeling or Conjugation of Polypeptides

The polypeptide molecules of the present invention may be used in non-conjugated form or may conjugated to at least one of a variety of molecules, e.g., to facilitate antigen detection or for imaging or therapy of the patient. The polypeptides of the invention can be labeled or conjugated either before or after purification, when purification is performed. In particular, the polypeptides of the present invention may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or antibodies wherein the resulting molecule binds to both the neoplastic cell and an effector cell such as a T cell), or PEG. In another embodiment, a polypeptide of the invention can be conjugated to a molecule that decreases vascularization of tumors. In other embodiments, the disclosed compositions may comprise polypeptides of the invention coupled to drugs or prodrugs. Still other embodiments of the present invention comprise the use of polypeptides of the invention conjugated to specific biotoxins or their cytotoxic fragments such as ricin, gelonin, pseudomonas exotoxin or diphtheria toxin. The selection of which conjugated or unconjugated polypeptide to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy cells in solid tumors as well as lymphomas/leukemias in animal models, and in some cases in humans. Exemplary radioisotopes include: $^{90}Y$, $^{125}I$, $^{131}I$, $^{123}I$, $^{111}I$, $^{105}Rh$, $^{153}Sm$, $^{67}Ga$, $^{166}Ho$, $^{177}Lu$, $^{186}Re$ and $^{188}Re$. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

With respect to the use of radiolabeled conjugates in conjunction with the present invention, polypeptides of the invention may be directly labeled (such as through iodination) or may be labeled indirectly through the use of a chelating agent. As used herein, the phrases "indirect labeling" and "indirect labeling approach" both mean that a chelating agent is covalently attached to a molecule and at least one radionuclide is associated with the chelating agent. Such chelating agents are typically referred to as bifunctional chelating agents as they bind both the polypeptide and the radioisotope. Particularly preferred chelating agents comprise 1-isothiocymatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}In$ and $^{90}Y$.

As used herein, the phrases "direct labeling" and "direct labeling approach" both mean that a radionuclide is covalently attached directly to a polypeptide (typically via an amino acid residue). More specifically, these linking technologies include random labeling and site-directed labeling. In the latter case, the labeling is directed at specific sites on the polypeptide, such as the N-linked sugar residues present only on the Fc portion of the conjugates. Further, various direct labeling techniques and protocols are compatible with the instant invention. For example, Technetium-99m labeled polypeptides may be prepared by ligand exchange processes, by reducing pertechnate ($TcO_4^-$) with stannous ion solution, chelating the reduced technetium onto a Sephadex column and applying the polypeptides to this column, or by batch labeling techniques, e.g. by incubating pertechnate, a reducing agent such as $SnCl_2$, a buffer solution such as a sodium-potassium phthalate-solution, and the molecules. In any event, preferred radionuclides for directly labeling polypeptides are well known in the art and a particularly preferred radionuclide for direct labeling is $^{131}I$ covalently attached via tyrosine residues. Polypeptides according to the invention may be derived, for example, with radioactive sodium or potassium iodide and a chemical oxidizing agent, such as sodium hypochlorite, chloramine T or the like, or an enzymatic oxidizing agent, such as lactoperoxidase, glucose oxidase and glucose. However, for the purposes of the present invention, the indirect labeling approach is particularly preferred. Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, 5,434,287 and 5,124,471 of Gansow also relate to polysubstituted DTPA chelates. These patents are incorporated herein in their entirety. Other examples of compatible metal chelators are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like. Cyclohexyl-DTPA or CHX-DTPA is particularly preferred. Still other compatible chelators, including those yet to be discovered, may easily be discerned by a skilled artisan and are clearly within the scope of the present invention.

Compatible chelators, including the specific bifunctional chelator used to facilitate chelation in co-pending application Ser. Nos. 08/475,813, 08/475,815 and 08/478,967, are preferably selected to provide high affinity for trivalent metals, exhibit increased tumor-to-non-tumor ratios and decreased bone uptake as well as greater in vivo retention of radionuclide at target sites, i.e., B-cell lymphoma tumor sites. However, other bifunctional chelators that may or may not possess all of these characteristics are known in the art and may also be beneficial in tumor therapy. It will also be appreciated that, in accordance with the teachings herein, polypeptides may be conjugated to different radiolabels for diagnostic and therapeutic purposes. To this end the aforementioned co-pending applications, herein incorporated by reference in their entirety, disclose radiolabeled therapeutic conjugates for diagnostic "imaging" of tumors before administration of therapeutic molecule. "In2B8" conjugate comprises a murine monoclonal antibody, 2B8, specific to human CD20 antigen, that is attached to $^{111}In$ via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}In$ is particularly preferred as a diagnostic radionuclide because between about 1 to about 10 mCi can be safely administered without detectable toxicity; and the imaging data is generally predictive of subsequent $^{90}Y$-labeled antibody distribution.

Most imaging studies utilize 5 mCi $^{111}$In-labeled antibody, because this dose is both safe and has increased imaging efficiency compared with lower doses, with optimal imaging occurring at three to six days after antibody administration. See, for example, Murray, *J. Nuc. Med.* 26: 3328 (1985) and Carraguillo et al., *J. Nuc. Med.* 26: 67 (1985).

As indicated above, a variety of radionuclides are applicable to the present invention and those skilled in the can readily determine which radionuclide is most appropriate under various circumstances. For example, $^{131}$I is a well known radionuclide used for targeted immunotherapy. However, the clinical usefulness of $^{131}$I can be limited by several factors including: eight-day physical half-life; dehalogenation of iodinated antibody both in the blood and at tumor sites; and emission characteristics (e.g., large gamma component) which can be suboptimal for localized dose deposition in tumor. With the advent of superior chelating agents, the opportunity for attaching metal chelating groups to proteins has increased the opportunities to utilize other radionuclides such as $^{111}$In and $^{90}$Y. $^{90}$Y provides several benefits for utilization in radioimmunotherapeutic applications: the 64 hour half-life of $^{90}$Y is long enough to allow accumulation by tumor and, unlike e.g., $^{131}$I, $^{90}$Y is a pure beta emitter of high energy with no accompanying gamma irradiation in its decay, with a range in tissue of 100 to 1,000 cell diameters. Furthermore, the minimal amount of penetrating radiation allows for outpatient administration of $^{90}$Y-labeled molecules. Additionally, internalization of labeled polypeptides is not required for cell killing, and the local emission of ionizing radiation should be lethal for adjacent tumor cells lacking the target antigen.

Those skilled in the art will appreciate that these non-radioactive conjugates may also be assembled using a variety of techniques depending on the selected agent to be conjugated. For example, conjugates with biotin are prepared e.g. by reacting the polypeptides with an activated ester of biotin such as the biotin N-hydroxysuccinimide ester. Similarly, conjugates with a fluorescent marker may be prepared in the presence of a coupling agent, e.g. those listed above, or by reaction with an isothiocyanate, preferably fluorescein-isothiocyanate. Conjugates of the polypeptides of the invention with cytostatic/cytotoxic substances and metal chelates are prepared in an analogous manner.

Preferred agents for use in the present invention are cytotoxic drugs, particularly those which are used for cancer therapy. As used herein, "a cytotoxin or cytotoxic agent" means any agent that is detrimental to the growth and proliferation of cells and may act to reduce, inhibit or destroy a cell or malignancy. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. Any cytotoxin that acts to retard or slow the growth of immunoreactive cells or malignant cells is within the scope of the present invention.

Exemplary cytotoxins include, in general, cytostatic agents, alkylating agents, antimetabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. Other preferred classes of cytotoxic agents include, for example, the maytansinoid family of drugs. Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, caminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. As noted previously, one skilled in the art may make chemical modifications to the desired compound in order to make reactions of that compound more convenient for purposes of preparing conjugates of the invention.

One example of particularly preferred cytotoxins comprise members or derivatives of the enediyne family of anti-tumor antibiotics, including calicheamicin, esperamicins or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present only on the Fc portion of the constructs. Such site-directed linking methods have the advantage of reducing the possible effects of linkage on the binding properties of the constructs.

As previously alluded to, compatible cytotoxins may comprise a prodrug. As used herein, the term "prodrug" refers to a precursor or derivative form of a pharmaceutically active substance that is less cytotoxic to tumor cells compared to the parent drug and is capable of being enzymatically activated or converted into the more active parent form. Prodrugs compatible with the invention include, but are not limited to, phosphate-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. Further examples of cytotoxic drugs that can be derivatized into a prodrug form for use in the present invention comprise those chemotherapeutic agents described above.

Among other cytotoxins, it will be appreciated that polypeptides can also be associated with a biotoxin such as ricin subunit A, abrin, diptheria toxin, botulinum, cyanginosins, saxitoxin, shigatoxin, tetanus, tetrodotoxin, trichothecene, verrucologen or a toxic enzyme. Preferably, such constructs will be made using genetic engineering techniques that allow for direct expression of the binding molecule-toxin construct. Other biological response modifiers that may be associated with the polypeptides of the invention of the present invention comprise cytokines such as lymphokines and interferons. In view of the instant disclosure it is submitted that one skilled in the art could readily form such constructs using conventional techniques.

Another class of compatible cytotoxins that may be used in conjunction with the disclosed polypeptides are radiosensitizing drugs that may be effectively directed to tumor or immunoreactive cells. Such drugs enhance the sensitivity to ionizing radiation, thereby increasing the efficacy of radiotherapy. An conjugate internalized by the tumor cell would deliver the radiosensitizer nearer the nucleus where radiosensitization would be maximal. The unbound radiosensitizer linked polypeptides of the invention would be cleared quickly from the blood, localizing the remaining radiosensitization agent in the target tumor and providing minimal uptake in normal tissues. After rapid clearance from the blood, adjunct radiotherapy would be administered in one of three ways: 1.) external beam radiation directed specifically to the tumor, 2.) radioactivity directly implanted in the tumor or 3.) systemic radioimmunotherapy with the same targeting molecule. A potentially attractive variation of this approach would be the attachment of a therapeutic radioisotope to the radiosensitized immunoconjugate, thereby providing the convenience of administering to the patient a single drug.

In one embodiment, a moiety that enhances the stability or efficacy of the polypeptide can be conjugated. For example, in one embodiment, PEG can be conjugated to the polypeptides of the invention to increase their half-life in vivo. Leong, S. R., et al. 2001. *Cytokine* 16:106; 2002*; Adv. in Drug Deliv. Rev.* 54:531; or Weir et al. 2002. Biochem. Soc. Transactions 30:512.

VI. Administration of Polypeptides

Methods of preparing and administering polypeptides of the invention to a subject are well known to or are readily determined by those skilled in the art. The route of administration of the polypeptide of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders. Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy. For passive immunization with an antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Polypeptides of the invention can be administered on multiple occasions. Intervals between single dosages can be weekly, monthly or yearly. Intervals can also be irregular as indicated by measuring blood levels of polypeptide or antigen in the patient. In some methods, dosage is adjusted to achieve a plasma polypeptide concentration of 1-1000 μg/ml and in some methods 25-300 μg/ml. Alternatively, binding molecules can be administered as a sustained release formulation, in which case less frequent administration is required. Dosage and frequency vary depending on the half-life of the molecule in the patient. In general, humanized antibodies show the longest half-life, followed by chimeric antibodies and non-human antibodies. In one embodiment, the binding molecules of the invention can be administered in unconjugated form, In another embodiment, the polypeptides of the invention can be administered multiple times in conjugated form. In still another embodiment, the binding molecules of the invention can be administered in unconjugated form, then in conjugated form, or vice versa.

The dosage and frequency of administration can vary depending on whether the treatment is prophylactic or therapeutic. In prophylactic applications, compositions containing the present polypeptides or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a polypeptide of the invention (e.g., in a vector). Doses for nucleic acids encoding polypeptides range from about 10 ng to 1 g, 100 ng to 100 mg, 1 μg to 10 mg, or 30-300 μg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of molecules. In some methods, particular therapeutic molecules are injected directly into the cranium. In some methods, molecules are administered as a sustained release composition or device, such as a Medipad™ device.

Agents of the invention can optionally be administered in combination with other agents that are effective in treating the disorder or condition in need of treatment (e.g., prophylactic or therapeutic).

Effective single treatment dosages (i.e., therapeutically effective amounts) of $^{90}$Y-labeled polypeptides of the invention range from between about 5 and about 75 mCi, more preferably between about 10 and about 40 mCi. Effective single treatment non-marrow ablative dosages of $^{131}$I-labeled antibodies range from between about 5 and about 70 mCi, more preferably between about 5 and about 40 mCi. Effective single treatment ablative dosages (i.e., may require autologous bone marrow transplantation) of $^{131}$I-labeled antibodies range from between about 30 and about 600 mCi, more preferably between about 50 and less than about 500 mCi. In conjunction with a chimeric antibody, owing to the longer circulating half life vis-á-vis murine antibodies, an effective single treatment non-marrow ablative dosages of iodine-131 labeled chimeric antibodies range from between about 5 and about 40 mCi more preferably less than about 30 mCi. Imaging criteria for, e.g., the $^{111}$In label, are typically less than about 5 mCi.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$Cu, $^{77}$Br, $^{81}$Rb, $^{81}$Kr, $^{87}$Sr, $^{113}$In, $^{127}$Cs, $^{129}$Cs, $^{132}$I, $^{197}$Hg, $^{203}$Pb, $^{206}$Bi, $^{177}$Lu, $^{186}$Re, $^{212}$Pb, $^{212}$Bi, $^{47}$Sc, $^{105}$Rh, $^{109}$Pd, $^{153}$Sm, $^{188}$Re, $^{199}$Au, $^{225}$Ac, $^{211}$At, and $^{213}$Bi. In this respect alpha, gamma and beta emitters are all compatible within the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{231}$I, $^{99}$Tc, $^{43}$K, $^{52}$Fe, $^{67}$Ga, $^{68}$Ga, as well as $^{111}$In. Antibodies have also been labeled with a variety of radionuclides for potential use in targeted immunotherapy (Peirersz et al. *Immunol. Cell Biol.* 65: 111-125 (1987)). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

Whether or not the polypeptides of the invention are used in a conjugated or unconjugated form, it will be appreciated that a major advantage of the present invention is the ability to use these polypeptides in myelosuppressed patients, especially those who are undergoing, or have undergone, adjunct therapies such as radiotherapy or chemotherapy. That is, the beneficial delivery profile (i.e. relatively short serum dwell time, high binding affinity and enhanced localization) of the polypeptides makes them particularly useful for treating patients that have reduced red marrow reserves and are sensitive to myelotoxicity. In this regard, the unique delivery profile of the polypeptides make them very effective for the administration of radiolabeled conjugates to myelosuppressed cancer patients. As such, the polypeptides of the invention are useful in a conjugated or unconjugated form in patients that have previously undergone adjunct therapies such as external beam radiation or chemotherapy. In other preferred embodiments, the polypeptides (again in a conjugated or unconjugated form) may be used in a combined therapeutic regimen with chemotherapeutic agents. Those skilled in the art will appreciate that such therapeutic regimens may comprise the sequential, simultaneous, concurrent or coextensive administration of the disclosed molecules and one or more chemotherapeutic agents. Particularly preferred embodiments of this aspect of the invention will comprise the administration of a radiolabeled polypeptide.

While the polypeptides may be administered as described immediately above, it must be emphasized that in other embodiments conjugated and unconjugated polypeptides may be administered to otherwise healthy patients as a first line therapeutic agent. In such embodiments the polypeptides may be administered to patients having normal or average red marrow reserves and/or to patients that have not, and are not, undergoing adjunct therapies such as external beam radiation or chemotherapy.

However, as discussed above, selected embodiments of the invention comprise the administration of polypeptides to myelosuppressed patients or in combination or conjunction with one or more adjunct therapies such as radiotherapy or chemotherapy (i.e. a combined therapeutic regimen). As used herein, the administration of polypeptides in conjunction or combination with an adjunct therapy means the sequential, simultaneous, coextensive, concurrent, concomitant or contemporaneous administration or application of the therapy and the disclosed molecules. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the present invention. Conversely, cytotoxin associated polypeptides could be administered intravenously followed by tumor localized external beam radiation. In yet other embodiments, the polypeptide may be administered concurrently with one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard it will be appreciated that the combination of the polypeptide (with or without cytotoxin) and the chemotherapeutic agent may be administered in any order and within any time frame that provides a therapeutic benefit to the patient. That is, the chemotherapeutic agent and polypeptide may be administered in any order or concurrently. In selected embodiments the polypeptides of the present invention will be administered to patients that have previously undergone chemotherapy. In yet other embodiments, the polypeptides and the chemotherapeutic treatment will be administered substantially simultaneously or concurrently. For example, the patient may be given the binding molecule while undergoing a course of chemotherapy. In preferred embodiments the binding molecule will be administered within 1 year of any chemotherapeutic agent or treatment. In other preferred embodiments the polypeptide will be administered within 10, 8, 6, 4, or 2 months of any chemotherapeutic agent or treatment. In still other preferred embodiments the polypeptide will be administered within 4, 3, 2 or 1 week of any chemotherapeutic agent or treatment. In yet other embodiments the polypeptide will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

Moreover, in accordance with the present invention a myelosuppressed patient shall be held to mean any patient exhibiting lowered blood counts. Those skilled in the art will appreciate that there are several blood count parameters conventionally used as clinical indicators of myelosuppresion and one can easily measure the extent to which myelosuppresion is occurring in a patient. Examples of art accepted myelosuppression measurements are the Absolute Neutrophil Count (ANC) or platelet count. Such myelosuppression or partial myeloablation may be a result of various biochemical disorders or diseases or, more likely, as the result of prior chemotherapy or radiotherapy. In this respect, those skilled in the art will appreciate that patients who have undergone traditional chemotherapy typically exhibit reduced red marrow reserves. As discussed above, such subjects often cannot be treated using optimal levels of cytotoxin (i.e. radionuclides) due to unacceptable side effects such as anemia or immunosuppression that result in increased mortality or morbidity.

More specifically conjugated or unconjugated polypeptides of the present invention may be used to effectively treat patients having ANCs lower than about 2000/mm$^3$ or platelet counts lower than about 150,000/mm$^3$. More preferably the polypeptides of the present invention may be used to treat patients having ANCs of less than about 1500/mm$^3$, less than about 1000/mm$^3$ or even more preferably less than about 500/mm$^3$. Similarly, the polypeptides of the present invention may be used to treat patients having a platelet count of less than about 75,000/mm$^3$, less than about 50,000/mm$^3$ or even less than about 10,000/mm$^3$. In a more general sense, those skilled in the art will easily be able to determine when a patient is myelosuppressed using government implemented guidelines and procedures.

As indicated above, many myelosuppressed patients have undergone courses of treatment including chemotherapy, implant radiotherapy or external beam radiotherapy. In the case of the latter, an external radiation source is for local irradiation of a malignancy. For radiotherapy implantation methods, radioactive reagents are surgically located within the malignancy, thereby selectively irradiating the site of the disease. In any event, the disclosed polypeptides may be used to treat disorders in patients exhibiting myelosuppression regardless of the cause.

In this regard it will further be appreciated that the polypeptides of the instant invention may be used in conjunction or combination with any chemotherapeutic agent or agents (e.g. to provide a combined therapeutic regimen) that eliminates, reduces, inhibits or controls the growth of neoplastic cells in vivo. As discussed, such agents often result in the reduction of red marrow reserves. This reduction may be offset, in whole or in part, by the diminished myelotoxicity of the compounds of the present invention that advantageously allow for the aggressive treatment of neoplasias in such patients. In other preferred embodiments the radiolabeled immunoconjugates disclosed herein may be effectively used with radiosensitizers that increase the susceptibility of the neoplastic cells to radionuclides. For example, radiosensitizing compounds may be administered after the radiolabeled binding molecule has been largely cleared from the bloodstream but still remains at therapeutically effective levels at the site of the tumor or tumors.

With respect to these aspects of the invention, exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), Ch1VPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas*, in HARRISON'S PRINCIPLES OF INTERNAL MEDICINE 1774-1788 (Kurt J. Isselbacher et al., eds., 13$^{th}$ ed. 1994) and V. T. DeVita et al., (1997) and the references cited therein for standard dosing and scheduling. These therapies can be used unchanged, or altered as needed for a particular patient, in combination with one or more polypeptides of the invention as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), Pro-MACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, cisplatin, etoposide and ifosfamide given alone or in combination. In relapsed or aggressive forms of certain neoplastic disorders the following protocols are often used: IMVP-16 (ifosfamide, methotrexate and etoposide), MIME (methylgag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9$^{th}$ ed. 1996). As previously discussed, the polypeptides of the present invention, immunoreactive fragments or recombinants thereof may be administered in a pharmaceutically effective amount for the in vivo treatment of mammalian disorders. In this regard, it will be appreciated that the disclosed binding molecules will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of the polypeptide, immunoreactive fragment or recombinant thereof, conjugated or unconjugated to a therapeutic agent, shall be held to mean an amount sufficient to achieve effective binding to an antigen and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the polypeptides of the invention may be administered to a human or other animal in accordance with the aforementioned methods of treatment in an amount sufficient to produce a therapeutic or prophylactic effect. The binding molecules of the invention can be administered to such human or other animal in a conventional dosage form prepared by combining the binding molecule of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

VII. Methods of Use

The polypeptides of the invention can be used for diagnostic or therapeutic purposes. Preferred embodiments of the present invention provide compounds, compositions, kits and methods for the diagnosis and/or treatment of disorders, e.g., neoplastic disorders in a mammalian subject in need of such treatment. Preferably, the subject is a human.

The polypeptides of the instant invention will be useful in a number of different applications. For example, in one embodiment, the subject binding molecules should be useful for reducing or eliminating cells bearing an epitope recognized by a binding molecule of the invention. In another embodiment, the subject binding molecules are effective in reducing the concentration of or eliminating soluble antigen in the circulation In one embodiment, tumor size, inhibiting tumor growth and/or prolonging the survival time of tumor-bearing animals. Accordingly, this invention also relates to a method of treating tumors in a human or other animal by administering to such human or animal an effective, non-toxic amount of polypeptide. One skilled in the art would be able, by routine experimentation, to determine what an effective, non-toxic amount of polypeptide would be for the purpose of treating malignancies. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the molecule to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

For purposes of clarification "mammal" refers to any animal classified as a mammal, including humans, domestic and farm animals, and zoo, sports, or pet animals, such as dogs, horses, cats, cows, etc. Preferably, the mammal is human. "Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

As discussed above, the polypeptides of the present invention may be immunoreactive with one or more tumor antigens or antigens associated with immune disorders. For example, for neoplastic disorders, the antigen binding site (i.e. the variable region or immunoreactive fragment or recombinant thereof) of the disclosed polypeptides binds to a selected tumor associated antigen at the site of the malignancy. Similarly, in immune (including autoimmune) disorders the disclosed polypeptides will bind to selected markers on the offending cells. Given the number of reported antigens associated with neoplasias and immune disorders, and the number of related antibodies, those skilled in the art will appreciate that the presently disclosed polypeptides may therefore be derived from any one of a number of whole antibodies. More generally, polypeptides useful in the present invention may be obtained or derived from any antibody (including those previously reported in the literature) that reacts with a molecule or marker associated with the selected condition. Further, the parent or precursor antibody, or fragment thereof, used to generate the disclosed polypeptides may be murine, human, chimeric, humanized, non-human primate or primatized. In other preferred embodiments the polypeptides of the present invention may comprise single chain antibody constructs (such as that disclosed in U.S. Pat. No. 5,892,019 which is incorporated herein by reference) having altered constant domains as described herein. Consequently, any of these types of antibodies modified in accordance with the teachings herein is compatible with the instant invention.

As used herein, "tumor associated antigens" means any antigen which is generally associated with tumor cells, i.e., occurring at the same or to a greater extent as compared with normal cells. More generally, tumor associated antigens comprise any antigen that provides for the localization of immunoreactive antibodies at a neoplastic cell irrespective of its expression on non-malignant cells. Such antigens may be relatively tumor specific and limited in their expression to the surface of malignant cells. Alternatively, such antigens may be found on both malignant and non-malignant cells. For example, CD20 is a pan B antigen that is found on the surface of both malignant and non-malignant B cells that has proved to be an extremely effective target for immunotherapeutic antibodies for the treatment of non-Hodgkin's lymphoma. In this respect, pan T cell antigens such as CD2, CD3, CD5, CD6 and CD7 also comprise tumor associated antigens within the meaning of the present invention. Still other exemplary tumor associated antigens comprise but not limited to MAGE-1, MAGE-3, MUC-1, HPV 16, HPV E6 & E7, TAG-72, CEA, L6-Antigen, CD19, CD22, CD37, CD52, HLA-DR, EGF Receptor and HER2 Receptor. In many cases immunoreactive antibodies for each of these antigens have been reported in the literature. Those skilled in the art will appreciate that each of these antibodies may serve as a precursor for polypeptides of the invention in accordance with the present invention.

The polypeptides of the present invention preferably associate with, and bind to, tumor or immune associated antigens as described above. Accordingly, as will be discussed in some detail below the polypeptides of the present invention may be derived, generated or fabricated from any one of a number of antibodies that react with tumor associated antigens. In preferred embodiments the polypeptides are modified or domain deleted antibodies that are derived using common genetic engineering techniques whereby at least a portion of one or more constant region domains are deleted or altered so as to provide the desired biochemical characteristics such as reduced serum half-life. More particularly, one skilled in the art may readily isolate the genetic sequence corresponding to the variable and/or constant regions of the subject antibody and delete or alter the appropriate nucleotides to provide polypeptides of the invention for use as monomeric subunits in accordance with the instant invention. It will further be appreciated that compatible polypeptides of the invention may be expressed and produced on a clinical or commercial scale using well-established protocols.

Previously reported antibodies that react with tumor associated antigens may be altered as described herein to provide the polypeptides of the present invention. Exemplary antibodies that may be used to provide antigen binding regions for, generate or derive the disclosed polypeptides include, but are not limited to 2B8 and C2B8 (Zevalin® and Rituxan®, IDEC Pharmaceuticals Corp., San Diego), Lym 1 and Lym 2 (Techniclone), LL2 (Immunomedics Corp., New Jersey), HER2 (Herceptin®, Genentech Inc., South San Francisco), B1 (Bexxar®, Coulter Pharm., San Francisco), Campath® (Millennium Pharmaceuticals, Cambridge) MB1, BH3, B4, B72.3 (Cytogen Corp.), CC49 (National Cancer Institute) and 5E10 (University of Iowa). Other antibody binding sites that can be incorporated into the subject binding molecules include: Orthoclone OKT3 (CD3), ReoPro (GpIIb/gIIa), Zenapax (C25), Remicade (TNF-a), Simulect (CD25), Synagis (RSV), Mylotarg (CD33), and Campath (CD52). In preferred embodiments, the polypeptides of the present invention will bind to the same tumor associated antigens as the antibodies enumerated immediately above. In particularly preferred embodiments, the polypeptides will be derived from or bind the same antigens as 2B8, C2B8, CC49 and C5E10 and, even more preferably, will lack all or part of a CH2 domain.

In one embodiment, a binding molecule of the invention binds to the CD23 (U.S. Pat. No. 6,011,138). In a preferred embodiment, a binding molecule of the invention binds to the same epitope as the 5E8 antibody. In another embodiment, a binding molecule of the invention comprises at least one CDR from an anti-CD23 antibody, e.g., the 5E8 antibody.

In one embodiment, a binding molecule of the invention binds to the CRIPTO-I antigen (WO02/088170A2 or WO03/083041A2). In a preferred embodiment, a binding molecule of the invention binds to the same epitope as the B3F6 antibody. In another embodiment, a binding molecule of the invention comprises at least one CDR from an anti-CRIPTO-I antibody, e.g., the B3F6 antibody.

In a first preferred embodiment, the polypeptide will bind to the same tumor associated antigen as Rituxan®. Rituxan® (also known as, rituximab, IDEC-C2B8 and C2B8) was the first FDA-approved monoclonal antibody for treatment of human B-cell lymphoma (see U.S. Pat. Nos. 5,843,439; 5,776,456 and 5,736,137 each of which is incorporated herein by reference). Y2B8 (90Y labeled 2B8; Zevalin®; ibritumomab tiuxetan) is the murine parent of C2B8. Rituxan® is a chimeric, anti-CD20 monoclonal antibody which is growth inhibitory and reportedly sensitizes certain lymphoma cell lines for apoptosis by chemotherapeutic agents in vitro. The antibody efficiently binds human complement, has strong FcR binding, and can effectively kill human lymphocytes in vitro via both complement dependent (CDC) and antibody-dependent (ADCC) mechanisms (Reff et al., Blood 83: 435-445 (1994)). Those skilled in the art will appreciate that dimeric variants (homodimers or heterodimers) of C2B8 or 2B8, modified according to the instant disclosure, may be used in conjugated or unconjugated forms to effectively treat patients presenting with CD20+ malignancies. More generally, it must be reiterated that the polypeptides disclosed herein may be used in either a "naked" or unconjugated state or conjugated to a cytotoxic agent to effectively treat any one of a number of disorders. In other preferred embodiments of the present invention, the polypeptide of the invention will be derived from, or bind to, the same tumor associated antigen as CC49. As previously alluded to, CC49 binds human tumor associated antigen TAG-72 which is associated with the surface of certain tumor cells of human origin, specifically the LS174T tumor cell line. LS174T [American Type Culture Collection (herein ATCC) No. CL 188] is a variant of the LS180 (ATCC No. CL 187) colon adenocarcinoma line.

It will further be appreciated that numerous murine monoclonal antibodies have been developed which have binding specificity for TAG-72. One of these monoclonal antibodies, designated B72.3, is a murine IgG1 produced by hybridoma B72.3 (ATCC No. HB-8108). B72.3 is a first generation monoclonal antibody developed using a human breast carcinoma extract as the immunogen (see Colcher et al., Proc. Natl. Acad. Sci. (USA), 78:3199-3203 (1981); and U.S. Pat. Nos. 4,522,918 and 4,612,282 each of which is incorporated herein by reference). Other monoclonal antibodies directed against TAG-72 are designated "CC" (for colon cancer). As described by Schlom et al. (U.S. Pat. No. 5,512,443 which is incorporated herein by reference) CC monoclonal antibodies are a family of second generation murine monoclonal antibodies that were prepared using TAG-72 purified with B72.3. Because of their relatively good binding affinities to TAG-72, the following CC antibodies have been deposited at the ATCC, with restricted access having been requested: CC49 (ATCC No. HB 9459); CC 83 (ATCC No. HB 9453); CC46 (ATCC No. HB 9458); CC92 (ATTCC No. HB 9454); CC30 (ATCC No. HB 9457); CC11 (ATCC No. 9455); and CC15 (ATCC No. HB 9460). U.S. Pat. No. 5,512,443 further teaches that the disclosed antibodies may be altered into their chimeric form by substituting, e.g., human constant regions (Fc) domains for mouse constant regions by recombinant DNA techniques known in the art. Besides disclosing murine and chimeric anti-TAG-72 antibodies, Schlom et al. have also produced variants of a humanized CC49 antibody as disclosed in PCT/US99/25552 and single chain constructs as disclosed in U.S. Pat. No. 5,892,019 each of which is also incorporated herein by reference. Those skilled in the art will appreciate that each of the foregoing antibodies, constructs or recombinants, and variations thereof, may be modified and used to provide polypeptides in accordance with the present invention.

In addition to the anti-TAG-72 antibodies discussed above, various groups have also reported the construction and partial characterization of domain-deleted CC49 and B72.3 antibodies (e.g., Calvo et al. Cancer Biotherapy, 8(1):95-109 (1993), Slavin-Chiorini et al. Int. J. Cancer 53:97-103 (1993) and Slavin-Chiorini et al. Cancer. Res. 55:5957-5967 (1995

Still other preferred embodiments of the present invention comprise modified antibodies that are derived from or bind to the same tumor associated antigen as C5E10. As set forth in co-pending application Ser. No. 09/104,717, C5E10 is an antibody that recognizes a glycoprotein determinant of approximately 115 kDa that appears to be specific to prostate tumor cell lines (e.g. DU145, PC3, or ND1). Thus, in conjunction with the present invention, polypeptides (e.g. CH2 domain-deleted antibodies) that specifically bind to the same tumor associated antigen recognized by C5E10 antibodies could be produced and used in a conjugated or unconjugated form for the treatment of neoplastic disorders. In particularly preferred embodiments, the modified antibody will be derived or comprise all or part of the antigen binding region of the C5E10 antibody as secreted from the hybridoma cell line having ATCC accession No. PTA-865. The resulting modified antibody could then be conjugated to a radionuclide as described below and administered to a patient suffering from prostate cancer in accordance with the methods herein.

In general, the disclosed invention may be used to prophylactically or therapeutically treat any neoplasm comprising an antigenic marker that allows for the targeting of the cancerous cells by the binding molecule. Exemplary cancers that may be treated include, but are not limited to, prostate, gastric carcinomas such as colon, skin, breast, ovarian, lung and pancreatic. More particularly, the binding molecules of the instant invention may be used to treat Kaposi's sarcoma, CNS neoplasias (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the ovary, Wilm's tumor or small cell lung carcinoma. It will be appreciated that appropriate polypeptides may be derived for tumor associated antigens related to each of the forgoing neoplasias without undue experimentation in view of the instant disclosure. Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the compounds and methods of the present invention are particularly effective in treating a variety of B-cell lymphomas, including low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies bearing compatible tumor associated antigens.

Besides neoplastic disorders, the polypeptides of the instant invention are particularly effective in the treatment of autoimmune disorders or abnormal immune responses. In this regard, it will be appreciated that the polypeptide of the present invention may be used to control, suppress, modulate or eliminate unwanted immune responses to both external and autoantigens. For example, in one embodiment, the antigen is an autoantigen. In another embodiment, the antigen is an allergen. In yet other embodiments, the antigen is an alloantigen or xenoantigen. Use of the disclosed polypeptides to reduce an immune response to alloantigens and xenoantigens is of particular use in transplantation, for example to inhibit rejection by a transplant recipient of a donor graft, e.g. a tissue or organ graft or bone marrow transplant. Additionally, suppression or elimination of donor T cells within a bone marrow graft is useful for inhibiting graft versus host disease.

In yet other embodiments the polypeptides of the present invention may be used to treat immune disorders that include, but are not limited to, allergic bronchopulmonary aspergillosis; Allergic rhinitis Autoimmune hemolytic anemia; Acanthosis nigricans; Allergic contact dermatitis; Addison's disease; Atopic dermatitis; Alopecia areata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoiimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetiformis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X, Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythema-tosus; Pemphigus foliaceus; Pemphigus vulgaris; Pigeon breeder's disease; Pneumonitis, hypersensitivity; Polyarteritis nodosa; Polymyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Serum sickness; Sezary syndrome; Sjogren's syndrome; Stevens-Johnson syndrome; Still's disease; Subacute sclerosing panencephalitis; Sympathetic ophthalmia, Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis and Wiskott-Aldrich syndrome.

In another embodiment, the binding molecules of the invention can be used for pretargeting applications. For example, the same advantages will be apparent in pretargeting applications for chemotherapeutic drug delivery.

For example, in pretargeting a tumor is pretargeted with a binding construct that has affinity for the tumor-associated antigen on the one hand and for, e.g., a radiolabeled hapten on the other. The radiolabeled hapten is administered later, preferably after the binding molecule has cleared (see, e.g., Boerman et al. 2003. J. Nuclear Med. 44:400). In another example, an antibody which is non-toxic, but has been derivitized to react with a drug or prodrug that is toxic only when bound by the binding molecule. Given the biodistribution data in the instant examples, the binding molecules of the invention are well suited to use in pretargeting applications. In one embodiment, a clearing agent could be eliminated from the pretargeting methodology by using the instant binding molecules.

This invention is further illustrated by the following examples which should not be construed as limiting. The contents of all references, patents and published patent applications cited throughout this application are incorporated herein by reference.

EXAMPLES

Example 1

Identification of A and B Isoforms

Solutions of antibody molecules comprise two different isoforms. One form, Form A comprises heavy chain molecules that are linked via at least one disulfide linkage. The other form, Form B, comprises heavy chain molecules that are not linked via at least one disulfide linkage. Form B does not appear or appears at a very low frequency in with intact gamma 1 MAbs, such as Rituxan®. However with domain deleted (dd) constructs having a similar hinge, the frequency of Form B is much higher. These forms can be distinguished using denaturing, non-reducing SDS page. In domain deleted antibody preparations, Form A appears as a 120 kDa dimer while Form B appears as a 60 kDa monomer.

Example 2

Identification of Hinge Region Heterogeneity in CH2 Domain Deleted MAb Fragments Hinge domains can be subdivided into three distinct regions: upper, middle, and lower hinge regions (Roux et al.

J. Immunol. 1998 161:4083). Polypeptide sequences encompassing these regions for IgG1 and IgG3 hinges are shown in Table 1. The IgG3 hinge middle region contains, in addition to the two conserved cysteine residues, a 15 amino acid motif that repeats three times. Amino acid sequences from these regions were used to design synthetic IgG1/IgG3 connecting peptides. These consisted of IgG1 upper hinge residues corresponding to positions 226 through 238, an IgG1 middle hinge corresponding to positions 239 through 241, and a single IgG3 middle hinge repeat motif corresponding to positions 241EE through 242 combined with either an added proline at position 243 or an added proline, alanine, proline at positions 243, 244, and 245, respectively (Kabat numbering system), followed by a flexible Gly/Ser spacer (Table 2). In addition, novel connecting peptides were designed consisting of a serine amino acid residue substituted for the cysteine at positions 239 or 242 combined with either an added proline at position 243 or an added proline, alanine, proline at positions 243, 244, and 245, respectively (Kabat numbering system). Pro243Ala244Pro245 and Pro 243 connecting peptides were also made. The amino acid sequence of the parent CH2 domain deleted humanized CC49 connecting peptide beginning at the first residue of the IgG1 hinge (position 226, Kabat numbering system) to the last residue of the hinge/GlySer connecting peptide is shown in Table 2. Also shown are the various connecting peptide designs by alignment to CC49 with positions of the cysteine residues indicated in Kabat numbering system.

TABLE 1

IgG1, IgG3 and IgG4 Hinge Regions

| IgG | Upper Hinge | Middle Hinge | Lower Hinge |
|---|---|---|---|
| IgG1 | EPKSCDKTHT (SEQ ID NO: 2) | CPPCP (SEQ ID NO: 3) | APELLGGP (SEQ ID NO: 4) |
| IgG3 | ELKTPLGDTTHT (SEQ ID NO: 5) | CPRCP (EPKSCDTPPPCPRCP)$_3$ (SEQ ID NO: 6) | APELLGGP (SEQ ID NO: 4) |
| IgG4 | ESKYGPP (SEQ ID NO: 20) | CPSCP (SEQ ID NO: 21) | APEFLGGP (SEQ ID NO: 22) |

TABLE 2

Hinge Region Connecting Peptide Sequences

| Kabat hinge position: | 226 | 227 | 228 | 229 | 230 | 232 | 235 | 236 | 237 | 238 | 239 | 240 | 241 | 241EE |
|---|---|---|---|---|---|---|---|---|---|---|---|---|---|---|
| IgG1 hinge sequence | E | P | K | S | C | D | K | T | H | T | C | P | P | |
| IgG4 hinge sequence | E | S | K | Y | G | | | | P | | P | C | P | S |
| IgG3 middle hinge sequence | | | | | | | | | | | | | | C |
| Connecting peptide: | | | | | | Connecting peptide sequences | | | | | | | | |
| G1 (Seq. ID NO: 7) | E | P | K | S | C | D | K | T | H | T | C | P | P | |
| G1/G3/Pro243 (Seq. ID NO: 8) | E | P | K | S | C | D | K | T | H | T | C | P | P | C |
| G1/G3/Pro243Ala244Pro245 (Seq. ID NO: 9) | E | P | K | S | C | D | K | T | H | T | C | P | P | C |
| G1/Cys239Ser:Pro243 (Seq. ID NO: 10) | E | P | K | S | C | D | K | T | H | T | S | P | P | |
| G1/Cys239Ser:Pro243Ala244Pro245 (Seq. ID NO: 11) | E | P | K | S | C | D | K | T | H | T | S | P | P | |
| G1/Cys242Ser:Pro243 (Seq. ID NO: 12) | E | P | K | S | C | D | K | T | H | T | C | P | P | |
| G1/Cys242Ser:Pro243Ala244Pro245 (Seq. ID NO: 13) | E | P | K | S | C | D | K | T | H | T | C | P | P | |
| G1/Pro243Ala244Pro245 (Seq. ID NO: 14) | E | P | K | S | C | D | K | T | H | T | C | P | P | |
| G1/Pro243 (Seq. ID NO: 15) | E | P | K | S | C | D | K | T | H | T | C | P | P | |
| G4/G3/Pro243Ala244Pro245 (Seq. ID NO: 23) | E | S | K | Y | G | | | | P | | P | C | P | S | C |

TABLE 2-continued

Hinge Region Connecting Peptide Sequences

| Kabat hinge position: | 241FF | 241G | 241H | 241II | 241JJ | 241KK | 241LL | 241M | 241N | 241O |
|---|---|---|---|---|---|---|---|---|---|---|
| IgG1 hinge sequence | | | | | | | | | | |
| IgG4 hinge sequence | | | | | | | | | | |
| IgG3 middle hinge sequence | P | E | P | K | S | C | D | T | P | P |
| Connecting peptide: | | | | Connecting peptide sequences | | | | | | |
| G1 (Seq. ID NO: 7) | | | | | | | | | | |
| G1/G3/Pro243 (Seq. ID NO: 8) | P | E | P | K | S | C | D | T | P | P |
| G1/G3/Pro243Ala244Pro245 (Seq. ID NO: 9) | P | E | P | K | S | C | D | T | P | P |
| G1/Cys239Ser:Pro243 (Seq. ID NO: 10) | | | | | | | | | | |
| G1/Cys239Ser:Pro243Ala244Pro245 (Seq. ID NO: 11) | | | | | | | | | | |
| G1/Cys242Ser:Pro243 (Seq. ID NO: 12) | | | | | | | | | | |
| G1/Cys242Ser:Pro243Ala244Pro245 (Seq. ID NO: 13) | | | | | | | | | | |
| G1/Pro243Ala244Pro245 (Seq. ID NO: 14) | | | | | | | | | | |
| G1/Pro243 (Seq. ID NO: 15) | | | | | | | | | | |
| G4/G3/Pro243Ala244Pro245 (Seq. ID NO: 23) | P | E | P | K | S | C | D | T | P | P |

| Kabat hinge position: | 241PP | 241Q | 241R | 241SS | 242 | 243 | 244 | 245 | |
|---|---|---|---|---|---|---|---|---|---|
| IgG1 hinge sequence | | | | | C | P | A | P | (SEQ ID NO: 39) |
| IgG4 hinge sequence | | | | | C | P | A | P | (SEQ ID NO: 40) |
| IgG3 middle hinge sequence | P | C | P | R | | | | | (SEQ ID NO: 41) |
| Connecting peptide: | | | | Connecting peptide sequences | | | | | |
| G1 (Seq. ID NO: 7) | | | | | C | | | | GGGSSGGGSG |
| G1/G3/Pro243 (Seq. ID NO: 8) | P | C | P | R | C | P | | | GGGSSGGGSG |
| G1/G3/Pro243Ala244Pro245 (Seq. ID NO: 9) | P | C | P | R | C | P | A | P | GGGSSGGGSG |
| G1/Cys239Ser:Pro243 (Seq. ID NO: 10) | | | | | C | P | | | GGGSSGGGSG |
| G1/Cys239Ser:Pro243Ala244Pro245 (Seq. ID NO: 11) | | | | | C | P | A | P | GGGSSGGGSG |
| G1/Cys242Ser:Pro243 (Seq. ID NO: 12) | | | | | S | P | | | GGGSSGGGSG |
| G1/Cys242Ser:Pro243Ala244Pro245 (Seq. ID NO: 13) | | | | | S | P | A | P | GGGSSGGGSG |
| G1/Pro243Ala244Pro245 (Seq. ID NO: 14) | | | | | C | P | A | P | GGGSSGGGSG |
| G1/Pro243 (Seq. ID NO: 15) | | | | | C | P | | | GGGSSGGGSG |
| G4/G3/Pro243Ala244Pro245 (Seq. ID NO: 23) | P | C | P | R | C | P | A | P | |

Example 3

Construction of Connecting Polypeptides and Preferential Synthesis of Isoforms Nucleic acid sequences encoding the hinge region connecting peptides shown in Table 2 were introduced into CH2 domain deleted huCC49 gene sequences using the Splicing by Overlap Extension (SOE) method (Horton, R. M. 1993 Methods in Molecular Biology, Vol 15: PCR Protocols: Current Methods and applications. Ed. B. A. White). Correct modifications to the hinge region were confirmed by DNA sequence analysis. Plasmid DNA was used to transform CHO DG44 cells for stable production of antibody protein.

CH2 domain deleted huCC49 antibodies containing the eight designed synthetic connecting peptides indicated in Table 2 were constructed and antibody produced in CHO DG44 cells. Supernatants were collected from isolated cell lines and concentration of antibody in the culture supernatants determined by immunoassay. Supernatants containing antibody ranging from 0 to 30 ng of total antibody protein from each cell line was analyzed by non-reducing SDS-PAGE electrophoresis followed by Western Blot with anti-human kappa HRP conjugated antibody to detect CH2 domain deleted huCC49 Form A and Form B isoforms. Under these conditions, Form A migrates as a single 120 kDa homodimer and Form B as a 60 kDa doublet. Also visible are kappa chain monomer and dimers. Connecting peptides shown in SEQ ID NOs: 9, 9, 14, and 15 were all found to increase the proportion of Form A produced.

TABLE 3

The percentage of Form A antibody after affinity chromatography (Protein G) and after HIC purification

| CH2 domain deleted Antibody | % Form A Antibody | |
|---|---|---|
| | After Protein G | After HIC purification |
| HuCC49 (connecting peptide SEQ ID NO: 7) | 60 | 98 |
| HuCC49 PAP (connecting peptide SEQ ID NO: 14) | 83 | 98 |
| HuCC49 V2 PAP (connecting peptide SEQ ID NO: 14) | 90 | 99 |
| HuCC49 G1/G3/PAP (connecting peptide SEQ ID NO: 9) | 98 | Not done |
| HuCC49 V2 G1/G3/PAP (connecting peptide SEQ ID NO: 9) | 96 | Not done |

These data show that novel, engineered synthetic hinge region connecting peptides can be used to preferentially favor the formation of the A or B isoform. These studies also reveal the importance of the cysteine residues at position 242 (Kabat numbering system) in synthesizing the CH2 domain-deleted antibody Form A isoform. Substituting the cysteine at either position 239 or 242 with serine (e.g., using connecting peptides shown in SEQ ID NOs:10, 11, 12, or 13) shifts CH2 domain-deleted antibody biosynthesis to the Form B isoform. Accordingly, in one embodiment, a connecting peptide of the invention comprises a cysteine at least one of position 239 or 242. The use of connecting peptides which increase the proportion of Form A produced will lead to a beneficial improvement in process, yield and/or stability. These synthetic hinge region connecting peptides are useful for favoring synthesis of CH2 domain deleted antibody Form A isoform for any antibody isotype, e.g., IgG1, IgG2, IgG3, or IgG4, based on the extremely high degree of homology among the CH3 domains for all four human isotypes. Including identical and conserved amino acid residues, IgG1 CH3 domain is 98.13% homologous to IgG2 CH3, 97.20% homologous to IgG3 CH3, and 96.26% homologous to IgG4 CH3.

Example 4

Purification of Form A and Form B from a Monoclonal Antibody Mixture Containing Both Isoforms 10 mL of ddCC49 supernatant was titrated with 1M Tris pH 9.0 to a final pH of 7.5. This material was filtered through a series of Sol-Vac 0.8μ and 0.4μ membranes. A 100 mL XK50 Protein G column was pre-equilibrated with 1×PBS at a flow rate of 80 ml/min. The titrated, filtered supernatant was loaded onto the column at 80 ml/min. Bound protein was washed with the equilibrium buffer for 2.column volumes and then eluted with 100 mM Glycine at pH 3.0. The fractions containing the ddCC49 peak were collected and immediately titrated with 1 M Tris pH 9.0 to a final pH of 7.0.

A Toso Biosep Phenyl 5PW-HR column was pre-equilibrated with 20 mM Phosphate pH 7.2; 1 M Ammonium Sulfate. The Protein G eluate was titrated to 1 M Ammonium Sulfate using a 3.5 M Ammonium Sulfate pH 7.2 stock and loaded at a concentration of 2 mg/ml of gel bed. Bound protein was washed with a 20 mM Phosphate pH 4 or 7.2 Ammonium Sulfate to adjust the conductivity to 116.4 mS/cm. The material eluted from this condition has an apparent molecular weight about 120 kD (Form A) on a non-reducing SDS-PAGE. The remaining bound antibody was further eluted with a linear gradient of reducing Ammonium Sulfate content in the Phosphate buffer. This method separates Forms A and B in two separate peaks. The latter eluted antibody apparently lacks the disulfide linkage between the heavy chains and its molecular weight is about 60 kDa (Form B).

Both of the above purified materials can be recaptured by bringing the ammonium sulfate concentration to 1M and reloading it onto the cleaned Phenyl 5PW-HR column. Bound protein is eluted with 20 mM Phosphate pH 7.2 and dialyzed into 1×PBS.

Example 5

Comparison of Stability of Form A and Form B

The biologic activity of Forms A and B (as measured in preliminary experiments e.g., using direct binding or competition studies) revealed that Forms A and B have similar biologic activity.

The stability of Forms A and B was also compared. Purified ddCC49 molecules were concentrated to about 5 mg/ml by Amicon concentrator fitted with YM30 membrane (Millipore). The concentrated materials were equally divided into four portions for each isoforms and each fraction was put into 10K dialysis cassette (Pierce, cat# 66410) for 16 h dialysis in the following buffers: 1) 10 mM Sodium Phosphate, pH3; 2) 10 mM Sodium acetate, pH 5; 3) 10 mM Sodium Phosphate, pH 7; and 4) 10 mM Sodium Borate, pH 9. After dialysis, the protein concentration of each solution was adjusted to 3 mg/ml. In addition to the pure A and B isoform solution, a portion of A and B solutions from each pH were mixed to create a mixture containing 50% each isoform. Total of 12 formulations were created (four pH levels times 3 antibody solutions). The solutions were filtered and filled in 3 ml Type-1 glass serum vials (West Pharmaceuticals) with gray butyl stopper.

Three temperatures, 2-8° C., 20-25° C., and 38-42° C. were chosen to store the protein solutions for stability testing. Prior to storage, 500 µl samples were drawn from each formulation for physical and chemical analyses, these zero-time point data were referred to as control. Once in storage, samples were drawn at the following schedule, 2 weeks, 1 month, 2 months and 3 months and submitted for testing immediately.

To evaluate the physical and chemical stability of the two isoforms, the following methods were used: turbidity measured at $OD_{320}$, non-reducing SDS-PAGE, and size-exclusion chromatography.

Non-reducing SDS-PAGE was performed on for samples stored at 2-8° C., 20-25° C. and 38-42° C. for various time points. Both A and B form are relatively stable at pH 5 when stored at 2-8° C. However, when formulated at pH 7 and 9, both A and B forms showed degradation as indicated by increasing in number of bands that were smaller than the original major bands (120 kDa for form A and 60 kDa for form B). It was noticed that, particularly for pH 7 and 9 samples stored at low and intermediate temperatures, the intensity and number of bands that were less than 55 kDa were higher in B-isoform than A. This indicated that under these conditions the A-isoform is more stable than B-isoform. However, this seems not to be the case for A-isoform in pH 5 and stored at 20-25° C. This sample seemed to have more fragments than B-isoform. This appears to have been an artifact due to microbial contamination (discussed in more detail below). At high storage temperature, both forms at pH 9 were significantly degraded and there was almost no difference in gel patterns among the samples. Under this condition, trace amount of smear bands showed up at top of the gel which indicated the formation of aggregates. Because aggregates could be dissolved by SDS, the aggregation was investigated using the methods described in the following sections.

Table 4A through Table 4C list the turbidity data for ddCC49 stored at three different temperatures. The turbidity measures both the soluble and non-soluble aggregates and it is based on the amount of light scattered by these particles. When present, aggregates will scatter light and result in an increase in $A_{320}$. As showed in Table 4A-C, the turbidity of ddCC49 molecules stored at 2-8° C. increases as pH increased for both A and B isoforms, with the former being less turbid than the latter. This trend held true for samples stored for less than a month at higher temperatures (20-25° C. and 38-40° C.). As storage time reached 3 months, the turbidity increased significantly for samples at high pH and temperature, and the difference between A and B forms diminished. These results parallel those of SDS-PAGE and indicate that both isoforms are relatively stable (in terms of not forming aggregates) at pH 3 and 5, and that A-isoform is less susceptible to aggregation than the B isoform.

TABLE 4A

Turbidity measured at $A_{320}$ for ddCC49 samples stored at 2-8° C.

| Time (month) | A-isoform | | | | B-isoform | | | | Mixture | | | |
|---|---|---|---|---|---|---|---|---|---|---|---|---|
| pH = | 3 | 5 | 7 | 9 | 3 | 5 | 7 | 9 | 3 | 5 | 7 | 9 |
| 0 | 0.030 | 0.038 | 0.044 | 0.056 | 0.034 | 0.042 | 0.046 | 0.066 | 0.036 | 0.042 | 0.051 | 0.061 |
| ½ | 0.029 | 0.029 | 0.046 | 0.045 | 0.030 | 0.038 | 0.048 | 0.058 | 0.034 | 0.033 | 0.043 | 0.055 |
| 1 | 0.033 | 0.039 | 0.035 | 0.055 | 0.033 | 0.035 | 0.044 | 0.059 | 0.032 | 0.040 | 0.039 | 0.066 |
| 2 | 0.042 | 0.022 | 0.042 | 0.044 | 0.039 | 0.037 | 0.055 | 0.067 | 0.042 | 0.024 | 0.040 | 0.058 |
| 3 | 0.035 | 0.047 | 0.051 | 0.050 | 0.038 | 0.041 | 0.066 | 0.081 | 0.027 | 0.048 | 0.051 | 0.065 |

TABLE 4B

Turbidity measured at $A_{320}$ for ddCC49 samples stored at 20-25° C.

| Time (month) | A-isoform | | | | B-isoform | | | | Mixture | | | |
|---|---|---|---|---|---|---|---|---|---|---|---|---|
| pH = | 3 | 5 | 7 | 9 | 3 | 5 | 7 | 9 | 3 | 5 | 7 | 9 |
| ½ | 0.031 | 0.032 | 0.056 | 0.066 | 0.039 | 0.034 | 0.064 | 0.083 | 0.034 | 0.039 | 0.060 | 0.071 |
| 1 | 0.025 | 0.043 | 0.055 | 0.090 | 0.034 | 0.042 | 0.070 | 0.084 | 0.028 | 0.039 | 0.055 | 0.094 |
| 2 | 0.034 | 0.053 | 0.077 | 0.113 | 0.046 | 0.032 | 0.090 | 0.087 | 0.037 | 0.038 | 0.066 | 0.108 |
| 3 | 0.036 | 0.056 | 0.156 | 0.143 | 0.029 | 0.060 | 0.121 | 0.125 | 0.044 | 0.050 | 0.101 | 0.142 |

TABLE 4C

Turbidity measured at $A_{320}$ for ddCC49 samples stored at 38-42° C.

| Time (month) | A-isoform | | | | B-isoform | | | | Mixture | | | |
|---|---|---|---|---|---|---|---|---|---|---|---|---|
| pH = | 3 | 5 | 7 | 9 | 3 | 5 | 7 | 9 | 3 | 5 | 7 | 9 |
| ½ | 0.041 | 0.042 | 0.068 | 0.063 | 0.041 | 0.044 | 0.080 | 0.067 | 0.041 | 0.039 | 0.070 | 0.064 |
| 1 | 0.041 | 0.043 | 0.071 | 0.065 | 0.036 | 0.040 | 0.079 | 0.069 | 0.032 | 0.048 | 0.078 | 0.070 |
| 2 | 0.047 | 0.030 | 0.066 | 0.060 | 0.046 | 0.045 | 0.087 | 0.082 | 0.051 | 0.034 | 0.078 | 0.079 |
| 3 | 0.058 | 0.051 | 0.098 | 0.105 | 0.046 | 0.057 | 0.101 | 0.157 | 0.056 | 0.057 | 0.101 | 0.126 |

Size exclusion chromatography (SEC) is a powerful method for revealing the percent of intact molecules and the degraded products (both fragments and soluble aggregates) and is highly reproducible. In Table 4A-C the percent of intact monomer of A-isoform, B-isoform and the mixture stored at different temperatures are listed. For samples stored at 2-8° C., it is clear that Form A has a higher percentage of monomer as compared to Form B, and the mixture of Form A and Form B was somewhere in between. At this storage temperature, both forms were relatively stable at pH 3, 5 and 7 (with pH 5 being the most stable condition) for about three months. However, at pH 9 there was a significant decrease in percentage of monomer for Form B but only a slight decrease for Form A.

At elevated temperatures, all samples showed a significant decrease in percent of monomer as storage time increased; the A-isoform outperformed the B-isoform. However there was an exception, the sample of A-isoform in pH 5 stored at room temperature exhibited much more degradation than the B-isoform or the mixture under similar storage conditions. A close examination of this particular A-isoform vial, the data from SDS-PAGE, and SEC of the sample suggested that microbial contamination might have caused this unexpected result. First, both the SEC and SDS-PAGE results indicated that the degradation for this sample was primarily accounted for by a increase in fragmentation, presumably resulting from microbial digestion, otherwise some degree of increase in aggregation would have been expected. Second, the fact that the mixture sample, which contained 50% each of A and B-isoform, showed a better stability profile than B-isoform indicating that a more stable A-isoform must have contributed to the higher percent of monomer. Finally, A-isoform in pH 5 stored at 2-8° C. and 38-42° C. both showed higher percent of monomer than B-isoform under similar conditions. Therefore, intermediate storage temperature should have yielded similar results. Due to the limited amount of sample, an assay for microbial contamination could not be performed.

It was also noted that for both isoforms of IDEC-159 stored in high pH (9) and at 40° C., the percent of monomer reduced to about 30%. Under these severe conditions, the stability differences between the two isoforms disappeared. This SEC result mirrors of the results found using SDS-PAGE. Both results indicate that, although some chemical and physical characteristics differ between the two isoforms, the mechanism and by-products of degradation for both isoforms are similar, if not identical.

In summary, the SEC results indicate that both A and B-isoforms have optimal pH at about 5, and that A-isoform is more stable than B-isoform in terms of retaining higher percent of intact monomer at similar storage conditions.

TABLE 5A

Percent of monomer for ddCC49 samples stored at 2-8° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| 0 | 98.81 | 99.13 | 98.16 | 97.93 | 97.02 | 97.70 | 96.88 | 93.51 | 97.83 | 98.27 | 97.44 | 95.81 |
| ½ | 98.98 | 99.16 | 98.25 | 98.00 | 97.15 | 97.87 | 96.96 | 91.95 | 98.15 | 98.49 | 97.68 | 95.59 |
| 1 | 98.80 | 99.20 | 97.99 | 97.11 | 97.02 | 97.81 | 96.62 | 88.99 | 98.04 | 98.45 | 97.41 | 94.45 |
| 2 | 98.74 | 99.01 | 98.00 | 95.67 | 97.15 | 97.69 | 95.50 | 84.84 | 98.06 | 98.34 | 96.81 | 92.17 |
| 3 | 98.28 | 98.89 | 97.88 | 95.31 | 96.69 | 98.14 | 95.37 | 85.98 | 97.61 | 98.15 | 96.65 | 89.90 |

TABLE 5B

Percent of monomer for ddCC49 samples stored at 20-25° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| ½ | 97.83 | 99.04 | 97.12 | 93.65 | 95.84 | 97.62 | 93.71 | 79.61 | 96.75 | 98.30 | 95.37 | 87.67 |
| 1 | 96.60 | 96.63 | 95.65 | 88.09 | 94.38 | 97.23 | 90.69 | 72.26 | 95.36 | 97.99 | 93.05 | 80.92 |
| 2 | 93.62 | 92.79 | 93.17 | 80.06 | 91.71 | 96.96 | 85.51 | 66.53 | 92.78 | 97.51 | 89.33 | 73.91 |
| 3 | 92.81 | 89.56 | X | 74.31 | 89.30 | 96.04 | 82.57 | 63.25 | 90.46 | 97.02 | 86.80 | 69.36 |

TABLE 5C

Percent of monomer for ddCC49 samples stored at 38-42° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| ½ | 86.31 | 97.50 | 85.06 | 66.42 | 79.85 | 94.29 | 69.68 | 63.64 | 82.09 | 95.70 | 76.24 | 63.95 |
| 1 | 78.71 | 95.19 | 73.77 | 51.55 | 66.73 | 89.37 | 54.70 | 50.10 | 68.53 | 92.02 | 62.93 | 49.28 |
| 2 | 66.64 | 91.63 | 60.45 | 38.43 | 60.29 | 81.08 | 42.98 | 37.09 | 61.33 | 85.81 | 51.08 | 36.68 |
| 3 | 57.87 | 86.99 | 52.82 | 30.81 | 43.61 | 74.23 | 36.68 | 29.73 | 46.75 | 80.93 | 44.35 | 30.18 |

Example 7

Preparative Purification of Forms A and B

IDEC-159 (ddCC49) is a CH2 domain deleted monoclonal antibody directed against TAG-72 antigen, which is expressed on the surface of tumors. IDEC-159 contains two isoforms of the antibody, called Form A and Form B. The current cell culture process for IDEC-159 produces an approximate 50:50 ratio of Form A to Form B. The Form A isoform is an antibody with a deleted CH2 region in the $F_C$ portion of the heavy chain. In addition to having a deleted CH2 region, Form B also lacks the disulfide bond linkage across the $F_C$ region and is only held together by hydrophobic interactions and salt bridges.

The third and final chromatography step in the IDEC-159 purification process was developed to separate the two isoforms of IDEC-159. The separation is achieved by hydrophobic interaction chromatography (HIC), using a Phenyl TSK-gel 5PW-HR adsorbent. Since form B is more hydrophobic than form A, it adsorbs irreversibly to the stationary phase using approximately 0.73 M Ammonium Sulfate/20 mM Sodium Phosphate, pH 4.0-pH 7.0 as the mobile phase. Form A binds to a lesser extent to the stationary phase under these conditions and is therefore eluted isocratically, i.e. it leaves the column with the flowthrough fraction. Subsequent to the isocratic elution of Form A, omitting Ammonium sulfate from the mobile phase desorbs Form B. The following method was used to separate the two isoforms of IDEC-159:

- The column was sanitized using ≧3 CVs of 0.5 N NaOH, at ≦150 cm/hr.
- The column was equilibrated using ≧5 CVs of 0.73 M Ammonium Sulfate/20 mM Sodium Phosphate, pH 4.0, at ≦150 cm/hr.
- The column was loaded with room temperature TMAE Flowthrough that has been adjusted to include 0.43 volumes of 2.5 M Ammonium Sulfate/20 mM Sodium Phosphate, pH 4.0 liquid stock solution, at 5 mg per ml of resin.
- The antibody was loaded onto the column at pH 4.0, at ≦100 cm/hr.
- Collection of the antibody started when the outlet O.D. at 280 nm reaches 10 mAU.
- The column was washed using 15 CVs of 0.73 M Ammonium Sulfate/20 mM Sodium Phosphate, pH 4.0, at ≦100 cm/hr.
- Continue antibody collection throughout the 15 CV wash, then the outlet was diverted back to waste.
- The column was stripped using ≧5CVs of 20 mM Sodium Phosphate, pH 4.0, at ≦100 cm/hr. 6. The column was cleaned with ≧3 CVs 0.5 N NaOH, at ≦150 cm/hr.
- The column was equilibrated with ≧3 CVs of 0.73 M Ammonium Sulfate/20 mM Sodium Phosphate, pH 4.0, at ≦150 cm/hr.
- The column was stored in ≧3 CVs of 20% Ethanol, at ≧150 cm/hr.

The separation of the two forms at a preparative scale (5L column volume, total IDEC-159 load approximately 20 g) was performed. The first two peaks comprised the isocratic elution of Form A, the second peak comprised the eluted Form B, while the third peak contains impurities, which are removed from the stationary phase during cleaning.

The capability of this method to separate Forms A and B at preparative scale was also demonstrated by SDS PAGE.

Example 8

Figure 7:
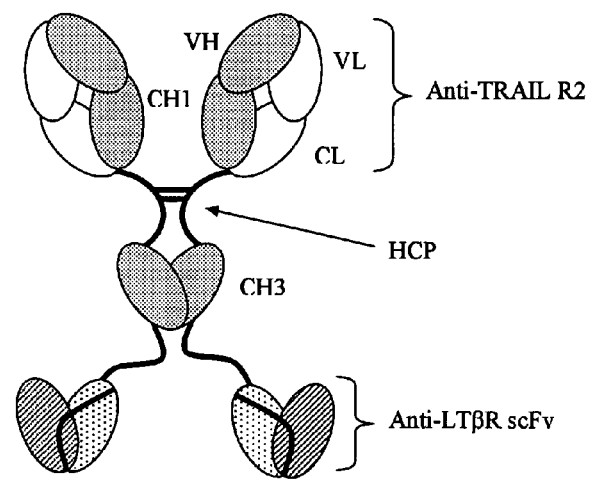
FIG. 7 shows a schematic diagram of a four chain tetravalent scFv CH2 domain deleted bispecific antibody (C-scFv tetravalent CH2 domain deleted bispecific antibody) comprising a scFv appended to the carboxyl terminus of CH3 and a hinge connecting peptide. Each heavy chain portion of the bispecific antibody contains an Fv region with binding specificity for the TRAIL R2 antigen and a scFv region with binding specificity for the LTβR antigen. The orientation of the VH and VL domains in the scFv may be changed and the respective antigen binding specificities may be altered. $G_4S$ is disclosed as SEQ ID NO: 46

Preparation of a Bispecific CH2 Domain-Deleted Tetravalent Antibody Comprising C-Terminal scFv Fragments and a Novel Connecting Peptide, and Preferential Synthesis of Isoform A A bispecific (anti-LTBR×anti-TRAILR2) CH2 domain-deleted sc(Fv)2 tetravalent antibody design was based on appending an anti-LTBR single chain Fv (scFv) to the carboxyl terminus of the anti-TRAILR2 CH2 domain-deleted antibody CH3 domain. A schematic diagram of the tetravalent bispecific domain-deleted antibody is shown in FIG. 7. An equivalent reference to this design is a C-scFv Tetravalent CH2 Domain Deleted antibody.

The preparation of single polypeptide chain binding molecules of the Fv region (i.e. single-chain Fv molecules) is described, e.g., in U.S. Pat. No. 4,946,778. Monoclonal anti-LTD☐R antibody CBE11 has been described previously in PCT publication WO 96/22788 and U.S. Pat. No. 6,312,691, and humanized CBE11 has been described in WO 02/30986. The anti-LTBR scFv is comprised of a VH and a VL region sequence tethered by a short synthetic linker (VH→(Gly4Ser)3 (SEQ ID NO: 17) linker→VL orientation) and was synthesized by PCR amplification from plasmid DNA pXWO25 containing humanized anti-LTBR scFv (huCBE11 scFv) in a pBluescript II SK vector. The 5' VH PCR primer included a Barn HI restriction endonuclease site followed by sequence encoding a (Gly4Ser)2 (SEQ ID NO: 42) linker peptide. The 3' VL PCR primer included a stop codon followed by a Barn HI site. The scFv was amplified with the above PCR primer set and the gene fragment gel isolated, digested with Barn HI restriction endonuclease, and cloned into a single Barn HI site previously introduced into a CH2 domain-deleted antibody expression vector containing a novel G1/G3/Pro243Ala244Pro245+[Gly/Ser] hinge (U.S. Ser. No. 10/880,320). Briefly, the vector was modified by removing an existing stop codon at the 3' end of the gene coding for the CH3 domain and replacing with nucleotides coding for the amino acid sequence Ser-Gly-Gly-Gly (SEQ ID NO: 43) immediately followed by a Barn HI restriction endonuclease site (coding for Gly-Ser). The Barn HI digested scFv fragment was cloned into the Barn HI site of the vector and screened for correct scFv orientation, resulting in a fusion product of the anti-LTBR scFv to the carboxyl terminus of the CH2 domain-deleted antibody CH3 domain through a 16 amino acid Ser(Gly$_4$Ser)$_3$ (SEQ ID NO: 44) linker. Correct anti-LTBR scFv sequences were confirmed by DNA sequence analysis.

The anti-TRAIL R2 variable domains were amplified by PCR and subsequently introduced into the above described construct to introduce the Fab domains. The 5' VL anti-TRAIL R2PCR primer included a Bgl II restriction endonuclease site, and the 3'VL anti-TRAIL R2PCR primer included a Bsi WI restriction endonuclease site. The murine VL region was amplified with the above set of PCR primers from the plasmid DNA substrate, pEAG1678, containing the ch14A2-hu kappa light chain. The 5' VH anti-TRAIL R2PCR primer included a Mlu I restriction endonuclease site followed by sequence encoding the 3' portion of the synthetic heavy leader and the 3' VH anti-TRAIL R2 PCR primer included a Nhe I restriction endonuclease site for fusing to the CH1 domain. The murine VH region was amplified with the above set of PCR primers from the plasmid DNA substrate, pEAG1678, containing the ch14A2-huIgG1 chain. Following amplification of the anti-TRAIL R2 VL and VH regions, the DNA fragments were gel isolated and ligated into the aforementioned vector. Correct sequences were confirmed by DNA sequence analysis.

Plasmid DNA was used to transform CHO DG44 cells for stable production of antibody protein. The engineered antibody was designated anti-LTBR×anti-TRAILR2 sc(Fv)2 tetravalent CH2 domain-deleted bispecific antibody. (C-scFv tetravalent CH2 domain-deleted anti-LTBR×anti-TRAIL R2 bispecific antibody). FIG. 10A (SEQ ID NO: 25) shows the DNA sequence of heavy chain C-scFv tetravalent CH2 domain-deleted anti-LTBR×anti-TRAIL R2 bispecific antibody containing the G1/G3/Pro243Ala244Pro245+[Gly/Ser] connecting peptide. FIG. 10B (SEQ ID NO: 26) shows the amino acid sequence of heavy chain C-scFv tetravalent CH2 domain-deleted anti-LTBR×anti-TRAIL R2 bispecific antibody containing the G1/G3/Pro243Ala244Pro245+[Gly/Ser] connecting peptide. FIG. 11A (SEQ ID NO: 27) shows the DNA sequence of light chain C-scFv tetravalent CH2 domain-deleted anti-LTBR×anti-TRAIL R2 bispecific antibody. FIG. 11B (SEQ ID NO: 28) shows the amino acid sequence of light chain C-scFv tetravalent CH2 domain-deleted anti-LTBR×anti-TRAIL R2 bispecific antibody To confirm the preferential synthesis of Isoform A, supernatants are collected from isolated cell lines and concentration of antibody in the culture supernatants is determined by immunoassay. Supernatants are analyzed by non-reducing SDS-PAGE electrophoresis followed by Western Blot with anti-human kappa-HRP conjugated antibody to detect Form A of the C-scFv tetravalent CH2 domain-deleted anti-LTBR× anti-TRAIL R2 bispecific antibody.
antibody product.

Example 9

Figure 8:
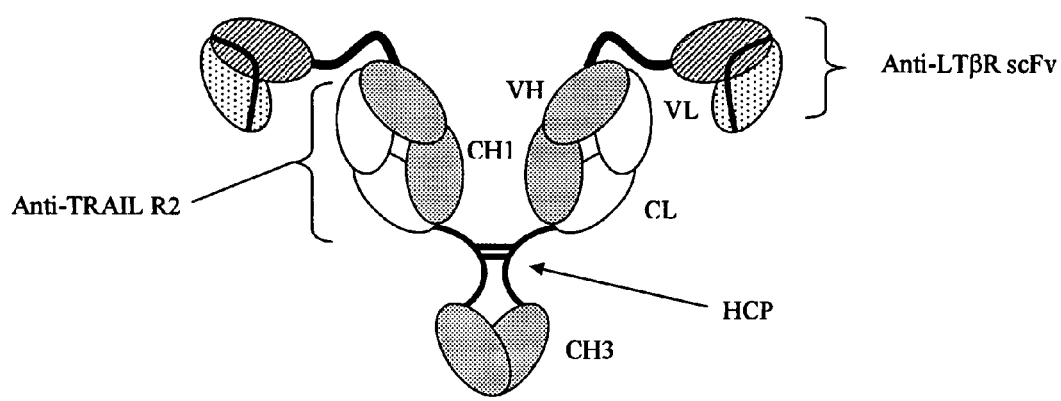
FIG. 8 shows a schematic diagram of a four chain tetravalent scFv CH2 domain deleted bispecific antibody ($N_H$-scFv tetravalent CH2 domain deleted bispecific antibody) comprising a scFv appended to the amino terminus of VH and comprising a hinge connecting peptide. Each heavy chain portion of the bispecific antibody contains an Fv region with binding specificity for the TRAIL R2 antigen and a scFv region with binding specificity for the LTβR antigen. The orientation of the VH and VL domains in the scFv may be changed and the respective antigen binding specificities may be altered. $G_4S$ is disclosed as SEQ ID NO: 46 and $(G_4S)_4G_3AS$ is disclosed as SEQ ID NO: 18.

Preparation of a Bispecific CH2 Domain-Deleted Tetravalent Antibody Comprising $N_H$-Terminal scFv Fragments and a Novel Connecting Peptide, and Preferential Synthesis of Isoform A A bispecific (anti-LTBR×anti-TRAILR2) CH2 domain-deleted sc(Fv)2 tetravalent antibody design was based on appending an anti-LTBR single chain Fv (scFv) to the amino terminus of the anti-TRAILR2 CH2 domain-deleted antibody VH domain. A schematic diagram of this tetravalent bispecific antibody is shown in FIG. 8. An equivalent reference to this design is $N_H$-scFv tetravalent CH2 domain-deleted bispecific antibody.

The preparation of single polypeptide chain binding molecules of the Fv region, single-chain Fv molecules, is described in U.S. Pat. No. 4,946,778. In order to facilitate fusion of the anti-LTBR scFv to the amino terminus of the anti-TRAIL R2 heavy chain variable domain a non-coding Bgl II restriction endonuclease site upstream of the VL leader was first removed. This modification resulted in a unique Bgl II cloning site encompassing amino acid positions 18-20 (A AGATCTCC) (SEQ ID NO:19) of anti-TRAIL R2 VH domain. The anti-LTBR scFv is comprised of a VH and a VL region sequence tethered by a short synthetic linker (VH→ (Gly4Ser)3 (SEQ ID NO: 17) linker→VL orientation) and was synthesized by PCR amplification. The 5' VH PCR primer included a Mlu I restriction endonuclease site followed by sequence encoding three amino acids of synthetic heavy leader. The 3' VL PCR primers consisted of an internal reverse primer encoding a (Gly4Ser)5 (SEQ ID NO: 45) linker and a second reverse primer encoding a partial anti-TRAIL R2 VH region and a Bgl II site. The anti-LTBR scFv +(Gly4Ser)5 (SEQ ID NO: 45) linker +partial anti-TRAIL R2 VH region was amplified in two sequential PCR reactions using the three aforementioned PCR primers through the common overlapping sequences encoding the (Gly4Ser)5 (SEQ ID NO: 45) linker in plasmid DNA pXWO25 containing the huCBE1 1 scFv in a pBluescript II SK vector. The anti-LTBR scFv+(Gly4Ser)5 1 (SEQ ID NO: 45) inker+partial anti-TRAIL R2 VH region gene fragment was gel isolated, digested with Mlu I and Bgl II restriction endonucleases and cloned into the Mlu I/Bgl II digested anti-TRAIL R2 CH2 domain-deleted vector containing the novel 1/G3/ Pro243Ala244Pro245+[Gly/Ser] hinge (U.S. Ser. No. 10/880,320) resulting in a fusion product of the anti-LTBR scFv to the amino terminus of the anti-TRAILR2 CH2 domain-deleted antibody VH domain through a 25 amino acid (Gly4Ser)5 (SEQ ID NO: 45) linker. Correct sequences were confirmed by DNA sequence analysis.

Plasmid DNA was used to transform CHO DG44 cells for stable production of antibody protein. The engineered antibody was designated $N_H$-scFv anti-LTBR×anti-TRAILR2 CH2 domain-deleted tetravalent bispecific antibody. FIG. 12A (SEQ ID NO: 29) shows the DNA sequence of heavy chain $N_H$-scFv anti-LTBR×anti-TRAILR2 CH2 domain-deleted tetravalent bispecific antibody containing the G1/G3/ Pro243Ala244Pro245+[Gly/Ser] connecting peptide. FIG. 12B (SEQ ID NO: 30) shows the amino acid sequence of heavy chain $N_H$-scFv anti-LTBR×anti-TRAILR2 CH2 domain-deleted tetravalent bispecific antibody containing the G1/G3/Pro243Ala244Pro245+[Gly/Ser] connecting peptide. FIG. 13A (SEQ ID NO: 31) shows the DNA sequence of light chain $N_H$-scFv anti-LTBR×anti-TRAILR2 CH2 domain-deleted tetravalent bispecific antibody. FIG. 13B (SEQ ID NO: 32) shows the amino sequence of light chain $N_H$-scFv anti-LTBR×anti-TRAILR2 CH2 domain-deleted tetravalent bispecific antibody.

To confirm the preferential synthesis of Isoform A, supernatants are collected from isolated cell lines and concentration of antibody in the culture supernatants is determined by immunoassay. Supernatants are analyzed by non-reducing SDS-PAGE electrophoresis followed by Western Blot with anti-human kappa-HRP conjugated antibody to detect Form A of the $N_H$-scFv tetravalent CH2 domain-deleted anti-LTBR×anti-TRAIL R2 bispecific antibody.

Example 10

Figure 9:
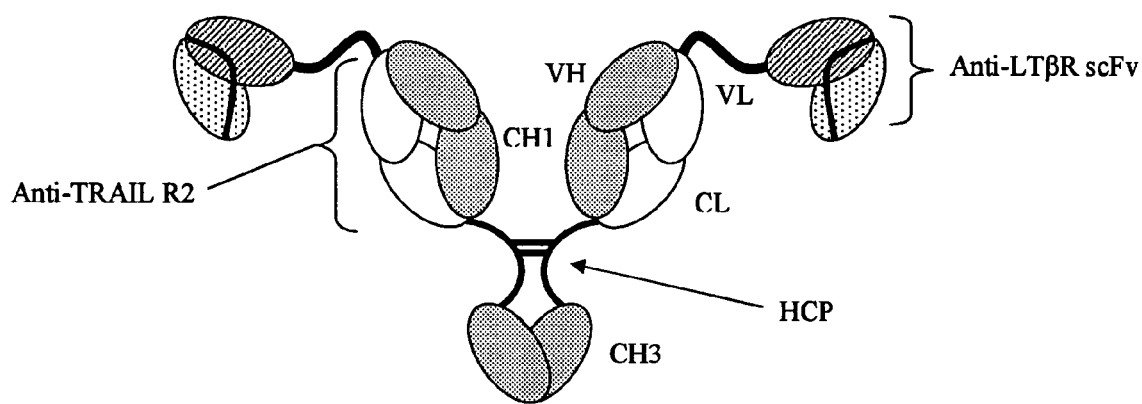
FIG. 9 shows a schematic diagram of a four chain tetravalent scFv CH2 domain deleted bispecific antibody ($N_L$-scFv tetravalent CH2 domain deleted bispecific antibody) comprising a scFv appended to the amino terminus of VL and comprising a hinge connecting peptide. Each heavy chain portion of the bispecific antibody contains an Fv region with binding specificity for the TRAIL R2 antigen and a scFv region with binding specificity for the LTβR antigen. The orientation of the VH and VL domains in the scFv may be changed and the respective antigen binding specificities may be altered. $G_4S$ is disclosed as SEQ ID NO: 46 and $(G_4S)_4G_3AS$ is disclosed as SEQ ID NO: 18.

Preparation of a Bispecific CH2 Domain-Deleted Tetravalent Antibody Comprising $N_L$-Terminal scFv Fragments and a Novel Connecting Peptide, and Preferential Synthesis of Isoform A A bispecific (anti-LTBR×anti-TRAILR2) CH2 domain-deleted sc(Fv)2 tetravalent antibody design was based on appending an anti-LTBR single chain Fv (scFv) to the amino terminus of the anti-TRAILR2 CH2 domain-deleted antibody VL domain. A schematic diagram of this tetravalent bispecific antibody is shown in FIG. 9. An equivalent reference to this design is $N_L$-scFv tetravalent CH2 domain-deleted bispecific antibody.

The strategy for preparing an NL-scFv anti-LTBR×anti-TRAILR2 CH2 domain-deleted tetravalent bispecific antibody was similar to the strategy outlined in Example 2. FIG. 14A (SEQ ID NO: 33) shows the DNA sequence of heavy chain $N_L$-scFv anti-LTBR×anti-TRAILR2 CH2 domain-deleted tetravalent bispecific antibody containing the G1/G3/ Pro243Ala244Pro245+[Gly/Ser] connecting peptide. FIG. 14B (SEQ ID NO: 34) shows the amino acid sequence of heavy chain $N_L$-scFv anti-LTBR×anti-TRAILR2 CH2 domain-deleted tetravalent bispecific antibody containing the G1/G3/Pro243Ala244Pro245+[Gly/Ser] connecting peptide. FIG. 15A (SEQ ID NO: 35) shows the DNA sequence of light chain $N_L$-scFv anti-LTBR×anti-TRAILR2 CH2 domain-deleted tetravalent bispecific antibody. FIG. 15B (SEQ ID NO: 36) shows the amino sequence of light chain $N_L$-scFv anti-LTBR×anti-TRAILR2 CH2 domain-deleted tetravalent bispecific antibody.

To confirm the preferential synthesis of Isoform A, supernatants are collected from isolated cell lines and concentration of antibody in the culture supernatants is determined by immunoassay. Supernatants are analyzed by non-reducing SDS-PAGE electrophoresis followed by Western Blot with anti-human kappa-HRP conjugated antibody to detect Form A of the $N_L$-scFv tetravalent CH2 domain-deleted anti-LTBR×anti-TRAIL R2 bispecific antibody.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A composition comprising bispecific dimeric binding molecules each bispecific binding molecule in the composition having at least four antigen binding sites and at least two polypeptide chains, wherein said at least two polypeptide chains each comprise a complete Ig heavy chain, and a chimeric hinge, wherein said chimeric hinge connects the CH1 and the CH2 domain of the Ig heavy chain, and wherein greater than about 50% of the bispecific dimeric binding molecules comprise polypeptide chains that are linked via at least one interchain disulfide linkage, and wherein amino acids at positions 226-242 (Kabat numbering) comprise: (i) the human IgG1 upper hinge region sequence EPKSCDKTHT (SEQ ID NO:2) or the human IgG4 upper hinge region sequence ESKYGPP (SEQ ID NO:20) at Kabat hinge positions 226-238; (ii) a cysteine residue (C) at Kabat hinge position 239; (iii) a proline residue (P) at Kabat hinge position 240; (iv) a proline (P) or serine (S) residue at Kabat hinge position 241; (v) the human IgG3 middle hinge sequence CPEPKSCDTPPPCPR (SEQ ID NO:24) at Kabat hinge positions 241EE-241SS; and (vi) a cysteine residue (C) at Kabat hinge position 242, and wherein said bispecific dimeric binding molecules comprise: at least a first binding site specific for LTβR and at least a second binding site specific for TRAIL-R2, wherein said antigen binding sites are selected from the group consisting of an antibody, an antigen binding fragment of an antibody, and an scFv molecule.

2. The composition of claim 1, wherein the bispecific dimeric binding molecules comprise two binding sites specific for LTβR and two binding sites specific for TRAIL-R2.

3. The composition of claim 1, wherein greater than about 90% of the bispecific dimeric binding molecules comprise polypeptides that are linked via at least one interchain disulfide linkage.

4. The composition of claim 1, wherein the polypeptide chains are linked via two or more interchain disulfide linkages.

5. The composition of claim 1, wherein the chimeric hinge comprises a proline residue at position 243, Kabat numbering system.

6. The composition of claim 1, wherein the heavy chain is from an antibody of an isotype selected from the group consisting of: IgG1, IgG2, IgG3, and IgG4.

7. The composition of claim 1, wherein the chimeric hinge further comprises an alanine residue at position 244 and a proline residue at position 245, Kabat numbering system.

8. The composition of claim 1, wherein the chimeric hinge comprises at least a portion of an IgG1 hinge domain, at least a portion of an IgG3 hinge domain.

9. The composition of claim 1, wherein the chimeric hinge comprises an amino acid sequence selected from the group consisting of: SEQ ID NOs: 8-15 and 23.

10. A composition comprising tetravalent binding molecules, each tetravalent binding molecule of the composition comprising at least two polypeptide chains and at least four antigen binding sites, wherein two of the polypeptide chains comprise an Ig heavy chain CH3 domain and a chimeric hinge interposed between the antigen binding site and the CH3 domain and wherein the polypeptide chains lack all or part of a CH2 domain, and wherein greater than about 50% of the molecules are present in a form in which two of the polypeptide chains are linked via at least one interchain disulfide linkage and wherein amino acids at positions 226-242 (Kabat numbering) comprise: (i) the human IgG1 upper hinge region sequence EPKSCDKTHT (SEQ ID NO:2) or the human IgG4 upper hinge region sequence ESKYGPP (SEQ ID NO:20) at Kabat hinge positions 226-238; (ii) a cysteine residue (C) at Kabat hinge position 239; (iii) a proline residue (P) at Kabat hinge position 240; (iv) a proline (P) or serine (S) residue at Kabat hinge position 241; (v) the human IgG3 middle hinge sequence CPEPKSCDTPPPCPR (SEQ ID NO:24) at Kabat hinge positions 241EE-241SS; and (vi) a cysteine residue (C) at Kabat hinge position 242, wherein said tetravalent binding molecule specifically crosslink at least two distinct TNF family receptors, and induces formation of heteromeric receptor complexes, wherein said tetravalent binding molecules comprise at least a first binding site specific for LTβR and at least a second binding site specific for TRAIL-R2, wherein the first and second binding sites are selected from the group consisting of an antibody, an antigen binding fragment thereof, an scFv molecule, and a ligand to the TNF receptor.

11. The composition of claim 10, wherein greater than about 90% of the binding molecules are linked via at least one interchain disulfide linkage.

12. The composition of claim 10 wherein at least one of the polypeptide chains comprises a CH3 domain genetically fused to a VL, VH or CH1 domain via the chimeric hinge.

13. The composition of claim 10, wherein the polypeptide chains lack the entire CH2 domain.

14. The composition of claim 10, wherein two of the polypeptide chains are linked via two or more interchain disulfide linkages.

15. The composition of claim 10, wherein the Ig heavy chain is from an antibody of an isotype selected from the group consisting of: IgG1, IgG2, IgG3, and IgG4.

16. The composition of claim 10, wherein the Ig heavy chain comprises a hinge region selected from the group consisting of: a γ1 hinge, a γ2 hinge a γ3 hinge, and a γ4 hinge.

17. The composition of claim 10, wherein the chimeric hinge comprises a proline residue at position 243, Kabat numbering system.

18. The composition of claim 10, wherein the chimeric hinge comprises at least a portion of an IgG1 hinge domain and at least a portion of an IgG3 hinge domain.

19. A composition comprising polypeptide dimers having at least four binding sites and at least two polypeptide chains, wherein said at least two polypeptide chains comprise (i) an Ig heavy chain lacking a CH2 domain, and (ii) a chimeric hinge,
wherein said chimeric hinge comprises an amino acid sequence selected from the group consisting of SEQ ID NOs: 8-15 and 23 and wherein said chimeric hinge connects said heavy chain to at least one of said binding sites, and
wherein greater than 50% of the polypeptide dimers comprise polypeptide chains that are linked via at least one interchain disulfide linkage, wherein said polypeptide dimers specifically crosslink at least two distinct TNF family receptors, and induces formation of heteromeric receptor complexes, said dimers comprising at least a first binding site specific for LTβR and at least a second binding site specific for TRAIL-R2, wherein the first and second binding sites are selected from the group consisting of an antibody, an antigen binding fragment thereof, an scFv molecule, and a ligand to the TNF receptor.

20. The composition of claim 19, wherein greater than 90% of the polypeptide dimers are linked via at least one interchain disulfide linkage.

21. The composition of claim 19, wherein the dimers are linked via two or more interchain disulfide linkages.

22. The composition of claim 19, wherein the heavy chain is from an antibody of an isotype selected from the group consisting of IgG1, IgG2, IgG3, and IgG4.

23. The composition of claim 1, wherein the heavy chain is from an antibody of an IgG3 isotype.

24. The composition of claim 10, wherein the heavy chain is from an antibody of an IgG3 isotype.

25. The composition of claim 19, wherein the heavy chain is from an antibody of an IgG3 isotype.

26. The composition of claim 10, wherein the chimeric hinge further comprises a gly-ser linker.

27. The composition of claim 26, wherein the gly-ser linker consists of the amino acid sequence GGGSSGGGSG (SEQ ID NO:1).

28. The composition of claim 1, wherein the Ig heavy chain is from an IgG4 molecule.

29. The composition of claim 10, wherein the Ig heavy chain is from an IgG4 molecule.

30. The composition of claim 19, wherein the Ig heavy chain is from an IgG4 molecule.

31. The composition of claim 10, wherein the chimeric hinge comprises the amino acid sequence of SEQ ID NO:8.

32. The composition of claim 10, wherein the chimeric hinge comprises the amino acid sequence of SEQ ID NO:9.

33. The composition of claim 10, wherein the chimeric hinge comprises the amino acid sequence of SEQ ID NO:23.

34. The composition of claim 10, wherein the binding molecule is a minibody consisting of two polypeptide chains, wherein said polypeptide chains each lack a CH1 domain and wherein the antigen binding sites are scFv molecules.

35. The composition of claim 10, wherein each binding molecule is a CH2 domain-deleted antibody consisting of four polypeptide chains, wherein said polypeptide chains lack the entire CH2 domain.

36. The composition of claim 1, wherein the first or second binding specificity is conferred by an antibody or antigen binding fragment thereof.

37. The composition of claim 1, wherein at least the first or second binding specificity is conferred by a single chain Fv fragment.

38. The composition of claim 1 further comprising a pharmaceutically acceptable carrier.

39. The composition of claim 10 further comprising a pharmaceutically acceptable carrier.

40. The composition of claim 19 further comprising a pharmaceutically acceptable carrier.

41. The composition of claim 10, wherein the tetravalent binding molecule comprises the amino acid sequence shown in FIG. 10B (SEQ ID NO: 26).

42. The composition of claim 10, wherein the binding molecule comprises the amino acid sequence shown in FIG. 11B (SEQ ID NO: 28).

43. The composition of claim 10, wherein the tetravalent binding molecule comprises the amino acid sequence shown in FIG. 12B (SEQ ID NO: 30).

44. The composition of claim 10, wherein the tetravalent binding molecule comprises the amino acid sequence shown in FIG. 13B (SEQ ID NO: 32).

45. The composition of claim 10, wherein the tetravalent binding molecule comprises the amino acid sequence shown in FIG. 14B (SEQ ID NO: 34).

46. The composition of claim 10, wherein the tetravalent binding molecule comprises the amino acid sequence shown in FIG. 15B (SEQ ID NO: 36).

* * * * *

UNITED STATES PATENT AND TRADEMARK OFFICE
CERTIFICATE OF CORRECTION

PATENT NO.         : 8,084,026 B2
APPLICATION NO.    : 11/825666
DATED              : December 27, 2011
INVENTOR(S)        : Scott Glaser et al.

It is certified that error appears in the above-identified patent and that said Letters Patent is hereby corrected as shown below:

In the claims:

At column 130, claim number 42, line 8, "The composition of claim 10, wherein the binding" should read --The composition of claim 10, wherein the tetravalent binding--

Signed and Sealed this
Thirteenth Day of March, 2012

David J. Kappos
*Director of the United States Patent and Trademark Office*